United States Patent
Proud

(10) Patent No.: US 9,406,220 B2
(45) Date of Patent: *Aug. 2, 2016

(54) TELEMETRY SYSTEM WITH TRACKING RECEIVER DEVICES

(71) Applicant: Hello Inc., San Francisco, CA (US)

(72) Inventor: James Proud, San Francisco, CA (US)

(73) Assignee: Hello Inc., San Francisco, CA (US)

( * ) Notice: Subject to any disclaimer, the term of this patent is extended or adjusted under 35 U.S.C. 154(b) by 99 days.

This patent is subject to a terminal disclaimer.

(21) Appl. No.: 13/966,641

(22) Filed: Aug. 14, 2013

(65) Prior Publication Data
US 2014/0247152 A1 Sep. 4, 2014

Related U.S. Application Data

(63) Continuation-in-part of application No. 13/923,909, filed on Jun. 21, 2013, and a continuation-in-part of application No. 13/923,637, filed on Jun. 21, 2013, now Pat. No. 8,810,430, and a continuation-in-part of (Continued)

(51) Int. Cl.
*G08C 19/16* (2006.01)
*G08C 17/02* (2006.01)
(Continued)

(52) U.S. Cl.
CPC .............. *G08C 17/02* (2013.01); *A61B 5/0022* (2013.01); *A61B 5/1118* (2013.01); *H02J 7/025* (2013.01); *H02J 17/00* (2013.01); *H04L 67/125* (2013.01); *H04W 4/005* (2013.01); *H04W 4/206* (2013.01); *A61B 5/0205* (2013.01); *A61B 5/6831* (2013.01); *A61B 2560/0214* (2013.01);

(Continued)

(58) Field of Classification Search
CPC .................. A61B 2560/0214; A61B 5/0022; H02J 7/0047; H04B 5/0031
See application file for complete search history.

(56) References Cited

U.S. PATENT DOCUMENTS 3,127,363 A 3/1964 Nitzsche et al.
3,715,334 A 2/1973 Karstedt
(Continued)

FOREIGN PATENT DOCUMENTS

DE 3839900 A1 5/1990
EP 0183553 A2 6/1986
(Continued)

OTHER PUBLICATIONS

Davids, G.I., et al., "On enabling secure applications through off-line biometric identification", Proceedings of the IEEE Symposium on Security and Privacy (May 1998).
(Continued)

*Primary Examiner* — Omeed Alizada

(57) ABSTRACT

A wireless power transmission system includes, a transmit antenna which in operation produces a wireless field, an amplifier coupled to the transmit antenna, a load sensing circuit coupled to the amplifier and a controller coupled to the load sensing circuit. A monitoring device has one or more sensors and a unique user ID. The one or more sensors acquire user information selected from of at least one of, a user's activities, behaviors and habit information. The monitoring device includes an ID circuitry. A communication interface receives information about the unique user ID when the load sensing circuit indicates the monitoring device is within the wireless field. The indication is created using at least a change in power consumption.

8 Claims, 47 Drawing Sheets

Related U.S. Application Data application No. 13/923,614, filed on Jun. 21, 2013, now Pat. No. 8,850,421, and a continuation-in-part of application No. 13/923,809, filed on Jun. 21, 2013, and a continuation-in-part of application No. 13/923,750, filed on Jun. 21, 2013, and a continuation-in-part of application No. 13/923,583, filed on Jun. 21, 2013, now abandoned, and a continuation-in-part of application No. 13/923,560, filed on Jun. 21, 2013, now Pat. No. 8,803,366, and a continuation-in-part of application No. 13/923,543, filed on Jun. 21, 2013, and a continuation-in-part of application No. 13/923,937, filed on Jun. 21, 2013.

(60) Provisional application No. 61/772,265, filed on Mar. 4, 2013, provisional application No. 61/823,502, filed on May 15, 2013.

(51) Int. Cl.

| | | |
|---|---|---|
| *H02J 7/02* | (2016.01) | |
| *H02J 17/00* | (2006.01) | |
| *A61B 5/11* | (2006.01) | |
| *H04L 29/08* | (2006.01) | |
| *H04W 4/00* | (2009.01) | |
| *H04W 4/20* | (2009.01) | |
| *H02J 7/00* | (2006.01) | |
| *A61B 5/00* | (2006.01) | |
| *A61B 5/0205* | (2006.01) | |

(52) U.S. Cl.
CPC ..... *A61B 2562/08* (2013.01); *H02J 2007/0096* (2013.01); *H04L 67/12* (2013.01); *H04L 67/22* (2013.01); *H04W 4/008* (2013.01)

(56) References Cited

U.S. PATENT DOCUMENTS

| | | | |
|---|---|---|---|
| 3,775,452 | A | 11/1973 | Karstedt |
| 3,813,364 | A | 5/1974 | Zuba et al. |
| 3,814,730 | A | 6/1974 | Karstedt |
| 4,394,317 | A | 7/1983 | McAfee et al. |
| 4,603,152 | A | 7/1986 | Laurin et al. |
| 4,780,556 | A | 10/1988 | Hata et al. |
| 5,057,151 | A | 10/1991 | Schuster et al. |
| 5,187,657 | A | 2/1993 | Forbes |
| 5,319,363 | A | 6/1994 | Welch et al. |
| 5,348,008 | A | 9/1994 | Bornn et al. |
| 5,564,429 | A | 10/1996 | Bornn et al. |
| 5,576,054 | A | 11/1996 | Brown |
| 5,735,887 | A | 4/1998 | Barreras, Sr. et al. |
| 5,910,544 | A | 6/1999 | Ozawa et al. |
| 5,971,941 | A | 10/1999 | Simons et al. |
| 6,038,315 | A | 3/2000 | Strait et al. |
| 6,120,467 | A | 9/2000 | Schallhorn |
| 6,200,289 | B1 | 3/2001 | Hochman et al. |
| 6,221,012 | B1 | 4/2001 | Maschke et al. |
| 6,323,846 | B1 | 11/2001 | Westerman et al. |
| 6,416,471 | B1 | 7/2002 | Kumar et al. |
| 6,440,067 | B1 | 8/2002 | DeLuca et al. |
| 6,454,708 | B1 | 9/2002 | Ferguson et al. |
| 6,570,557 | B1 | 5/2003 | Westerman et al. |
| 6,580,356 | B1 | 6/2003 | Alt et al. |
| 6,661,372 | B1 | 12/2003 | Girerd et al. |
| 6,677,932 | B1 | 1/2004 | Westerman |
| 6,893,396 | B2 * | 5/2005 | Schulze ............... A61B 5/0022 128/903 |
| 7,113,932 | B2 | 9/2006 | Tayebnejad et al. |
| 7,248,894 | B2 | 7/2007 | Fujieda et al. |
| 7,502,643 | B2 | 3/2009 | Farringdon et al. |
| 7,614,008 | B2 | 11/2009 | Ording |
| 7,616,110 | B2 | 11/2009 | Crump et al. |
| 7,633,076 | B2 | 12/2009 | Huppi et al. |
| 7,653,883 | B2 | 1/2010 | Hotelling et al. |
| 7,657,849 | B2 | 2/2010 | Chaudhri et al. |
| 7,663,607 | B2 | 2/2010 | Hotelling et al. |
| 7,720,855 | B2 | 5/2010 | Brown |
| 7,733,224 | B2 | 6/2010 | Tran |
| 7,844,914 | B2 | 11/2010 | Andre et al. |
| 7,957,762 | B2 | 6/2011 | Herz et al. |
| 7,959,567 | B2 | 6/2011 | Stivoric et al. |
| 8,006,002 | B2 | 8/2011 | Kalayjian et al. |
| 8,028,905 | B2 | 10/2011 | Holberg |
| 8,033,996 | B2 | 10/2011 | Behar |
| 8,044,363 | B2 | 10/2011 | Ales et al. |
| 8,126,729 | B2 | 2/2012 | Dicks et al. |
| 8,126,735 | B2 | 2/2012 | Dicks et al. |
| 8,157,731 | B2 | 4/2012 | Teller et al. |
| 8,204,786 | B2 | 6/2012 | LeBoeuf et al. |
| 8,239,784 | B2 | 8/2012 | Hotelling et al. |
| 8,251,903 | B2 | 8/2012 | LeBoeuf et al. |
| 8,279,180 | B2 | 10/2012 | Hotelling et al. |
| 8,328,718 | B2 | 12/2012 | Tran |
| 8,352,211 | B2 | 1/2013 | Vock et al. |
| 8,369,936 | B2 | 2/2013 | Farringdon et al. |
| 8,378,811 | B2 | 2/2013 | Crump et al. |
| 8,381,135 | B2 | 2/2013 | Hotelling et al. |
| 8,389,627 | B2 | 3/2013 | Rubinsztajn et al. |
| 8,390,463 | B2 | 3/2013 | Munthe-Kaas et al. |
| 8,398,546 | B2 | 3/2013 | Pacione et al. |
| 8,452,235 | B2 * | 5/2013 | Kirby ............... H04B 5/0031 307/104 |
| 8,479,122 | B2 | 7/2013 | Hotelling et al. |
| 8,587,426 | B2 | 11/2013 | Bloem |
| 8,663,106 | B2 | 3/2014 | Stivoric et al. |
| 2002/0015024 | A1 | 2/2002 | Westerman et al. |
| 2002/0109600 | A1 | 8/2002 | Mault et al. |
| 2002/0178126 | A1 | 11/2002 | Beck et al. |
| 2003/0023467 | A1 | 1/2003 | Moldovan |
| 2003/0121033 | A1 | 6/2003 | Peev et al. |
| 2003/0143113 | A2 | 7/2003 | Yuzhakov et al. |
| 2004/0044799 | A1 | 3/2004 | Sivaraman et al. |
| 2004/0172290 | A1 | 9/2004 | Leven |
| 2005/0113650 | A1 | 5/2005 | Pacione et al. |
| 2005/0137480 | A1 | 6/2005 | Alt et al. |
| 2005/0190059 | A1 | 9/2005 | Wehrenberg |
| 2005/0245839 | A1 | 11/2005 | Stivoric et al. |
| 2006/0017692 | A1 | 1/2006 | Wehrenberg et al. |
| 2006/0026536 | A1 | 2/2006 | Hotelling et al. |
| 2006/0030891 | A1 | 2/2006 | Saltzstein et al. |
| 2006/0033724 | A1 | 2/2006 | Chaudhri et al. |
| 2006/0064030 | A1 | 3/2006 | Cosentino et al. |
| 2006/0066449 | A1 | 3/2006 | Johnson |
| 2006/0089592 | A1 | 4/2006 | Kadhiresan et al. |
| 2006/0098772 | A1 | 5/2006 | Reho et al. |
| 2006/0136270 | A1 | 6/2006 | Morgan et al. |
| 2006/0159645 | A1 | 7/2006 | Miller et al. |
| 2006/0197753 | A1 | 9/2006 | Hotelling |
| 2006/0264778 | A1 | 11/2006 | Lim et al. |
| 2007/0149862 | A1 | 6/2007 | Pipke |
| 2007/0167753 | A1 | 7/2007 | Van Wyk et al. |
| 2007/0174633 | A1 | 7/2007 | Draper et al. |
| 2008/0012701 | A1 | 1/2008 | Kass et al. |
| 2008/0076969 | A1 | 3/2008 | Kraft et al. |
| 2008/0146890 | A1 | 6/2008 | LeBoeuf et al. |
| 2009/0023428 | A1 | 1/2009 | Behzad et al. |
| 2009/0088820 | A1 | 4/2009 | Mao et al. |
| 2009/0112247 | A1 | 4/2009 | Freeman et al. |
| 2009/0119760 | A1 | 5/2009 | Hung et al. |
| 2009/0182208 | A1 | 7/2009 | Cho et al. |
| 2009/0234206 | A1 | 9/2009 | Gaspard et al. |
| 2009/0240120 | A1 | 9/2009 | Mensinger et al. |
| 2009/0255122 | A1 | 10/2009 | Azrielant |
| 2009/0318773 | A1 | 12/2009 | Jung et al. |
| 2010/0141042 | A1 | 6/2010 | Kesler et al. |
| 2010/0153269 | A1 | 6/2010 | McCabe |
| 2010/0234695 | A1 | 9/2010 | Morris |
| 2010/0277003 | A1 | 11/2010 | Von Novak et al. |
| 2011/0055132 | A1 | 3/2011 | Mahdian et al. |
| 2011/0068935 | A1 | 3/2011 | Riley et al. |
| 2011/0179450 | A1 | 7/2011 | Kim et al. |
| 2012/0035487 | A1 | 2/2012 | Werner et al. |

(56) References Cited

U.S. PATENT DOCUMENTS

| | | |
|---|---|---|
| 2012/0133079 A1 | 5/2012 | Sykes et al. |
| 2012/0146795 A1 | 6/2012 | Margon et al. |
| 2012/0149996 A1 | 6/2012 | Stivoric et al. |
| 2012/0170305 A1 | 7/2012 | Rudek et al. |
| 2012/0170521 A1 | 7/2012 | Vogedes et al. |
| 2012/0184876 A1 | 7/2012 | Freeman et al. |
| 2012/0194341 A1 | 8/2012 | Peichel et al. |
| 2012/0194419 A1 | 8/2012 | Osterhout et al. |
| 2012/0196832 A1 | 8/2012 | Luria |
| 2012/0205373 A1 | 8/2012 | Caldwell |
| 2012/0225719 A1 | 9/2012 | Nowozin et al. |
| 2012/0226639 A1 | 9/2012 | Burdick et al. |
| 2012/0229270 A1 | 9/2012 | Morley et al. |
| 2012/0242501 A1 | 9/2012 | Tran et al. |
| 2012/0253485 A1 | 10/2012 | Weast et al. |
| 2012/0253489 A1 | 10/2012 | Dugan et al. |
| 2012/0290327 A1 | 11/2012 | Hanlon et al. |
| 2012/0290950 A1 | 11/2012 | Rapaport et al. |
| 2012/0302920 A1 | 11/2012 | Bridger et al. |
| 2012/0330109 A1 | 12/2012 | Tran |
| 2013/0022659 A1 | 1/2013 | Roberts |
| 2013/0030711 A1 | 1/2013 | Korhonen |
| 2013/0035785 A1 | 2/2013 | MacVittie et al. |
| 2013/0127980 A1 | 5/2013 | Haddick et al. |
| 2013/0154851 A1 | 6/2013 | Gaskill et al. |
| 2013/0172691 A1 | 7/2013 | Tran |
| 2013/0175732 A1 | 7/2013 | Lust et al. |
| 2013/0255681 A1 | 10/2013 | Batch et al. |
| 2013/0267794 A1 | 10/2013 | Fernstrom et al. |
| 2013/0326790 A1 | 12/2013 | Cauwels |
| 2014/0019468 A1 | 1/2014 | Federoff et al. |
| 2014/0129942 A1 | 5/2014 | Rathod |
| 2014/0266939 A1 | 9/2014 | Baringer et al. |

FOREIGN PATENT DOCUMENTS

| | | |
|---|---|---|
| EP | 0271423 A1 | 6/1988 |
| EP | 0369255 A2 | 5/1990 |
| EP | 371004 A1 | 5/1990 |
| EP | 0477681 A2 | 4/1992 |
| EP | 0567253 A1 | 10/1993 |
| EP | 0640663 A2 | 3/1995 |
| EP | 0654497 A1 | 5/1995 |
| EP | 1094091 | 4/2001 |
| EP | 1094091 A1 | 4/2001 |
| EP | 1113042 A2 | 7/2001 |
| EP | 1133936 A1 | 9/2001 |
| EP | 1172414 A2 | 1/2002 |
| EP | 1217042 A1 | 6/2002 |
| EP | 1367534 A2 | 12/2003 |
| EP | 1371004 A2 | 12/2003 |
| EP | 1555297 A1 | 7/2005 |
| EP | 1595676 A1 | 11/2005 |
| EP | 1785454 A1 | 5/2007 |
| EP | 1792944 A1 | 6/2007 |
| EP | 1883798 A1 | 2/2008 |
| EP | 2052352 A1 | 4/2009 |
| EP | 2063555 A1 | 5/2009 |
| EP | 2428774 A1 | 3/2012 |
| EP | 2582116 A2 | 4/2013 |
| EP | 2614945 A2 | 7/2013 |
| GB | 1278798 A | 6/1972 |
| GB | 1381933 A | 1/1975 |
| GB | 2460890 A | 12/2009 |
| WO | WO-8704449 A1 | 7/1987 |
| WO | WO-9500992 A1 | 1/1995 |
| WO | WO-9956922 A1 | 11/1999 |
| WO | WO-02063555 A2 | 8/2002 |
| WO | WO-2006127726 A1 | 11/2006 |
| WO | WO-2008050951 A1 | 5/2008 |
| WO | WO-2012/170305 A1 | 12/2012 |
| WO | WO-2013076676 A1 | 5/2013 |
| WO | WO-2013081447 A1 | 6/2013 |

OTHER PUBLICATIONS

Juels, A., et al., "A Fuzzy Vault Scheme", Proceedings of the 2002 IEEE Symposium on Information Theory (Jun. 2002).

Juels, A., et al., "A fuzzy commitment scheme", Proc. 5th ACM Conference on Comp. and Commun. Security, pp. 28-36 (1999).

Yang, S., et al., "Secure fuzzy vault fingerprint verification system", Asilomar Conf. on Signals, Systems and Comp., vol. 1, pp. 577-581 (Nov. 2004).

Uludag, U., et al., "Fuzzy fingerprint value", Proc. Workshop: Biometrics: Challenges arising from theory to practice, pp. 13-16 (Aug. 2004).

* cited by examiner

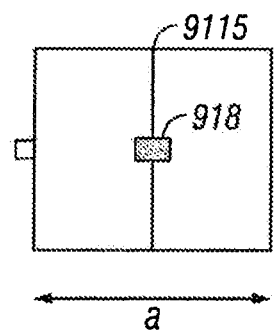
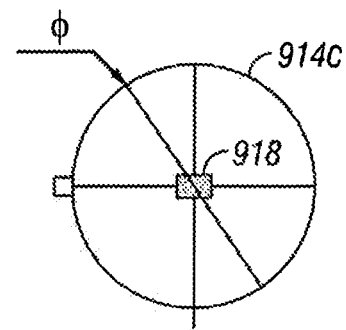
FIG. 42a             FIG. 42b
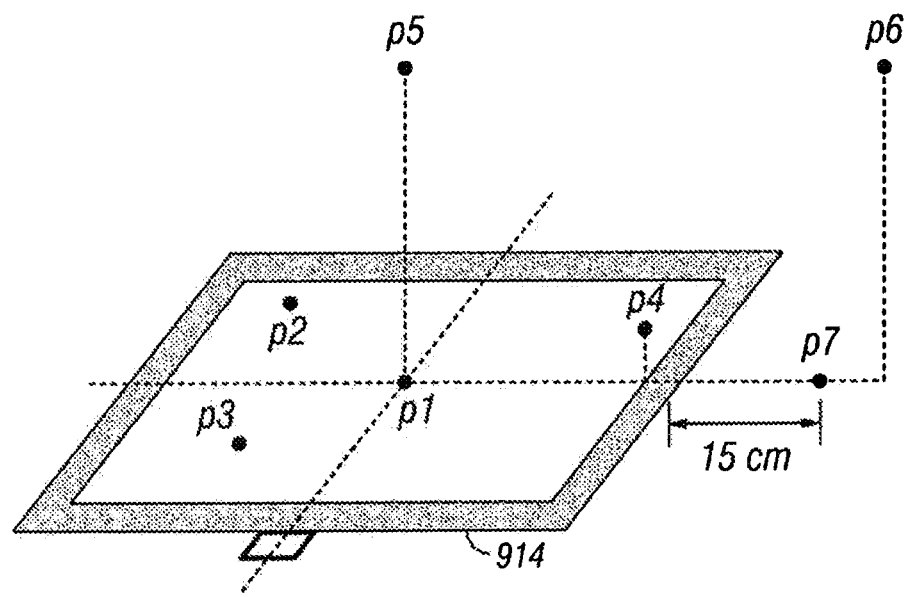
FIG. 43

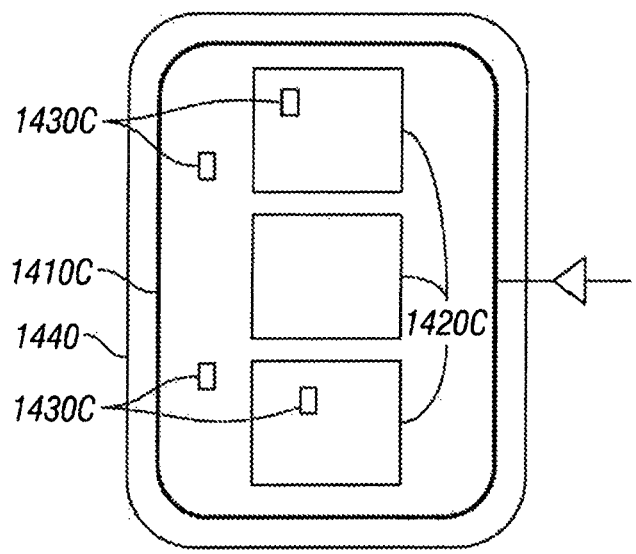
FIG. 51a
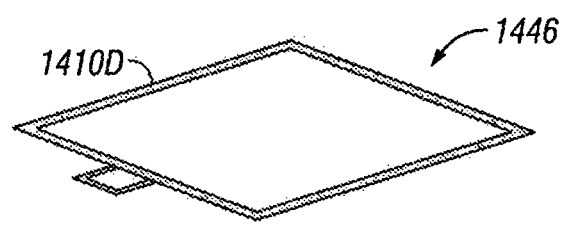
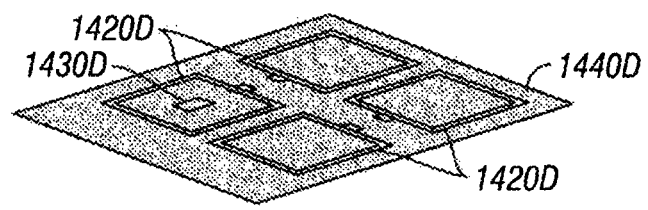
FIG. 51b

TELEMETRY SYSTEM WITH TRACKING RECEIVER DEVICES

CROSS-REFERENCE TO RELATED APPLICATIONS

This application is a continuation in part of U.S. Ser. Nos. 13/923,909, 13/923,637, 13/923,614, 13/923,809, 13/923,750, 13/923,583, 13/923,560, 13/923,543, and 13/923,937, all filed Jun. 21, 2013 and all of which claim the benefit of U.S. 61/772,265, U.S. 61/812,083 and 61/823,502. All of the above-identified applications are fully incorporated herein by reference.

BACKGROUND OF THE INVENTION

1. Field of the Invention

The present invention relates generally to wireless charging, and more particularly to devices, systems, and methods related to tracking receiver monitoring devices that may be located in wireless power systems.

2. Description of the Related Art

Telemetry systems can be implemented to acquire and transmit data from a remote source. Some telemetry systems provide information about a user's activities.

It is becoming commonplace to use wireless packet data service networks for effectuating data sessions with. In some implementations, unique identifications (ID) need to be assigned to the devices in order to facilitate certain aspects of service provisioning, e.g., security, validation and authentication, et cetera. In such scenarios, it becomes imperative that no two devices have the same indicium (i.e., collision). Further, provisioning of such indicia should be flexible so as to maintain the entire pool of indicia to a manageable level while allowing for their widespread use in multiple service environments.

The telemetry system can incorporate a wireless technology such as wireless fidelity (WiFi); infrared (IR); or ultrasound in order to facilitate finding an object and/or data transmission. As an exemplary implementation, a medical telemetry system can be implemented to remotely monitor the cardiac electrical activity of a plurality of ambulatory patients while they remain within a predefined coverage area. The medical telemetry system can also be implemented to locate and track patients within the coverage area.

Wireless electronic devices require typically require their own charger and power source, which is usually an alternating current (AC) power outlet. Such a wired configuration becomes unwieldy when many devices need charging.

Approaches are being developed that use over-the-air or wireless power transmission between a transmitter and a receiver coupled to the electronic device to be charged. Such approaches generally fall into two categories. One is based on the coupling of plane wave radiation (also called far-field radiation) between a transmit antenna and a receive antenna on the device to be charged. The receive antenna collects the radiated power and rectifies it for charging the battery. Antennas are generally of resonant length in order to improve the coupling efficiency. This approach suffers from the fact that the power coupling falls off quickly with distance between the antennas, so charging over reasonable distances (e.g., less than 1 to 2 meters) becomes difficult. Additionally, since the transmitting system radiates plane waves, unintentional radiation can interfere with other systems if not properly controlled through filtering.

Other approaches to wireless energy transmission techniques are based on inductive coupling between a transmit antenna embedded, for example, in a "charging" mat or surface and a receive antenna (plus a rectifying circuit) embedded in the electronic device to be charged. This approach has the disadvantage that the spacing between transmit and receive antennas must be very close (e.g., within millimeters). Though this approach does have the capability to simultaneously charge multiple devices in the same area, this area is typically very small and requires the user to accurately locate the devices to a specific area.

Each battery powered device, such as a wireless monitoring device, requires its own charger and power source. Such a wired configuration becomes unwieldy when many devices need charging.

Approaches are being developed that use over-the-air or wireless power transmission between a transmitter and a receiver coupled to the electronic device to be charged. Such approaches generally fall into two categories. One is based on the coupling of plane wave radiation (also called far-field radiation) between a transmit antenna and a receive antenna on the device to be charged. The receive antenna collects the radiated power and rectifies it for charging the battery. Antennas are generally of resonant length in order to improve the coupling efficiency. This approach suffers from the fact that the power coupling falls off quickly with distance between the antennas, so charging over reasonable distances (e.g., less than 1 to 2 meters) becomes difficult. Additionally, since the transmitting system radiates plane waves, unintentional radiation can interfere with other systems if not properly controlled through filtering.

Other approaches to wireless energy transmission techniques are based on inductive coupling between a transmit antenna embedded, for example, in a "charging" mat or surface and a receive antenna (plus a rectifying circuit) embedded in the host electronic device to be charged. This approach has the disadvantage that the spacing between transmit and receive antennas must be very close (e.g., within thousandths of meters). Though this approach does have the capability to simultaneously charge multiple devices in the same area, this area is typically very small and requires the user to accurately locate the devices to a specific area. Therefore, there is a need to provide a wireless charging arrangement that accommodates flexible placement and orientation of transmit and receive antennas.

With wireless power transmission there is a need for systems and methods for transmitting and relaying wireless power for convenient and unobtrusive wireless power transmission to receiver devices. There is also a need for tracking and reporting on receiver devices that may or may not be within a wireless charging zone.

SUMMARY OF THE INVENTION

An object of the present invention is to provide improved wireless power transmission.

Another object of the present invention is to provide systems and methods for transmitting and relaying wireless power for monitoring devices.

A further object of the present invention is to provide tracking and reporting on receiver monitoring devices that may or may not be within a wireless charging zone.

These and other objects of the present invention are achieved in, a wireless power transmission system that includes, a transmit antenna which in operation produces a wireless field, an amplifier coupled to the transmit antenna, a load sensing circuit coupled to the amplifier and a controller coupled to the load sensing circuit. A monitoring device has one or more sensors and a unique user ID. The one or more sensors acquire user information selected from of at least one of, a user's activities, behaviors and habit information. The monitoring device includes an ID circuitry. A communication interface receives information about the unique user ID when the load sensing circuit indicates the monitoring device is within the wireless field. The indication is created using at least a change in power consumption.

In another embodiment of the present invention, a method detects a presence of monitoring devices. A presence of a monitoring device is detected with a receive antenna within an area covered by a wireless field. The monitoring device has one or more sensors and a unique user ID. The one or more sensors acquire user information selected from of at least one of, a user's activities, behaviors and habit information. The monitoring device has ID circuitry. The wireless field is generated at a resonant frequency of a transmit antenna of a host device upon detecting the presence of the monitoring device within the area covered by the wireless field. A request is received for power from the monitoring device via a communication channel. The unique ID is received from the monitoring device via the communication channel. Notification information about the device is provided on a notifier responsive to the unique user ID. Generation of the wireless field is stopped when a presence of a second monitoring device is detected within the area indicates an absence of monitoring devices within the area.

BRIEF DESCRIPTION OF THE DRAWINGS

FIGS. 42(a) and 42(b) show layouts of loop antennas for transmit and receive antennas according to exemplary embodiments of the present invention.

FIG. 43 shows various placement points for a receive antenna relative to a transmit antenna to illustrate coupling strengths in coplanar and coaxial placements.

FIG. 51(a) illustrates a large transmit antenna with a three different smaller repeater antennas disposed coplanar with, and within a perimeter of, the transmit antenna.

FIG. 51(b) illustrates a large transmit antenna with smaller repeater antennas with offset coaxial placements and offset coplanar placements relative to the transmit antenna.

DETAILED DESCRIPTION

Figure 1A:
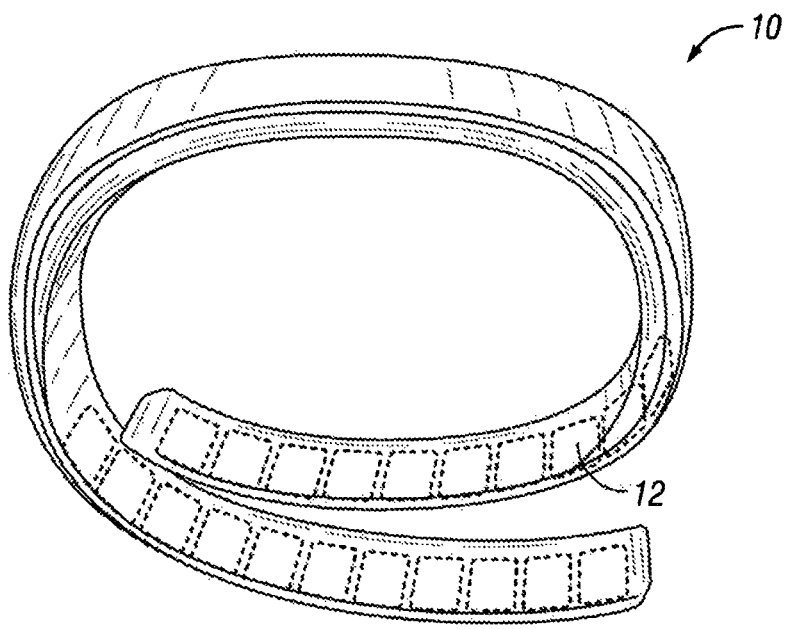
FIGS. 1(a) and 1(b) illustrate one embodiment of a wearable device of the present invention, where one size fits all.

As used herein, the term engine refers to software, firmware, hardware, or other component that can be used to effectuate a purpose. The engine will typically include software instructions that are stored in non-volatile memory (also referred to as secondary memory). When the software instructions are executed, at least a subset of the software instructions can be loaded into memory (also referred to as primary memory) by a processor. The processor then executes the software instructions in memory. The processor may be a shared processor, a dedicated processor, or a combination of shared or dedicated processors. A typical program will include calls to hardware components (such as I/O devices), which typically requires the execution of drivers. The drivers may or may not be considered part of the engine, but the distinction is not critical.

As used herein, the term database is used broadly to include any known or convenient means for storing data, whether centralized or distributed, relational or otherwise.

As used herein a mobile device includes, but is not limited to, a cell phone, such as Apple's iPhone®, other portable electronic devices, such as Apple's iPod Touches®, Apple's iPads®, and mobile devices based on Google's Android® operating system, and any other portable electronic device that includes software, firmware, hardware, or a combination thereof that is capable of at least receiving the signal, decoding if needed, exchanging information with a transaction server to verify the buyer and/or seller's account information, conducting the transaction, and generating a receipt. Typical components of mobile device may include but are not limited to persistent memories like flash ROM, random access memory like SRAM, a camera, a battery, LCD driver, a display, a cellular antenna, a speaker, a BLUETOOTH® circuit, and WIFI circuitry, where the persistent memory may contain programs, applications, and/or an operating system for the mobile device.

As used herein, the terms "social network" and "SNET" comprise a grouping or social structure of devices and/or individuals, as well as connections, links and interdependencies between such devices and/or individuals. Members or actors (including devices) within or affiliated with a SNET may be referred to herein as "nodes", "social devices", "SNET members", "SNET devices", "user devices" and/or "modules". In addition, the terms "SNET circle", "SNET group" and "SNET sub-circle" generally denote a social network that comprises social devices and, as contextually appropriate, human SNET members and personal area networks ("PANs").

A used herein, the term "wearable device" is anything that can be worn by an individual and that has a back side that in some embodiments contacts a user's skin and a face side. Examples of wearable device include but are not limited to a cap, arm band, wristband, garment, and the like.

As used herein, the term "computer" is a general purpose device that can be programmed to carry out a finite set of arithmetic or logical operations. Since a sequence of operations can be readily changed, the computer can solve more than one kind of problem. A computer can include of at least one processing element, typically a central processing unit (CPU) and some form of memory. The processing element carries out arithmetic and logic operations, and a sequencing and control unit that can change the order of operations based on stored information. Peripheral devices allow information to be retrieved from an external source, and the result of operations saved and retrieved.

As used herein, the term "Internet" is a global system of interconnected computer networks that use the standard Internet protocol suite (TCP/IP) to serve billions of users worldwide. It is a network of networks that consists of millions of private, public, academic, business, and government networks, of local to global scope, that are linked by a broad array of electronic, wireless and optical networking technologies. The Internet carries an extensive range of information resources and services, such as the inter-linked hypertext documents of the World Wide Web (WWW) and the infrastructure to support email. The communications infrastructure of the Internet consists of its hardware components and a system of software layers that control various aspects of the architecture.

As used herein, the term "extranet" is a computer network that allows controlled access from the outside. An extranet can be an extension of an organization's intranet that is extended to users outside the organization that can be partners, vendors, and suppliers, in isolation from all other Internet users. An extranet can be an intranet mapped onto the public Internet or some other transmission system not accessible to the general public, but managed by more than one company's administrator(s). Examples of extranet-style networks include but are not limited to:

LANs or WANs belonging to multiple organizations and interconnected and accessed using remote dial-up LANs or WANs belonging to multiple organizations and interconnected and accessed using dedicated lines Virtual private network (VPN) that is comprised of LANs or WANs belonging to multiple organizations, and that extends usage to remote users using special "tunneling" software that creates a secure, usually encrypted network connection over public lines, sometimes via an ISP.

As used herein, the term "Intranet" is a network that is owned by a single organization that controls its security policies and network management. Examples of intranets include but are not limited to:

A LAN

A Wide-area network (WAN) that is comprised of a LAN that extends usage to remote employees with dial-up access A WAN that is comprised of interconnected LANs using dedicated communication lines A Virtual private network (VPN) that is comprised of a LAN or WAN that extends usage to remote employees or networks using special "tunneling" software that creates a secure, usually encrypted connection over public lines, sometimes via an Internet Service Provider (ISP).

As used herein, the term (patient monitoring) includes: (i) Cardiac monitoring, which generally refers to continuous electrocardiography with assessment of the patient's condition relative to their cardiac rhythm. A small monitor worn by an ambulatory patient for this purpose is known as a Holter monitor. Cardiac monitoring can also involve cardiac output monitoring via an invasive Swan-Ganz catheter (ii) Hemodynamic monitoring, which monitors the blood pressure and blood flow within the circulatory system. Blood pressure can be measured either invasively through an inserted blood pressure transducer assembly, or noninvasively with an inflatable blood pressure cuff. (iii) Respiratory monitoring, such as: pulse oximetry which involves measurement of the saturated percentage of oxygen in the blood, referred to as SpO2, and measured by an infrared finger cuff, capnography, which involves CO2 measurements, referred to as EtCO2 or end-tidal carbon dioxide concentration. The respiratory rate monitored as such is called AWRR or airway respiratory rate). (iv) Respiratory rate monitoring through a thoracic transducer belt, an ECG channel or via capnography, (v) Neurological monitoring, such as of intracranial pressure. Special patient monitors can incorporate the monitoring of brain waves electroencephalography, gas anesthetic concentrations, bispectral index (BIS), and the like, (vi) Blood glucose monitoring using glucose sensors. (vii) Childbirth monitoring with sensors that monitor various aspects of childbirth. (viii) Body temperature monitoring which in one embodiment is through an adhesive pad containing a thermoelectric transducer. (ix) Stress monitoring that can utilize sensors to provide warnings when stress levels signs are rising before a human can notice it and provide alerts and suggestions. (x) Epilepsy monitoring. (xi) Toxicity monitoring, and the like.

Additionally the present invention can be used to detect differences for a variety of blood tests, including but not limited to tests for the following: sodium, potassium, chloride, urea, creatinine, calcium, albumin, fasting glucose, amylase, carcinoembryonic antigen, glycosylated hemoglobin, hemoglobin, erthrocytes hemoglobin and the like.

As used herein, the term wireless power means any form of energy associated with electric fields, magnetic fields, electromagnetic fields, or otherwise that is transmitted between from a transmitter to a receiver without the use of physical electromagnetic conductors.

For purposes of the present invention, the Internet, extranets and intranets collectively are referred to as ("Network Systems").

As used herein, "wireless power" means any form of energy associated with electric fields, magnetic fields, electromagnetic fields, or otherwise that is transmitted between from a transmitter to a receiver without the use of physical electromagnetic conductors.

Figure 1B:
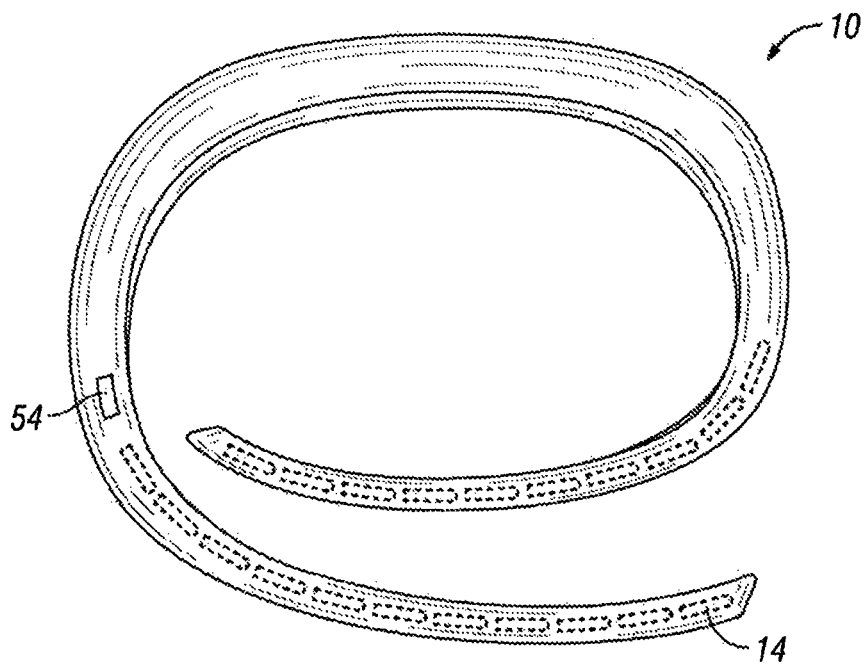

In various embodiments, the present invention provides a monitoring device 10, such as a wearable device, where in one embodiment; one size fits all, a patient monitoring device 10, and the like. As illustrated in FIGS. 1(a) and 1(b), in one embodiment of the present invention, the monitoring device 10 includes a plurality of magnets 12, with adjacent magnets having opposite polarity, with a length suitable to be worn by all people. In one embodiment, the length of the monitoring device 10 can be 10-12 inches. The magnets 12 are positioned along an interior of the monitoring device 10 to be provided for good conformation to a user's wrist.

One or more sensors 14 are coupled to the monitoring device 10. The sensors are measuring devices. As a non-limiting example, the measuring device or sensors 14 can include RTSS devices to detect a user's activities, motions, physical parameters, and the like, including but not limited to, a heart rate monitor, a body temperature probe, a conventional pedometer, an accelerometer and the like.

Alternatively, multifunctional sensors 14 which can perform all the aforementioned functions of RTSS may be attached or embedded in monitoring device 10. In one embodiment, each sensor can be in communication and or connect electronically and/or RF to a telemetry module 16. A variety of different sensors 14 can be utilized, including but not limited to, an accelerometer based sensor, and pressure based sensors, voltage resistance sensor, a radio frequency sensor, and the like, as recited above.

As a non-limiting example, an accelerometer, well known to those skilled in the art, detects acceleration and thus user activity. The accelerometer provides a voltage output that is proportional to the detected acceleration. Accordingly, the accelerometer senses vibration. This voltage output provides an acceleration spectrum over time; and information about loft time can be ascertained by performing calculations on that spectrum. A microprocessor subsystem, such as disclosed in U.S. Pat. No. 8,352,211, incorporated herein by reference, stores the spectrum into memory and processes the spectrum information to determine activity. Other examples of suitable accelerometer sensors are disclosed in EP 2428774 A1, incorporated herein by reference. Suitable pressure sensors are disclosed in EP 1883798 B1, incorporated herein by reference. A suitable voltage resistance sensor is disclosed in EP 1883798 B1, incorporated herein by reference. A suitable radio frequency sensor is disclosed in EP 2052352 B1, incorporated herein by reference.

Figure 2:
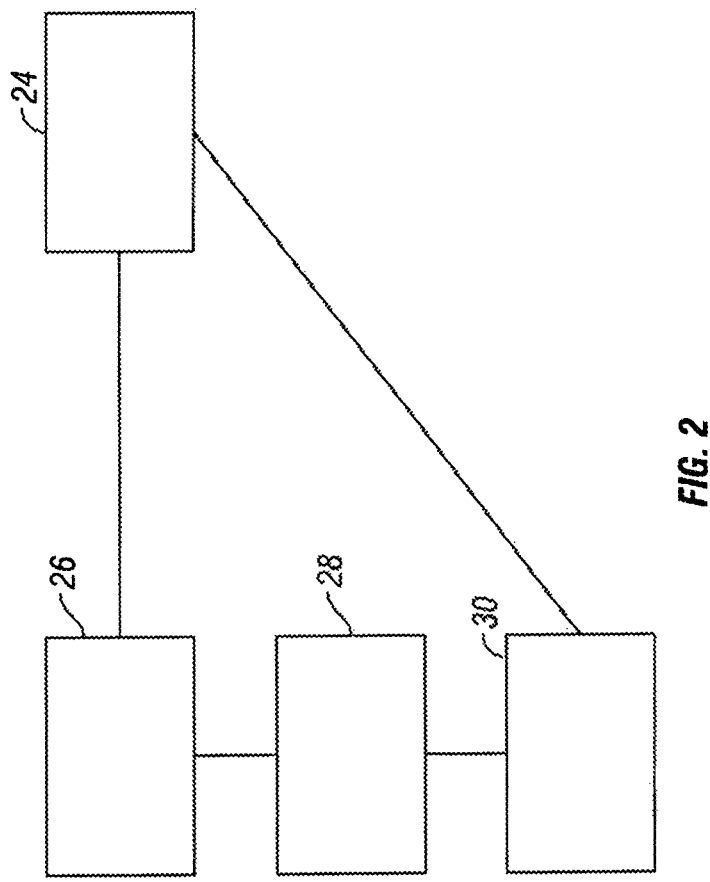
FIG. 2 illustrates one embodiment of electronics that can be included in the wearable device.

Referring to FIG. 2, in various embodiments, the monitoring device 10, also known as the monitoring device, can include a power source 24, such a battery that can be rechargeable. The battery 24 can be put into a sleep state when not actively used in order to preserve power. A wake up feature allows the battery 24 and other electronics of the monitoring device 10 to "sleep" during non-use or and is initiated into the "wake up" mode by certain predestinated events.

Figure 3:
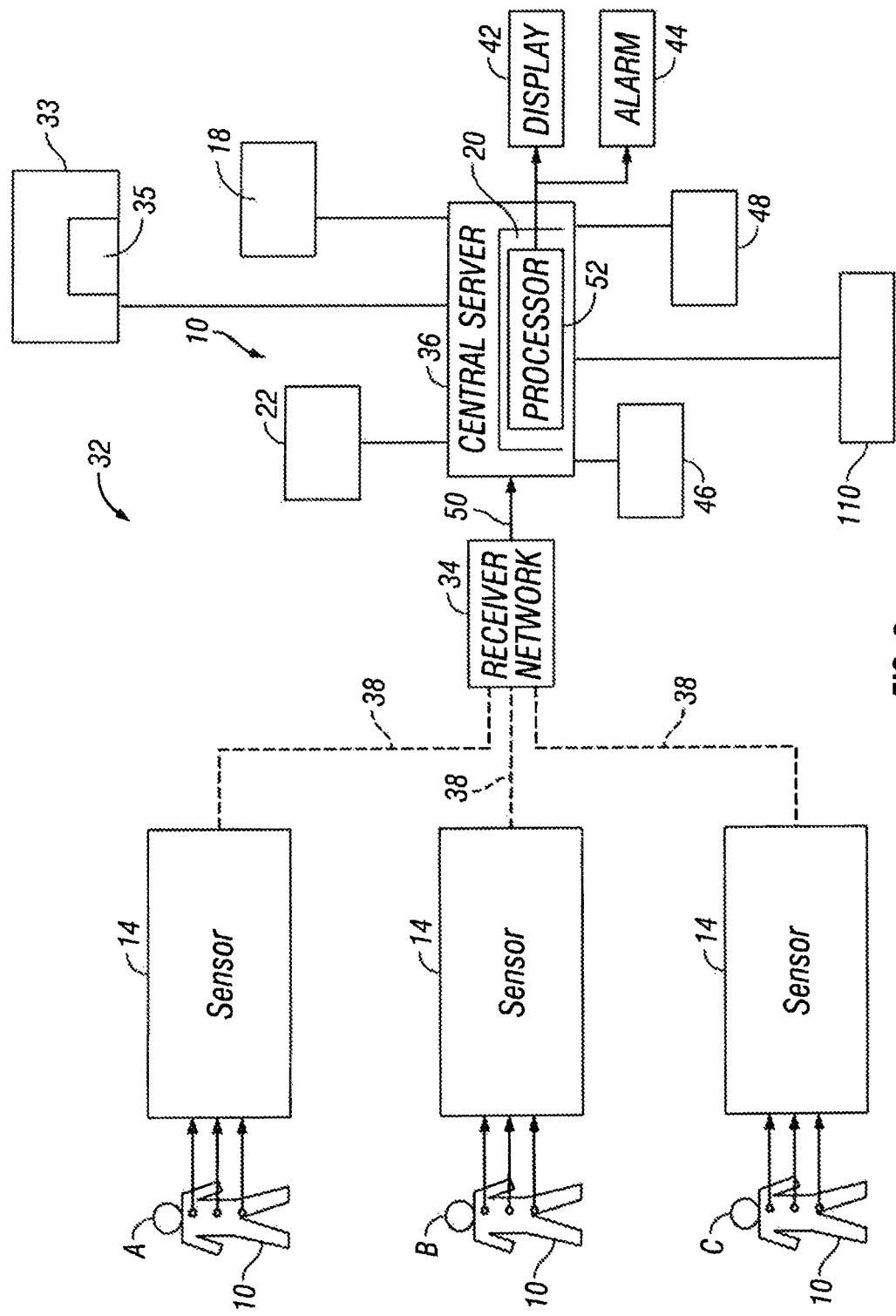
FIG. 3 illustrates one embodiment of a telemetry system of the present invention.

In one embodiment, as illustrated in FIG. 3, a telemetry system server 16 is coupled to a database 18. Each monitoring device 10 is assigned its own unique identification, ID or asset tag or more fully explained hereafter.

The data transmitted by the monitoring device 10 sensors 14 and its ID may be coded by appending a seed to digital data bits. As illustrated in FIG. 3 central processor unit 20 (CPU) validates or rejects received upon detection of the seed string appended to the digital data bits. In the alternative, the digital data bits may be coded and decoded by applying a scrambling algorithm utilizing the seed. A programming device 22 may be configured to transmit data to a sensor 14, also known as a monitoring device, utilizing a variety of alternative transmission means, including, for example, RF, IR, optical, and the like, or a magnetic loop/induction system.

In one embodiment, sensors 14 are configured to be shipped to users in a non-programmable mode with all programming already performed at the factory. A random seed may be communicated to the programming device 22 can a variety of different mechanisms, including but not limited to, via scanning a bar code, manual input, magnetic strip, random number generation, and the like.

Referring again to FIG. 2, in one embodiment, the monitoring device 10 includes a control unit 26 that puts the monitoring device 10 in a low power state. A monitoring system 28 can be included that remains active. The monitoring system 28 wakes up the electronics 30 in the monitoring device 10 from a low power state. The control unit 26 can be notified of awaking of the other components by the monitoring system 28. The control unit 26 can set a status bit on the monitoring system 28 only when the battery 24 needs to be in a full power state. The control unit 26 then forces a power cycle.

Referring to FIG. 3, one embodiment of a telemetry system 32 is illustrated. The telemetry system 32 is in the communication with the sensors 14 and or monitoring device 14 and ID of the monitoring device 10 and can include one or more receivers 34, a central server 36 with the CPU 20. The telemetry system 32 can optionally include a display 42 and an alarm 44. The telemetry system 32 receives information from sensors 14 and or the monitoring device of a user's habits, activities, and the like, and then processes this information. Monitoring device 10 with its unique ID and sensors 14 is assigned to a specific user in order to track and/or monitor that user. For illustrative purposes assume that three users A, B AND C are being tracked and monitored by the telemetry system 32. It should, however, be appreciated that the telemetry system 32 may be implemented to track and/or monitor a much larger number of users.

In various embodiments, the telemetry system 32 can send firmware updates or repairs to the monitoring device 14 during an update mode of the monitoring system, when the monitoring device is not in use by the user. The update mode can be when the user does not know that the monitoring device is being up-dated. The update mode can occur without disrupting service to the user. The firmware update can be sent by the telemetry system 32 directly or indirectly to the monitoring device 14, with the firmware update or a copy of the firmware update then resides on the monitoring device 14.

In one embodiment of the present invention, radio frequency (RF) devices that are sensors 14 and/or chips may serve as the identifying devices. Each source, sensor 14, ID and the like can carry a fixed radio frequency chip encoded with identifying data which may be correlated to the individual participants, parts or objects.

Telemetry system 32 of the present invention may include a Real-Time Location System (RTLS) 46 and Real-Time Sensing System (RTSS) 48 with RF technology. The RF technology may include active and/or passive RFID sensors 14 and an RF wireless array system as a receiver 34. The RF technology in the RTLS 46 and RTSS 48 may include UWB technology (e.g., IEEE 802.15), WLAN technology (e.g., IEEE 802.11), SAW RFID positioning system technology, GPS technology, and the like.

The sensors 14 may communicate directly with each other and/or relay telemetry data directly to base receiving RF device(s) or base receivers 34. The base receivers 34 may forward the telemetry data to a base computer either through a direct link or through a Network System 101. Alternatively the telemetry data may be forwarded to end user devices, including but not limited to, laptops, mobile devices and the like, either directly or through a Network System 101. The comprehensive telemetry system 32 using RF technologies such as UWB, ZigBee, Wi-Fi, GPS data system can be utilized as described above.

The readers/antennae may be interconnected using a LAN, such as Ethernet to provide a Network System 101 communication infrastructure for the computers and servers. Active and passive RFID sensors 14 may be employed. The active sensors 14 (RFID) may have a two-way communication function, which allows the base computer system to dynamically manage the sensors 14; vary update rates; send self-identification and telemetry data.

The active sensors 14 may employ dual-radio architecture. In one embodiment, active sensors 14 transmit radio pulses, which are used to determine precise two-dimensional or three-dimensional location and a conventional bi-directional radio, which is used as a control and telemetry channel with a sensor update rate.

The monitoring device 10 gathers telemetry data, communicates that data to a base station, BLUETOOTH® enabled device, or smart phone and the like. The monitoring device can receive firmware updates and repairs from the telemetry system, as previously stated, directly or indirectly from the base station, via a BLUETOOTH® enabled device, and the like. The monitoring device 10 can receive updates wirelessly. The base station can receive firmware updates from Network Systems 101, take telemetry data from the monitoring device 10 and transfer it to Network Systems 101. Telemetry data received from the base station is analyzed by servers and presented to an end user. Any third party device can receive data from the monitoring device 10 wirelessly and deliver information to the servers for processing.

In one embodiment, the monitoring device 10 uses an accelerometer, gyroscope, GPS sensor, a BLUETOOTH® chip, and a heart rate monitor.

As a non-limiting example, for heart monitoring, the accelerometer, sensor 14, determines when to sample the sensors 14 and to improve the accuracy of the heart rate monitor. The gyroscope detects movement and orientation and the GPS sensor is used to determine location of the user. A BLUETOOTH® chip allows the device to connect wirelessly to other third party devices.

As a non-limiting example, a heart rate monitor 14 detects the user's heart rate in order to accurately determine the user's activity level, behavioral patterns and the like.

An Artificial Intelligence (AI) or Machine Learning-grade algorithms is used to identify the user's activities, behaviors, behaviors and perform analysis. Examples of AI algorithms include Classifiers, Expert systems, case based reasoning, Bayesian networks, and Behavior based AI, Neural networks, Fuzzy systems, Evolutionary computation, and hybrid intelligent systems. A brief description of these algorithms is provided in Wikipedia and stated below.

Classifiers are functions that can be tuned according to examples. A wide range of classifiers are available, each with its strengths and weaknesses. The most widely used classifiers are neural networks, support vector machines, k-nearest neighbor algorithms, Gaussian mixture models, naive Bayes classifiers, and decision trees. Expert systems apply reasoning capabilities to reach a conclusion. An expert system can process large amounts of known information and provide conclusions based on them.

A case-based reasoning system stores a set of problems and answers in an organized data structure called cases. A case based reasoning system upon being presented with a problem finds a case in its knowledge base that is most closely related to the new problem and presents its solutions as an output with suitable modifications. A behavior based AI is a modular method of building AI systems by hand. Neural networks are trainable systems with very strong pattern recognition capabilities.

Fuzzy systems provide techniques for reasoning under uncertainty and have been widely used in modern industrial and consumer product control systems. An Evolutionary Computation applies biologically inspired concepts such as populations, mutation and survival of the fittest to generate increasingly better solutions to the problem. These methods most notably divide into evolutionary algorithms (e.g., genetic algorithms) and swarm intelligence (e.g., ant algorithms). Hybrid intelligent systems are any combinations of the above. It is understood that any other algorithm, AI or otherwise, may also be used. Examples of suitable algorithms that can be used with the embodiments of the present invention are disclosed in, EP 1371004 A4, EP 1367534 A2, US 20120226639 and US 20120225719, all incorporated fully herein by reference.

In various embodiments, the monitoring device 10 has additional features. In one embodiment, the monitoring device 10 changes color, via infrared LEDs, to accurately match the wearer's skin tone. This creates a seamless and more personal integration of technology into the user's daily life. In this embodiment, there is skin contact with the monitoring device 10.

In another embodiment, the monitoring device 10 remotely reminds and can be used to administer medications. As a non-limiting example, the monitoring device 10 can inject adrenalin. In one embodiment, the monitoring device 10 has sleep pattern recognition based on movement and heart rate.

In various embodiments, the monitoring device 10 uses algorithms to determine activity type, behavioral patterns and user habits based on collected data.

In one embodiment, the monitoring device 10 uses the accelerometer information to improve the heart rate monitor. As a non-limiting example, the monitoring device 10 detects movement and speed. Addition of this data improves the accuracy of the heart rate monitor and corrects for any miscalculations in vibration, noise and skin color.

In one embodiment, velocity readouts and accelerometer data are used to measure when to sample heart rate. For example, if the monitoring device 10 registers zero velocity readout, the user is probably at rest or engaged in a passive activity. Thus, the monitoring device 10 knows not to sample heart rate. This results in conversation of time, energy and data storage.

User activity, performance and action can be based on the acceleration and angular velocity of the monitoring device 10. In one embodiment, the monitoring device 10 has a feature where the monitoring device 10 authorizes third party interaction based on hand gesture, on previous interactions or patterns of behavior. As a non-limiting example, if one purchases a coke every day for the last two weeks, the monitoring device 10 can "orders" the person another one based on the prior history.

In one embodiment, the monitoring device 10 features near-by monitoring device 10 recognition that provides for other monitoring device 10 devices to be recognized within a particular vicinity and are able to share and transfer data between them. The monitoring device 10's data analysis and feedback can be based on current or previous sensor output. The monitoring device 10 can alert the user when to charge the monitoring device 10 and when it is the most convenient for the user.

In one embodiment, the monitoring device 10 provides feedback via color change. An outer shell of the monitoring device 10 can use visual feedback, including but not limited to pigment or color changes to indicate changes in user behavior or to prompt changes in user behavior. In one embodiment, the monitoring device 10 is flexible in shape. As a non-limiting example, if the user puts the monitoring device 10 over their hand it can expand or contract, morphing to change size and shape.

In one embodiment, the monitoring device 10 can have a sync feature for multiple bands at the same time.

In one embodiment, the monitoring device 10 has data transfer to an external device that can be included or not included in system 32. Monitoring device 10 could be a data leaching device. For example, the user can relay information to someone else's device (intermediary device) to access Network Systems connected device.

In one embodiment, the monitoring device 10 can disable the recording of one or more sensors 14 based on location, acceleration (or lack thereof) and the like.

In one embodiment, the monitoring device 10 detects different types of transportation and activity based on sensor data. In one embodiment, monitoring device 10 can unlock doors or cars. The user can turn it on and off. As a non-limiting example, it can be turned off by having a capacitor switch on top and bottom and is placed in a way that one couldn't accidentally turn it off. As a non-limiting example, turning it off can be done by rotating the monitoring device 10 once.

In one embodiment, the monitoring device 10 recognizes the wearer based on biometric information, previous data, movement pattern, and the like. In one embodiment, the monitoring device 10 detects a new user based on an inability to match to user/usage patterns.

As non-limiting examples, a variety of different sensors 14 can be used such as, an altimeter, blood oxygen recognition, heart rate from wrist via sonar, Doppler, based on sound wave and movement, based on pressure, and the like. A pressure sensor 14 can be placed on a circulatory vessel such as a vein to detect pulse.

With the monitoring device 10 of the present invention, mechanical actions of the user can be triggered, recognized and evaluated.

As a non-limiting example, with multiple users and wearable devices 10, a separate monitoring device 10 ID is assigned to each of the users A, B AND C, and thereafter the assigned transmitter/monitor 14 generates user activity data and/or user tracking data. For purposes of this disclosure, monitoring data is defined to include data acquired during the process of monitoring or evaluating a predefined characteristic. The user activity data tracks data from the sensors 14 is transferred to the receivers 34 via the wireless connections 38 represented by a dashed line.

A Network System 101 of receivers 34 transfers the user activity and/or tracking data to system server 16 via connection 50. System server 16 includes a processor 52 configured to process the user data in a known manner. For example, the processor 52 may convert raw user data acquired by the sensors 14 into more conveniently readable data.

As a non-limiting example, the display 42 can be implemented to graphically convey user information from system server 16 in a conveniently readable manner. As a non-limiting example, the user may be a cardiac patient with user monitoring data graphically conveyed as a conventional ECG plot comprising a sequence of P-waves, a QRS complexes and a T-waves. As another example, user tracking data may be graphically conveyed as an icon superimposed onto a map to indicate the user's relative location. Alarm 44 may be included in this embodiment.

In some embodiments, system 32 ID circuitry delivers a unique ID to the wearable device from database 18. BLUETOOTH® chips can be coupled with other wearable devices 10 in the area. This data is then stored, as more fully explained in the following paragraph. The unique ID can be utilized for a variety of different applications including but not limited to payments, social networking and the like.

The ID circuitry of system 32 can include a number of system/components: unique ID storage, communication system, which reads and transmits the unique ID from the unique ID storage, battery 24 or power system that provides power to enable communication with the monitoring device 10, a pathway system to route signals to through the circuitry, a cluster that crunches information, and a control system, to orchestrate the communication between different systems. All of these systems can be implemented in hardware, software or a combination thereof. Continuing with the telemetry system 32, sensors 14 and sensing devices are disposed on wearable devices 10 worn by users. Data, such as movement, location, speed, acceleration, and the like, can be acquired, captured and provided to system 32.

System 32 and an associated Network System 101 can include an identification reference, including user activity, performance and reference information for each individual sensor 14 and location.

The user activity, performance metrics, data and the like captured by system 32 can be recorded into standard relational databases SQL server, and/or other formats and can be exported in real-time.

In various embodiments, the monitoring device 10 and/or system 32 are fully sealed and have inductively charges. All communication is done wirelessly.

In one embodiment, there are no electrical contacts, physical contacts or connections with the monitoring device 10. The monitoring device 10 is seamless. The telemetry system 32 can include a microprocessor with CPU 20, memory, interface electronics and conditioning electronics 33 configured to receive a signal from the sensors 14. In one embodiment, all or a portion of the conditioning electronics 33 are at the monitoring device 10.

In one embodiment, the CPU 20 includes a processor 52, which can be a microprocessor, read only memory used to store instructions that the processor may fetch in executing its program, a random access memory (RAM) used by the processor 52 to store information and a master dock. The microprocessor 52 is controlled by the master clock that provides a master timing signal used to sequence the microprocessor 52 through its internal states in its execution of each processed instruction. In one embodiment, the microprocessor 52, and especially the CPU 20, is a low power device, such as CMOS, as is the necessary logic used to implement the processor design. The telemetry system 32 can store information about the user's activity in memory.

This memory may be external to the CPU 20 but can reside in the RAM. The memory may be nonvolatile such as battery backed RAM or electrically erasable programmable read only memory (EEPROM). Signals from the sensors 14 can be in communication with conditioning electronics 33 that with a filter 35, with scale and can determine the presence of certain conditions. This conditioning essentially cleans the signal up for processing by CPU 20 and in some cases pre-processes the information. These signals are then passed to interface electronics, which converts the analog voltage or currents to binary ones and zeroes understood by the CPU 20. The telemetry system 32 can also provide for intelligence in the signal processing, such as achieved by the CPU 20 in evaluating historical data.

In one embodiment, the actions of the user wearing the monitoring device 10 with the unique ID can be used for different activities and can have different classifications at system 32.

The classification can be in response to the user's location, where the user spends it time, with which the user spends its time, determination of working relationships, family relationships, social relationships, and the like. These last few determinations can be based on the time of day, the types of interactions, comparisons of the amount of time with others, the time of day, a frequency of contact with others, the type of contact with others, the location and type of place where the user is at, and the like. These results are stored in database 18.

In one embodiment, the user wearing the monitoring device 10 can access this information from any place where data is presented to the user, including but not limited to mobile devices, the WEB, applications program identifiers, and the like.

As a non-limiting example, the monitoring device 10 communicates with a base station at system 32. The monitoring device 10 can intelligently switch between data transfer and charging based on sensor readout. The monitoring device 10 can represent data based on connected devices.

In one embodiment, the monitoring device 10 has the capability of providing recommendations, popularity of locations or activities based on acquired data from the user.

In one embodiment, the monitoring device 10 has the capability of introducing the user to other people or users based on their data and the user's data.

In one embodiment, the monitoring device 10 can determine emotion of the user.

In one embodiment, the monitoring device 10 uses incremental data transfer via BLUETOOTH® and the like. The monitoring device 10 can transmit data through the inductive coupling for wireless charging. The user is also able to change the frequency of data transmission.

The monitoring device 10 can engage in intelligent switching between incremental and full syncing of data based on available communication routes. As a non-limiting example, this can be via cellular networks, WiFi, BLUETOOTH® and the like. In one embodiment, the monitoring device 10 has data storage. As a non-limiting example, storage of telemetry data on monitoring device 10 can be amounts up to about 16 mg.

In one embodiment, data transferred if it's in a selected proximity of a base station of system 32 or in proximity of an associated connected Network System 101. In one embodiment, the monitoring device 10 has a dynamic change of data capture frequency. The monitoring device 10 can be programmed to instantly change how often it samples any sensor 14 based upon the sensor data. Intelligent data sampling is based on sensor readout.

The monitoring device 10 can receive firmware updates via a base station 110 of system 32. In one embodiment, the monitoring device 10 presents analyzed data and feedback on a website. In one embodiment, the monitoring device 10's software is based on unique human movement. The monitoring device 10 is able to identify its wearer based on the unique patterns of movement, location check-ins and daily habits of the user.

In one embodiment, the app can be used on a mobile device, including but not limited to a smart phone and the like.

In one embodiment, a breakdown of recounting data that has been collecting is presented for analysis of that data. Observation or recommendations can be presented based on historical information and live information. The importance of the data can be based on past user behavior.

In one embodiment, the monitoring device 10 has artificial intelligence. A wearable device processor 54 implements logic resources that exist on monitoring device 10.

In one embodiment, monitoring device 10 engages in the routing of user information to third parties based on pre-defined rules, based on system 32 analyses.

In one embodiment, monitoring device 10 includes one or more processors 54 that implement intelligent algorithmic processing and transfer of information to third parties. Feedback can be provided to the end user that is based on visual, tactile, gesture information and the like.

Figure 4:
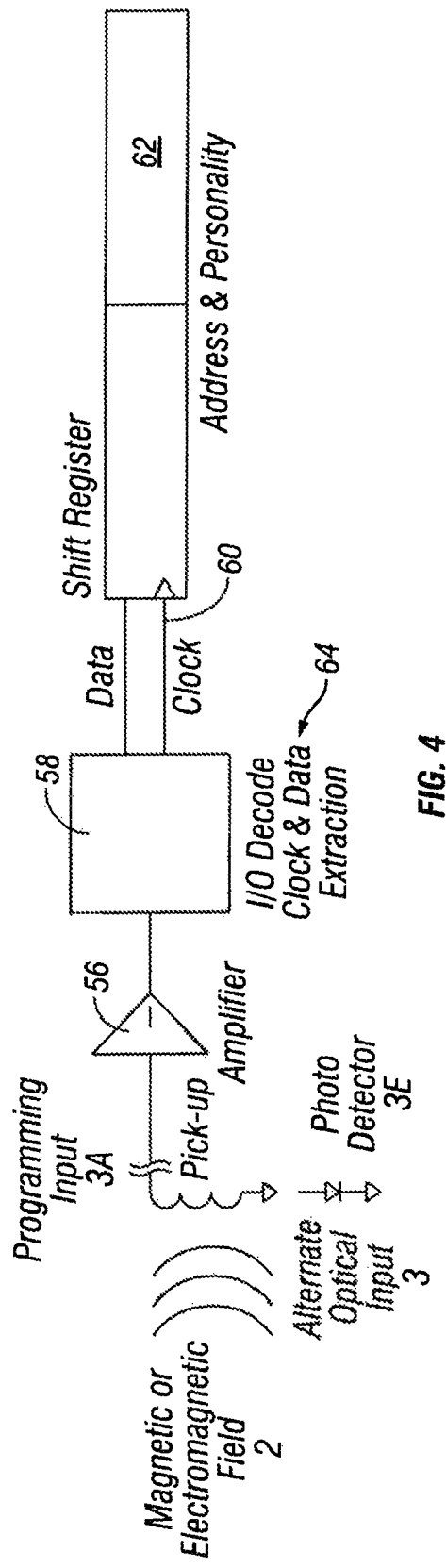
FIG. 4 is a diagram of the programming input schematic of the secure sensor/transmitter array of FIG. 7.

The ID can be sent from the monitoring device 10 in a variety of different transmit modes, which may be provided as part of the firmware or software of an ID or sensor transmitter 14, and which may be utilized selectively during the operation of said sensor transmitter 14, may include "burst" transmit modes, wherein a burst of data information is transmitted, or "parcel" transmit modes, wherein timed data packets of data, which may, as desired, comprise partial data strings, are transmitted, and, if desired, repeated during time intervals. Further, the sensors 14 may have programmed therein diagnostic routines or other test modes which assist during manufacture and use, providing the operator with operational status and verification information on said sensor/transmitter 14, as needed. Referring to FIG. 4, system 32 includes data base 18 which contains the desired transmitter, sensor, 14 personality data, as well as, the address/device ID bits for each monitoring device 10.

In one embodiment, the initial programming of the monitoring device 10 for the ID, as well as optionally other personal information of the user, is done securely, as unauthorized future alteration of same thereafter can be utilized as a means of violating system integrity.

In one embodiment, an inductive field coil is used for programming the sensors 14 and ID of monitoring device 10.

As illustrated in FIG. 4, the monitoring device 10 can include a sensor 14 with an output that be received by an amplifier 56 and decoded by an I/O decoder 58 to determine I/O logic levels, as well as, both clock and data information 60. Many such methods are commonly available including ratio encoding, Manchester encoding, Non-Return to Zero (NRZ) encoding, or the like; alternatively, a UART type approach can be used. Once so converted, clock and data signals containing the information bits are passed to a memory 62. Any of these connections provides a logical link from the system's database 18 to the sensor 14, ID of the monitoring device 10, as shown in FIG. 5.

Figure 5:
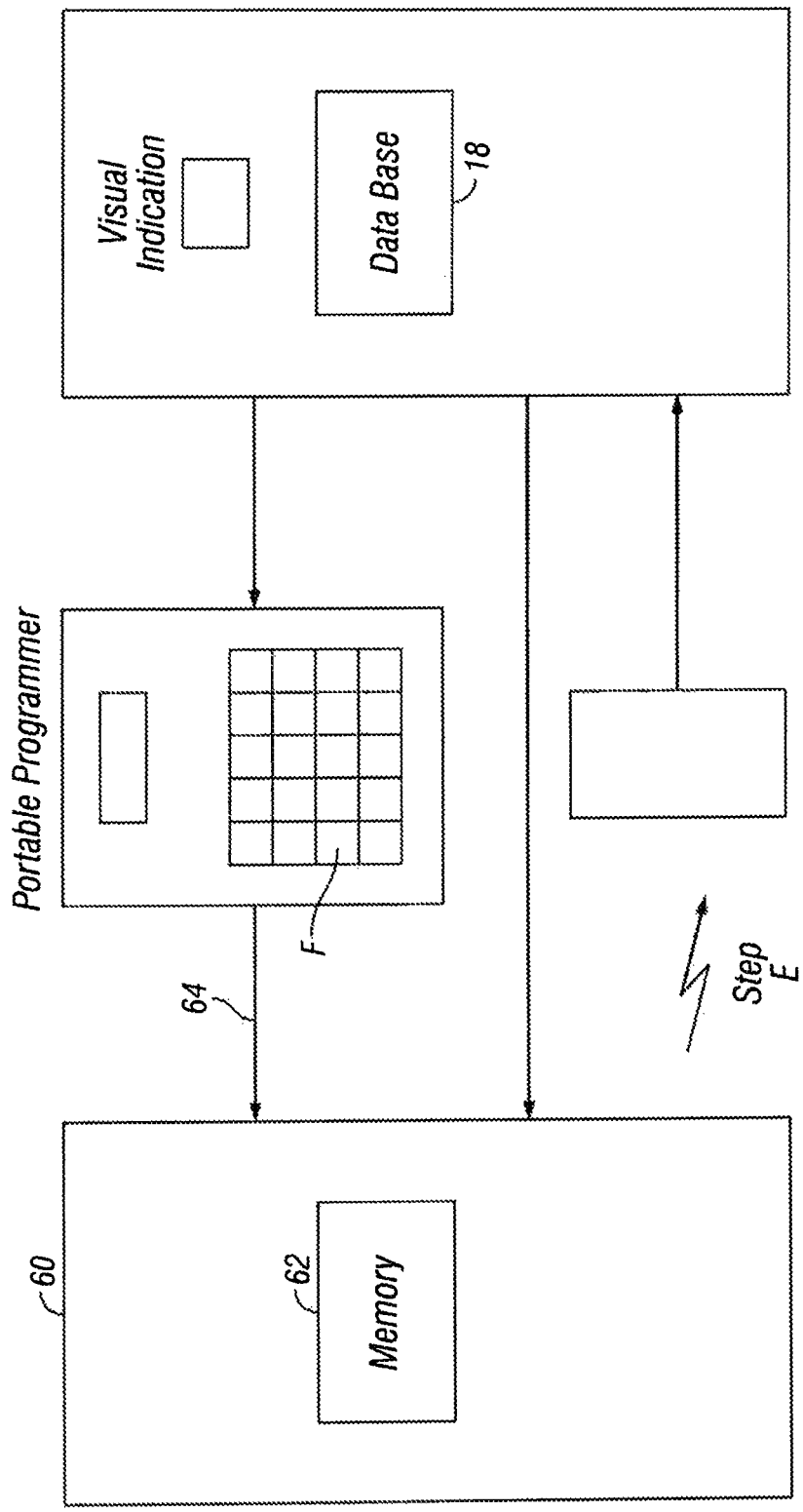
FIG. 5 is a block diagram of the system of programming the sensor/transmitter(s) comprising the secure sensor/transmitter array of FIG. 7.

In one embodiment, illustrated in FIG. 5, the system 32 chooses the necessary programmable sensor functions and stores them into database 18. In one embodiment, in order to insure that an unauthorized user cannot connect into and program monitoring device 10 the following procedure may be used:

Both the sensor 14 and receiver 34 contain an identical, repeatable pseudo randomization algorithm in ROM or in ASIC logic.

Figure 6:
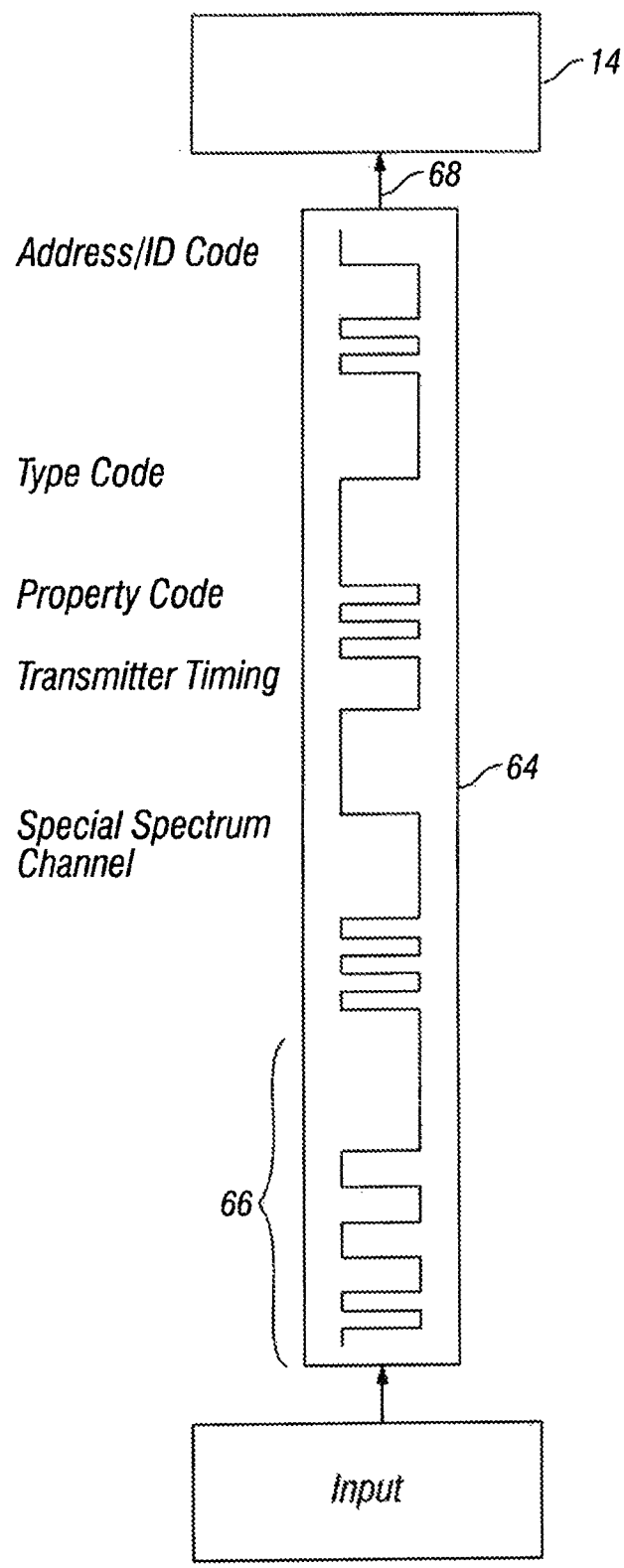
FIG. 6 is a block diagram of the jam command and security/randomization bits of the secure sensor/transmitter array of FIG. 7.

Referring to FIG. 6, the algorithm is applied to outgoing programming data 64 from system 32 and produces a number of security/randomization bits 66 that can be appended to the outgoing programming message or message 68 and sent to a sensor 14.

Figure 7:
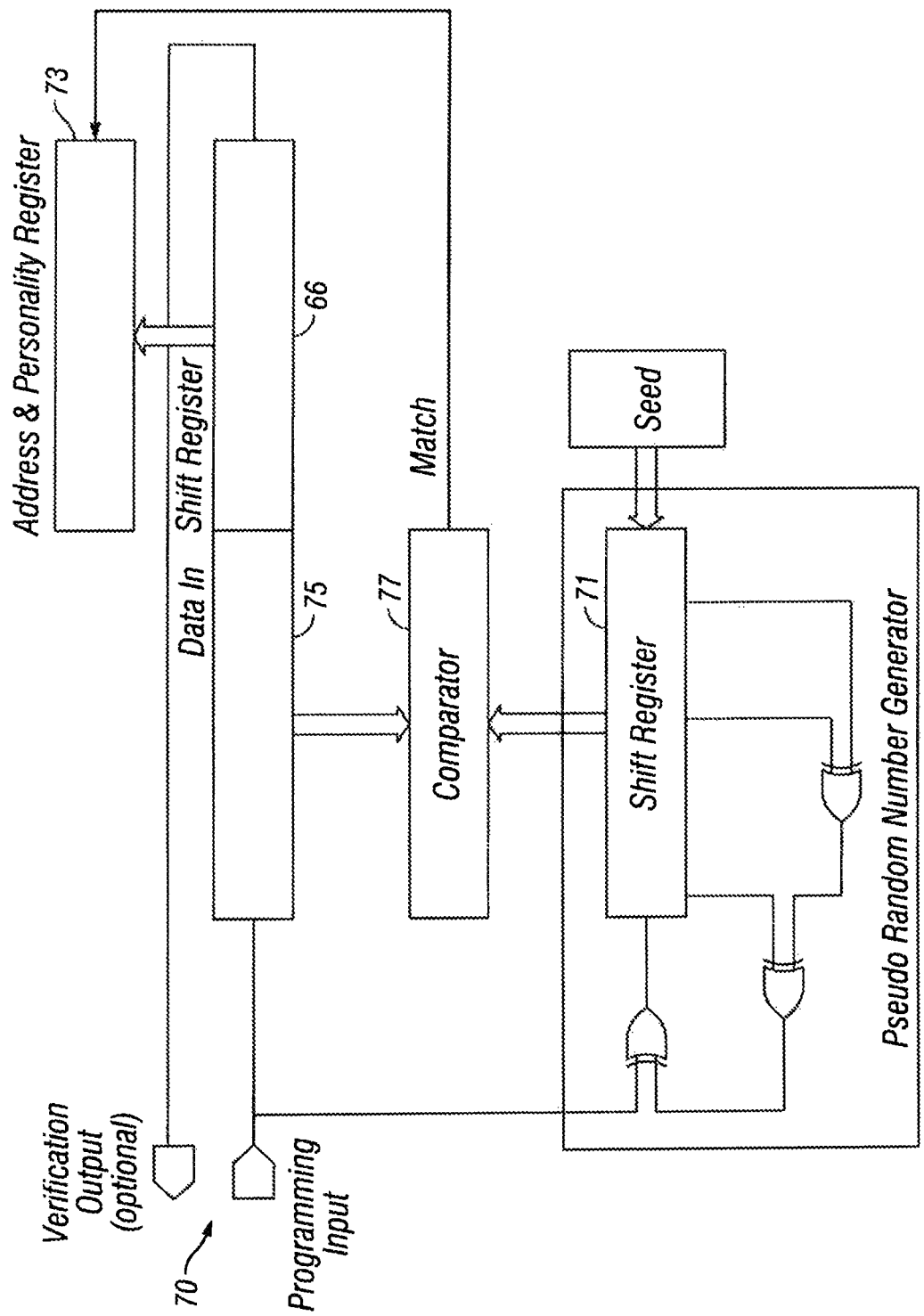
FIG. 7 is a logic circuit diagram of the sensor/transmitter programming input schematic in one embodiment of the present invention.

Referring to FIG. 7 the sensor 14 likewise applies this pseudo randomization algorithm as the security/randomization bits 66 to the outgoing programming data, now forming the incoming programming data 70 to sensor 14 and produces a several bit result in the shift register 71. The scrambling algorithm is devised such that a small difference in the programming bit stream causes a great difference in the pseudo randomization result. As a non-limiting example, the present invention can use a 16 bit polynomial to produce this pseudo randomization.

Optionally, in one embodiment, before a sensor 14 accepts this programming, stored in an address and personality register 73, both the pseudo random code, stored in data in a shift register 75 from system 32 and a sensor 14, in a shift register 71 must match via a comparator ID, 77, indicating unauthorized acceptance use. In addition to insuring authorized access, this process also insures that the data itself is correct. The longer the polynomial sequence used, the greater the security.

In one embodiment, spread spectrum or other RF transmission is used and can include programming to determine that the frequency or spread spectrum code is unique to the area. If a spread spectrum code, system code, or frequency channel is found to be occupied at a future time of use. Re-programming of the monitoring device 10 is then done with a new, unused spread spectrum code or system code or frequency channel can be selected, or, in the alternative, CPU 20.

As illustrated in FIG. 5, step "E" would include, for example, the step of the sensor 14, inputting the programming message and saving a seed in memory 62; with the sensor 14 utilizing the seed to code digital data bits transmitted.

Figure 8:
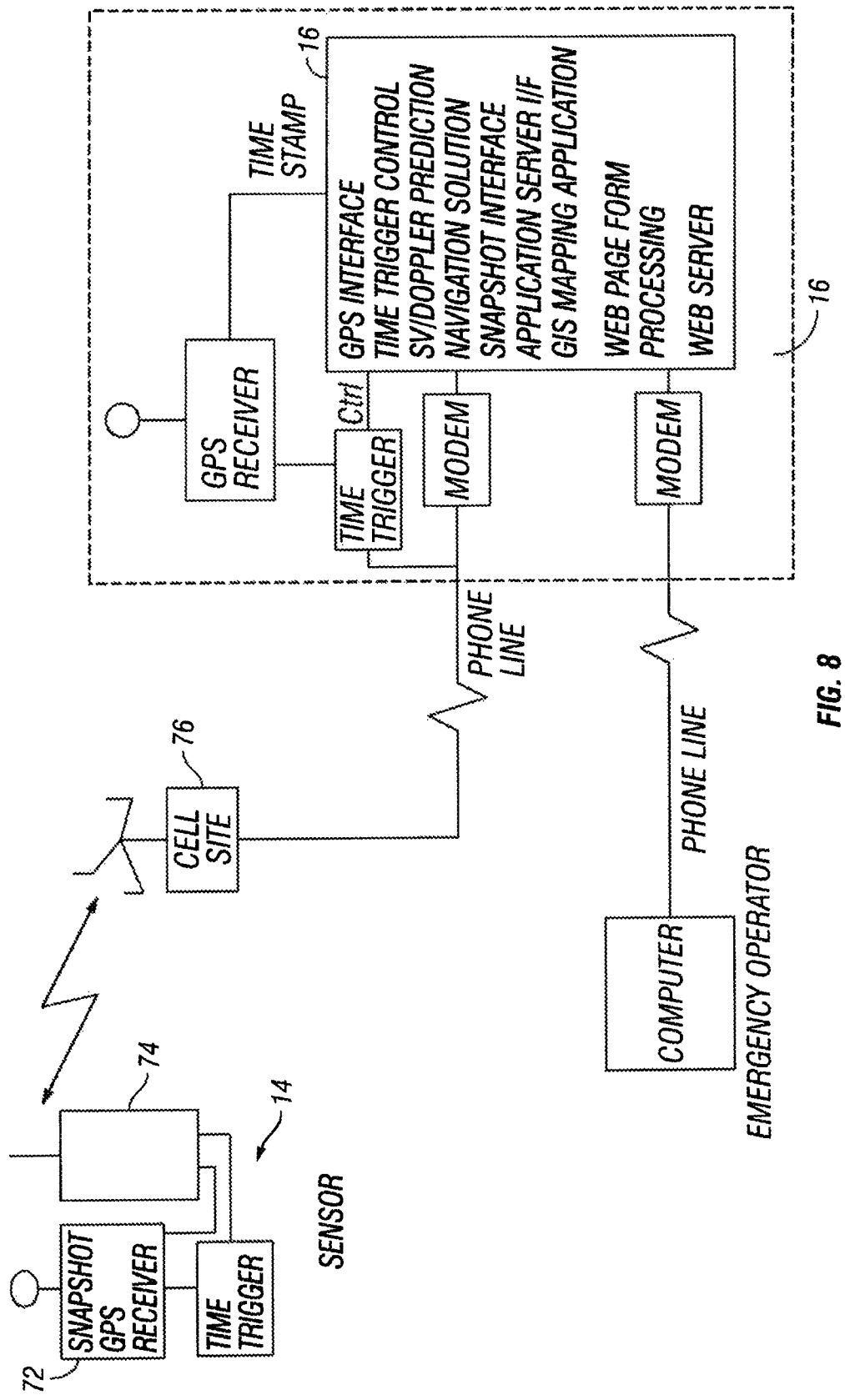
FIG. 8 is a block diagram of an embodiment of a computer implemented system for determining the location of a remote sensor utilizing the methods of the present invention.

As illustrated in FIG. 8, the location of a monitoring device 10 with the ID and sensors 14 can be determined. As a non-limiting example, in one embodiment the monitoring device 10 includes a sensor 14 that can provide a position signal having positioning data (e.g., raw GPD data or pseudo ranges) and the ID is transmitted from the monitoring device 10 to system server 16. Server 16 receives the position signal and analyzes the signal to generate information representing the location of the monitoring device 10. Server 16 transmits this location information to a client computer where the location of the monitoring device 10, allowing a user to identify the location of the remote sensor 14.

In one embodiment, the position signal transmitted by the remote sensor 14 can also include an emergency code. For example, in the event of an emergency, such as a medical emergency or otherwise, a user may press a "panic button" that can be on the monitoring device 10 or by use of a user's mobile device. Pressing the panic button may cause mobile device 74 to transmit an emergency signal to a cell site 76 where the emergency signal is relayed to server 16. In response, server 16 can transmit Doppler information regarding in-view satellites, a fix command and a time trigger signal to the monitoring device 10.

When the location of the monitoring device 10 has been determined, software running on server 16 configures server 16 such that a call or other signal is sent to a local emergency operator in the vicinity of remote sensor 14. When the call or signal is received at the emergency operator station, the location of remote sensor 14 is transmitted and displayed. In some cases, where separate panic buttons are available for identifying medical, police, fire or other types of emergencies, the nature of the emergency is also displayed for the emergency operator. Based on this information, the emergency operator can initiate an emergency response by providing the location of remote sensor 14 to the required emergency service (police, fire department, ambulance service, etc.). In other embodiments, instead of or in addition to a position report for the remote sensor 14, the emergency operator may also be provided with information which identifies an emergency response vehicle in close proximity to remote sensor 14.

Figure 9:
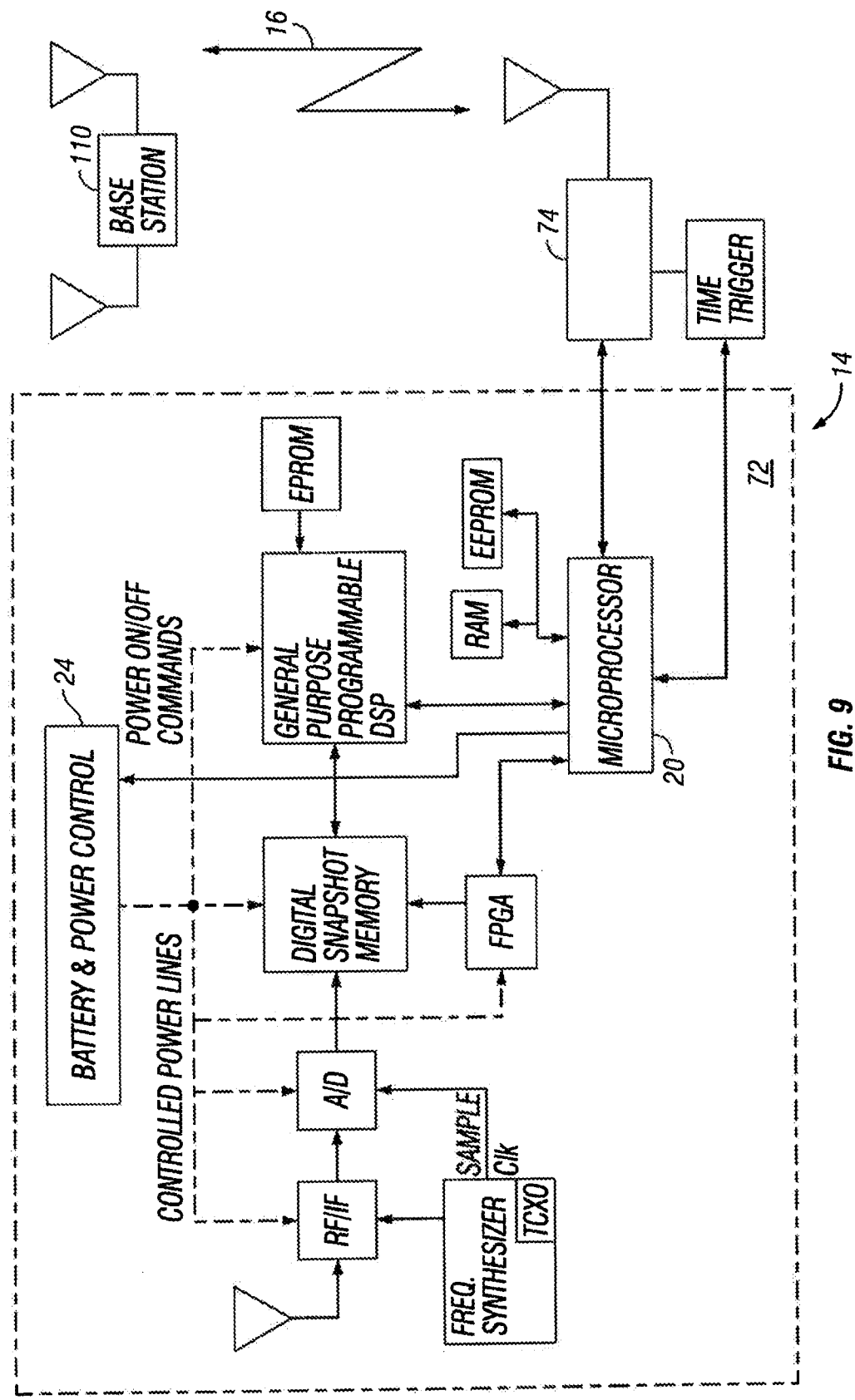
FIG. 9 is a block diagram illustrating one embodiment of a SNAPSHOT GPS receiver for use according to the present invention.

As illustrated in FIG. 9, a sensor 14 of the monitoring device 10 can include a SNAPSHOT GPS receiver 72. As described above, sensor 14 uses information transmitted from separately located base station 110, mobile devices, computers, and other devices, to assist in determining the position of the remote sensor 14, as more fully disclosed in U.S. Pat. No. 6,661,372, incorporated herein by reference.

Figure 10:
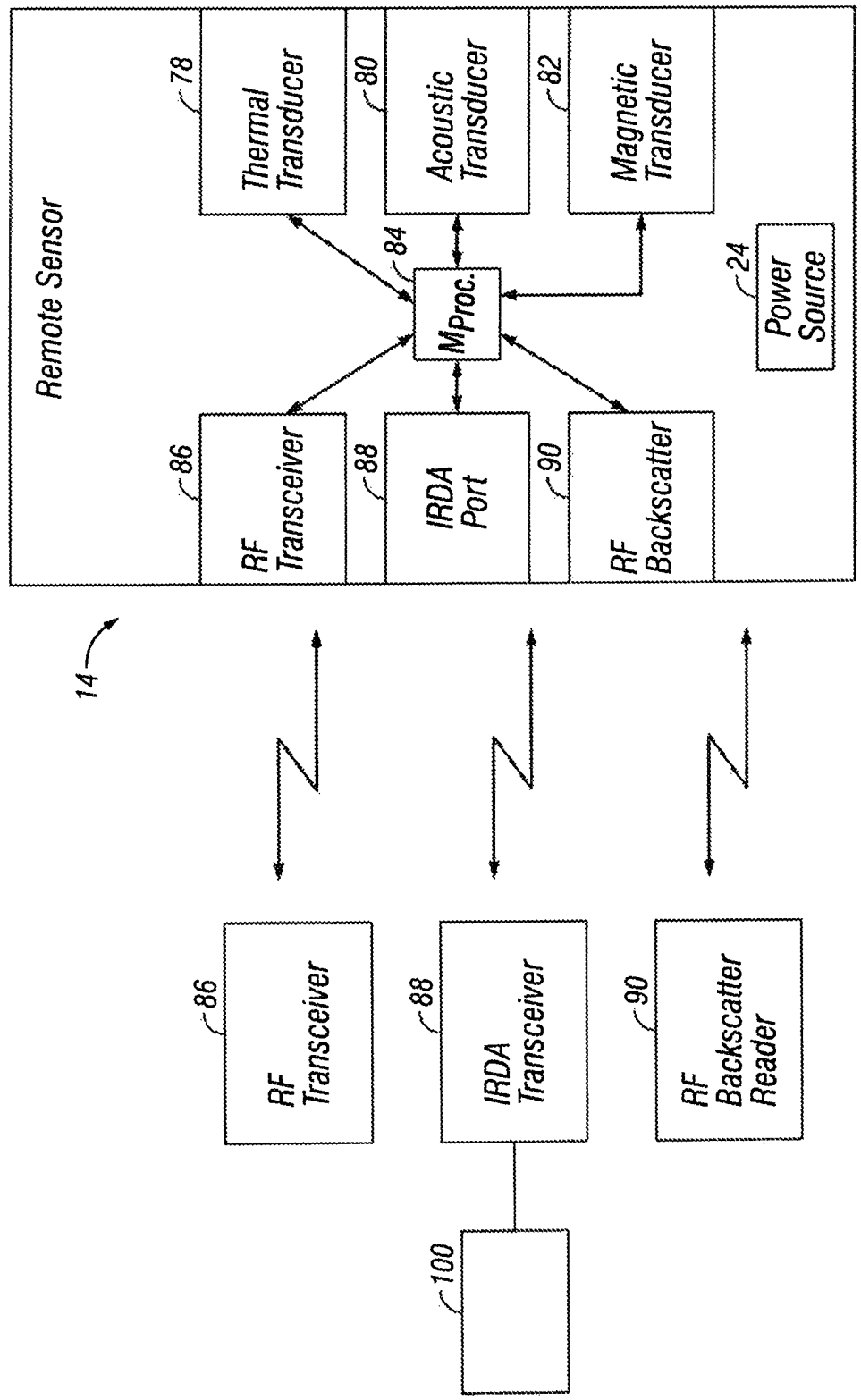
FIG. 10 is a block diagram of a remote sensor shown in communication with two different external communication devices.

As non-limiting examples, and as illustrated in FIG. 10, the sensors 14 can be a thermal transducer 78, an acoustic transducer 80, and a magnetic transducer 82. It will be appreciated that the present invention is not limited. The transducers 78, 80, and 82 in the monitoring device 10 can communicate with a microprocessor 84 also located in the monitoring device 10. The monitoring device 10 can communicate with other devices via an RF transceiver 86, an IRDA transceiver 88, and/or an RF backscatter transceiver 90. Each of the components in the monitoring device 10 receives power as necessary from the battery 24, which may include the rechargeable battery.

The acoustic transducer 80 may include a microphone, a low-pass filter, a gain amplifier, and a threshold comparator. The acoustic transducer 80 may include an omnidirectional microphone, although any other suitable acoustic transducer device would suffice. The microphone may be a surface mount MEMS device that has a frequency range of 100 Hz to 10 kHz. A single MCP602 operational amplifier is used on the acoustic sensor to amplify and low-pass filter the acoustic signal from the microphone. Another operational amplifier is used to generate a voltage reference used for single biasing and detection. The microphone output is biased to the midway point between the circuit supply voltage and ground to allow for both positive and negative signal swings. The biased signal is filtered with a second order low-pass Butterworth filter to remove upper frequency noise. It is then amplified with an adjustable gain that is controlled by a digital resistor potentiometer. This digital resistor operates on an I2C bus and is controlled by the microprocessor 84. Lastly, the amplified acoustic signal is threshold detected against a static voltage to detect sufficiently large acoustic signals. The digital output of the threshold detector is connected to the microprocessor 84 for processing.

The magnetic transducer 82 can include a magnetic sensor integrated circuit, a differential instrumentation amplifier, a low-pass filter, two gain amplifiers, and a threshold detector. The magnetic transducer 82 may include an NVE AA002-02 GMR (giant magneto resistive) field sensor, although any suitable magnetic sensor would suffice. This sensor has a saturation field of 15 Oe, a linear range of 0 to 10.5 Oe, and a sensitivity of 3 mV/V/Oe. Two MCP602 CMOS operational amplifiers are used on the magnetic sensor to amplify and low-pass filter the analog output signal. An INA122UA instrumentation amplifier is used as a difference amplifier for the differential output from the magnetic sensor. The magnetic sensor IC can be based on Spintronics technology. Its output includes a differential voltage pair proportional to the detected magnetic field. The differential voltage pair is amplified and converted to a single voltage by the instrumentation amplifier. The AC-coupled signal is then amplified and filtered with a low-pass filter to remove upper frequency noise and boost the low-voltage signal output. The signal is amplified a second time by an adjustable gain controlled by a digital resistor similar to the acoustic sensor. Lastly, the amplified magnetic signal is threshold detected against a static voltage, to detect sufficiently large changes in magnetic fields. The digital output of the threshold detector can be connected to the microprocessor 84 for processing.

A DS1803E-010 digitally controlled 10 kOhm variable resistor can be used in both the acoustic and magnetic sensor circuits. It is used to adjust the gain of one gain stage in each circuit. The digital resistor is controlled through an I2C interface. A LMV3931PWR comparator is also used in both the magnetic and acoustic sensor circuits for determining when a sufficiently strong sensor signal has been detected. It compares the analog sensor signal against the voltage reference and its output is tied to the microprocessor 84 for data collection.

The thermal transducer 78 may include a Burr Brown TMP 100NA/250 12-bit digital temperature sensor, although any suitable thermal sensor would suffice. The digital temperature sensor has an operating range of −55 to +120.degree. C., an accuracy of 0.5.degree. C. and a maximum resolution of 0.0625.degree. C.

Even though it is a 12-bit sensor, suitable results are achieved with only 9-bit conversions with only the 8 most significant bits used. The sensor has an I2C interface and is normally kept in sleep mode for low power operation. When directed by the microprocessor 84, the thermal transducer can perform a 9-bit temperature conversion in 75 milliseconds.

Figure 11:
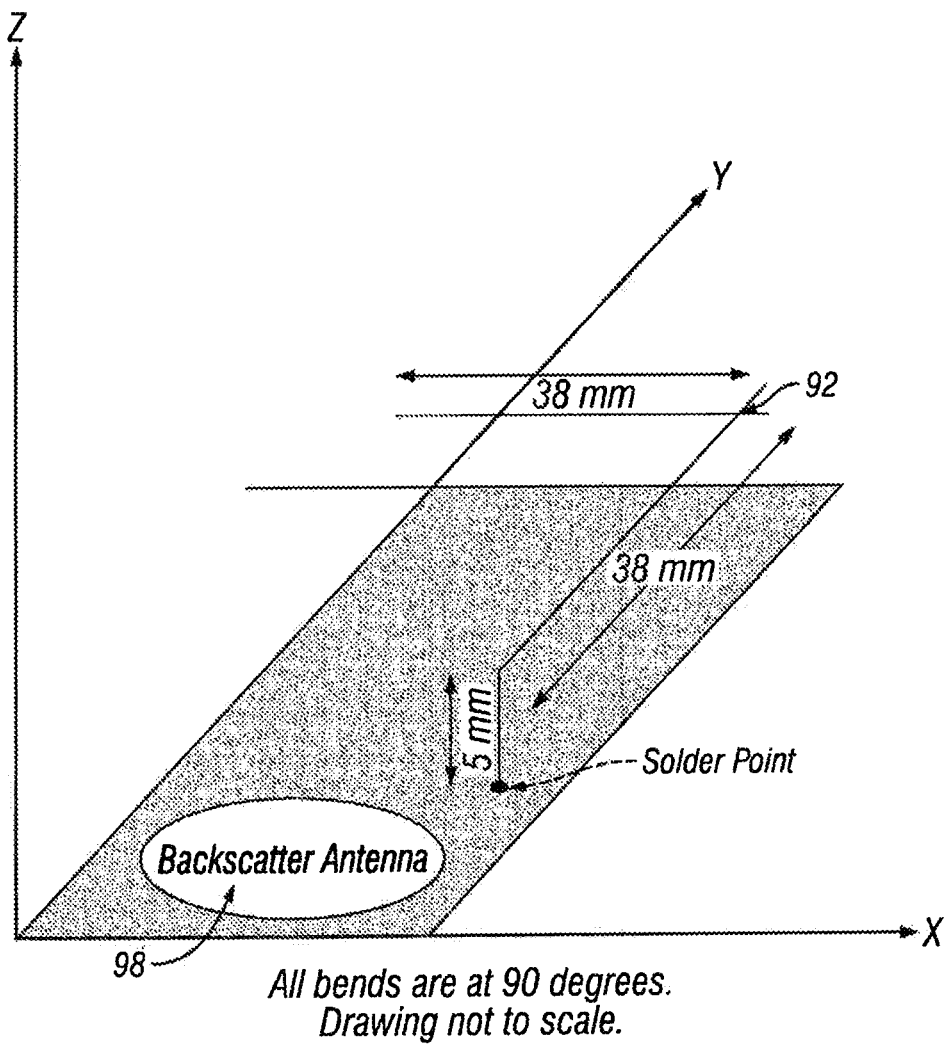
FIG. 11 is a diagram of the active RF and RF backscatter antennas.

The RF transceiver 86 may include an RF Monolithic DR3000 transceiver, although any suitable transceiver or separate transmitter and receiver 34 would suffice. This transceiver 86 allows for both digital transmission and reception. The transceiver 86 can have an operating frequency of 916.5 MHz and is capable of baud rates between 2.4 kbps and 19.2 kbps. It can use OOK modulation and has an output power of 0.75 mW. It also can use digital inputs and outputs for direct connection with the microprocessor 84. The transceiver 86 can use an antenna 92 (FIG. 11) that may include a 17 mil thick plain steel electric guitar G-string cut to a length of 8.18 cm. It is used in a monopole over ground configuration and can require a matching circuit of one inductor and one capacitor. Alternatively, Frequency Shift Keying (FSK), Quadrature Phase Shift Keying (QPSK), or any other suitable modulation scheme may be utilized.

The IRDA transceiver 88 may include a Sharp GP2W0110YPS infrared transceiver, although any suitable IRDA compliant infrared transceiver would suffice. This transceiver 88 can be IRDA v1.2 compliant and in one embodiment has an operating range of 0.7 meters. In one embodiment, it is capable of 115.2 kbps data speeds.

The RF backscatter transmission device 90 may include circuitry available from Alien Technology (of Morgan Hill, Calif.) for receiving and transmitting signals via RF backscatter. Battery 24 may be a 3.6 volt ½ AA lithium battery with a capacity of 1.2 amp hours. The battery 24 can be a power source 24 that can include a Texas Instruments TPS76930 DBVT voltage regulator to regulate the output signal to 3 volts and with a maximum current of 100 mA. The voltage regulator can include a LDO.

The RF backscatter transceiver 86 in the monitoring device 10 communicates with an RF backscatter reader 94 such as a class 3 reader from Alien Technology. The reader 94 transmits data to the backscatter transceiver 90 of the monitoring device 10 by broadcasting encoded RF pulses and receives data back from the transceiver 86 by continually broadcasting RF energy to the sensor 10 and monitoring the modulated RF reflections from the sensor 10.

The RF backscatter transceiver 90 can include a printed circuit board (PCB) patch antenna for RF reception, and RF modulation, a Schotky diode detector circuit, a comparator circuit for signal decoding, and a logic circuit for wake-up. The logic circuit monitors the incoming data, and when an appropriate wake-up pattern is detected, it triggers the microprocessor 84 so that data reception can begin. In one embodiment, the reader 94 has an operating frequency between 2402 MHz and 2480 MHz, and uses frequency hopping in this band to reduce noise interference. A modulation method used by the reader 94 can be On-Off Keying (OOK). In one embodiment, the transmission power is 1 watt. The operation of the reader 94 may be controlled by an external computer (not shown) as directed by Labview software via a RS-232 serial link.

The RF transceiver 86 can communicate with an external RF transceiver 96 such as a DR3000 transceiver from Radio Monolithics, Inc. In one embodiment, it operates at 916.5 MHz, uses OOK modulation, has a communication range of 100 meters line of sight, and a baud rate of 19.2 kbps. The active RF antenna 92 can be a quarter-wavelength monopole made from a guitar G-string and appropriate matching circuitry. Two control lines from the microprocessor 84 can be used to select the mode of operation, choosing from transmit, receive, and sleep. The active RF receiver 34 consumes the most power in receive mode compared to the other two communication links.

FIG. 6 shows the relative positioning and shape of the active RF antenna 92 and the RF backscatter antenna 98.

The IRDA transceiver 88 of the monitoring device 10 can communicate with an external IRDA transceiver 100 that may be identical to the IRDA transceiver 88. Alternatively, the IRDA transceiver 100 can be one such as is provided in most personal digital assistants (PDA) as well as many other consumer devices. The IRDA communication link follows the standard IRDA signal and coding protocol and is modeled after a standard UART interface. In one embodiment, the IRDA transceiver 88 is capable of data speeds less than 115.2 kbps, and may only have a range of 0.7 meters for transmission. One advantage of the IRDA communication link is that it does not require any of the RF spectrums for operation, but it typically does require line-of-sight communication.

When any one of the transceivers 86, 88 and 90 on the monitoring device 10 detect the beginning of valid data on their respective communication link, all other transceivers are disabled, thereby preventing the corruption of incoming data with the noise or partial data packets on the other communication links. However, if the data on the active transceiver proves to be erroneous, the other transceivers will be re-enabled if appropriate to allow normal operation to continue. If the data received by the active transceiver is valid, however, the other transceivers will remain disabled for several hundred milliseconds longer in the high probability that the next data packet will be transmitted on the same communication link. If, after this extended delay, no additional packets are received, then the other transceivers will be re-enabled as appropriate.

In one embodiment, the active RF protocol has no wake-up or synchronization packets, and the packets sent to and from the sensor are identical. In one embodiment, the format of an active RF packet is shown in FIG. 2. It can include a preamble to reset and spin-up the state machine of the RF receiver 34 and to properly bias the receiver's 34 data slicer/threshold detector for optimum noise rejection and signal regeneration, two framing bits to indicate the beginning and end of the data bytes, and the data bytes themselves.

Figure 12:
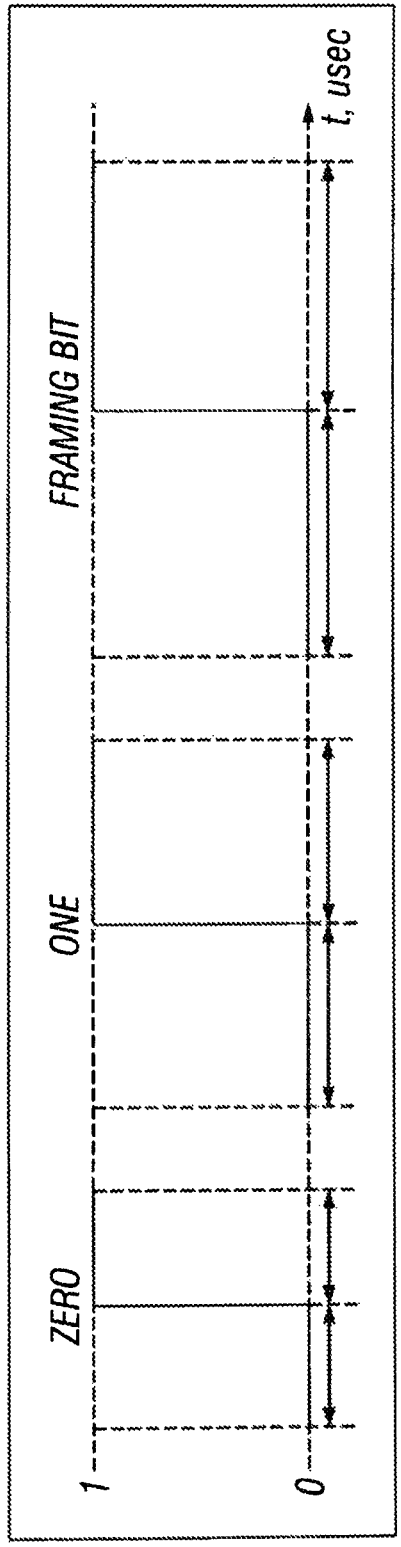
FIG. 12 is a diagram of the encoding scheme for the symbols in the active RF protocol.

Furthermore, the encoding scheme for the three symbols is shown in FIG. 12. The entire packet is DC balanced to maintain an optimal level on the data slicer/threshold detector and the receiver 34. Data is sent most significant bit first.

Figure 13:
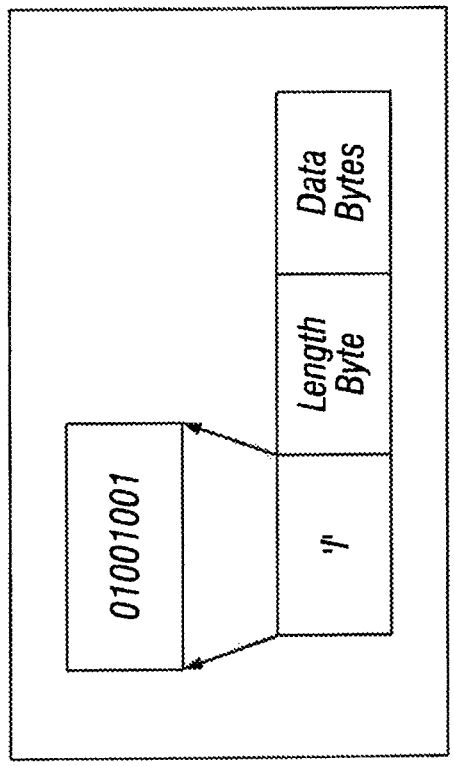
FIG. 13 is a diagram of the packet structure in the IRDA protocol.
Figure 14:
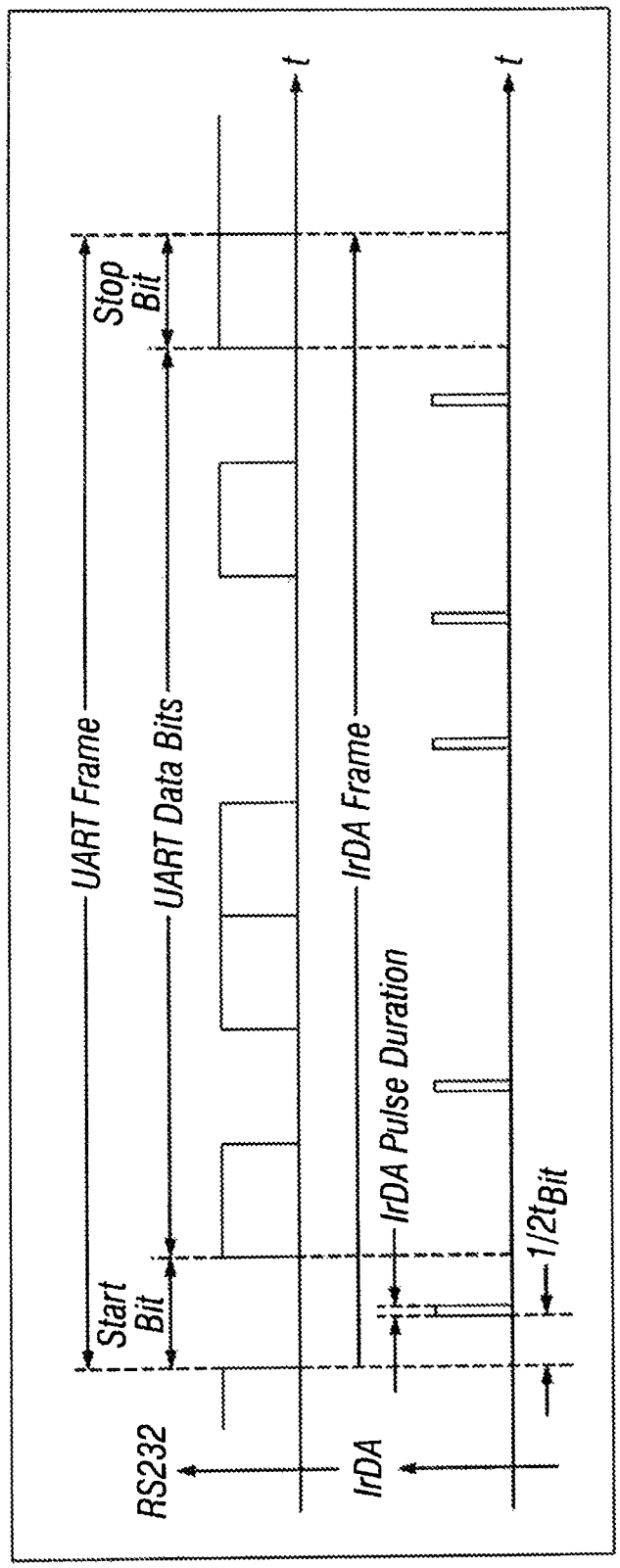
FIG. 14 is a diagram of the encoding scheme in the IRDA protocol.

The IRDA communication link can follow the standard IRDA protocol for bit encoding and UART protocol for byte transmission. Packets transmitted on the IRDA link can contain no preamble or framing bits, but they do have a header that contains two bytes. The first byte is an ASCII "I" which denotes the beginning of a valid IRDA packet. The second byte equals the number of preceding bytes in the packet. This value is used by the receiver 34 to determine when the entire packet has been received and processing of information can begin. The packet structure is shown in FIG. 13 and the IRDA/UART encoding scheme is shown in FIG. 14.

The data bytes contained in a packet transmitted to the sensor 10 through any of the communication links conform to a packet format. The CMD section of a packet is a single byte that identifies the type of packet being sent. The CMD byte appears above the beginning and end of the packet and the two must be identical. The reason for including the redundant byte is to further eliminate the chance of a packet's CMD identifier being corrupted at the receiver 34, even if the CHECKSUM is correct.

The PAYLOAD contains all of the data that must be sent to, or returned from, the sensor. The PAYLOAD is broken down into individual bytes with the overall number of bytes and their content dependent on the type of packet being sent.

The CHECKSUM is a 16-bit CRC that is performed on all bytes in the data packet excluding the end CMD byte in packets generated by the external device. The CHECKSUM is sent most significant byte first.

The transceivers 86, 88 and 90 may be required to communicate over a greater distance than do the components described herein. Upgrading these components to be suitable for longer distance transmission is considered to be within the spirit of this invention. The type of transducer is not limited to the specific transducer types described herein. In addition, the logic described herein for arbitrating between which communication device to use to communicate with the outside world and which sensor data to provide at what time is but one possible approach to arbitration logic within such a remote sensor 10.

Figure 15:
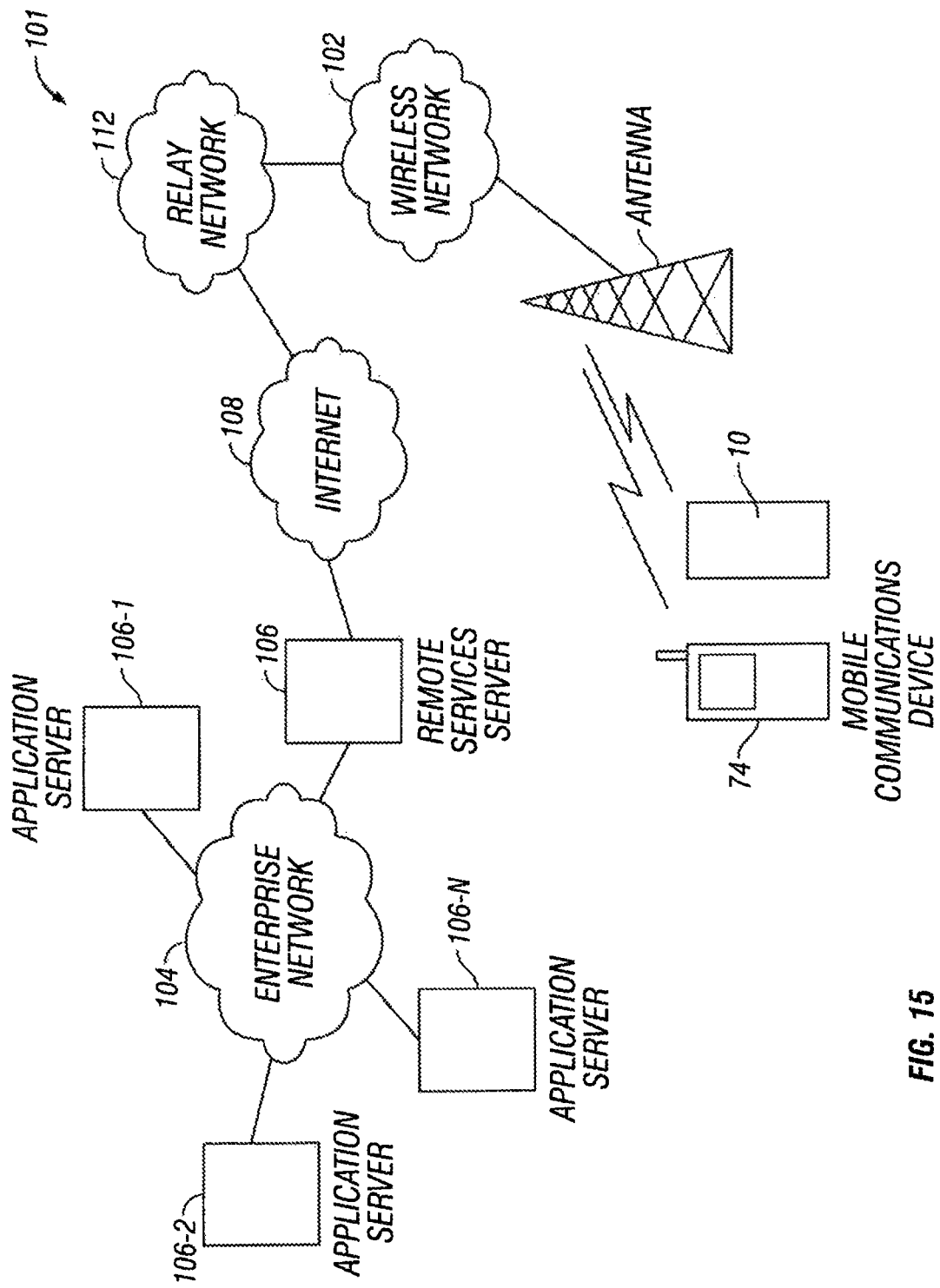
FIG. 15 illustrates one embodiment of a wireless network that can be used with the present invention.
Figure 16A:
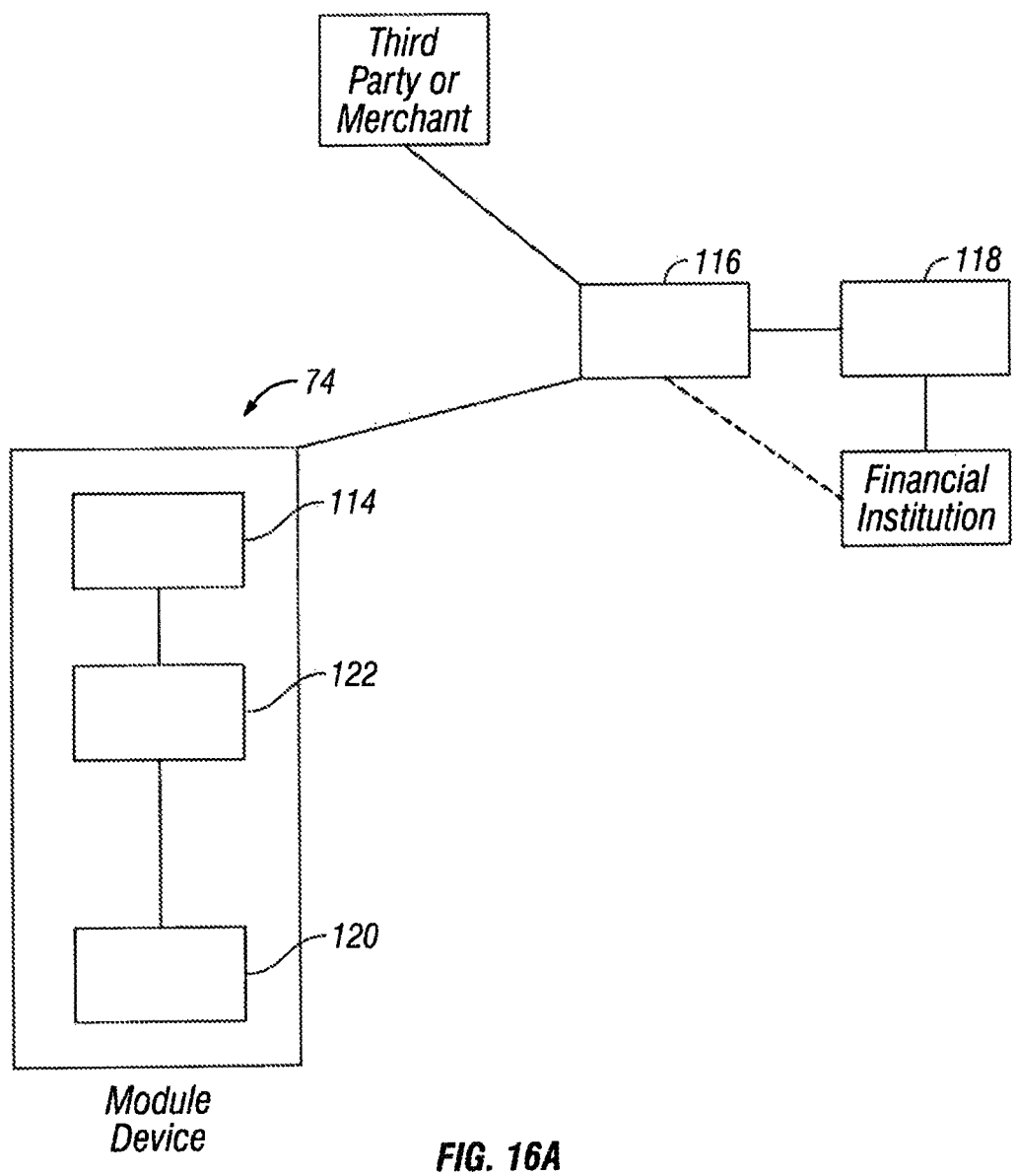
FIGS. 16(a)-16(d) illustrate various embodiments of the interaction of a wearable device of the present invention with an interaction engine, a transaction engine, a decoding engine, and a payment system and a third party.
Figure 16B:
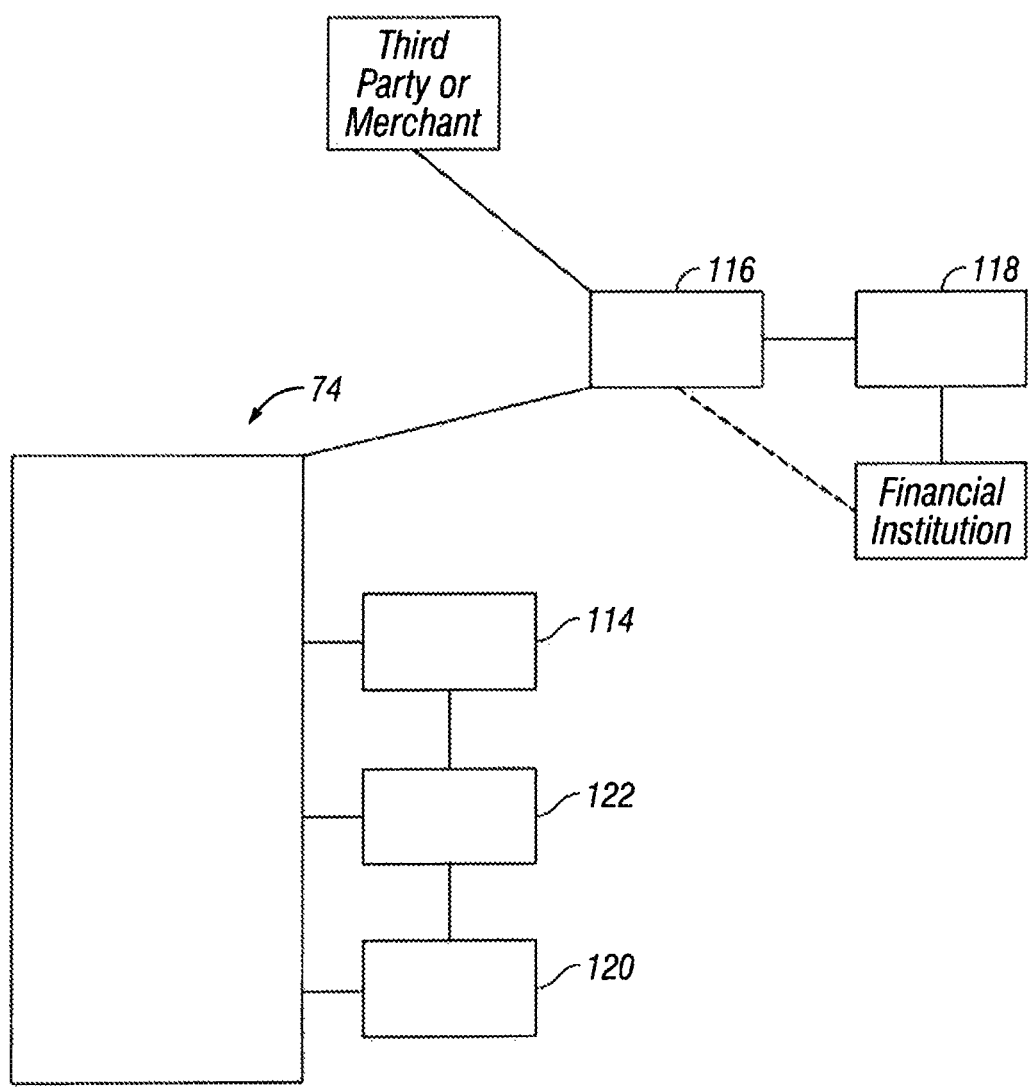
Figure 16C:
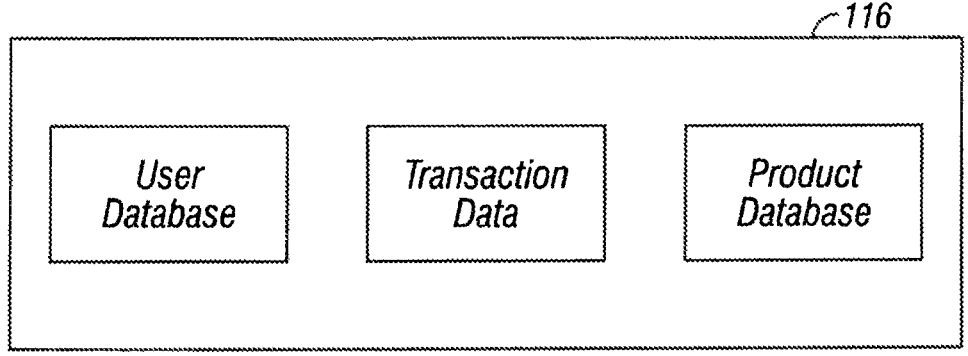
Figure 16D:
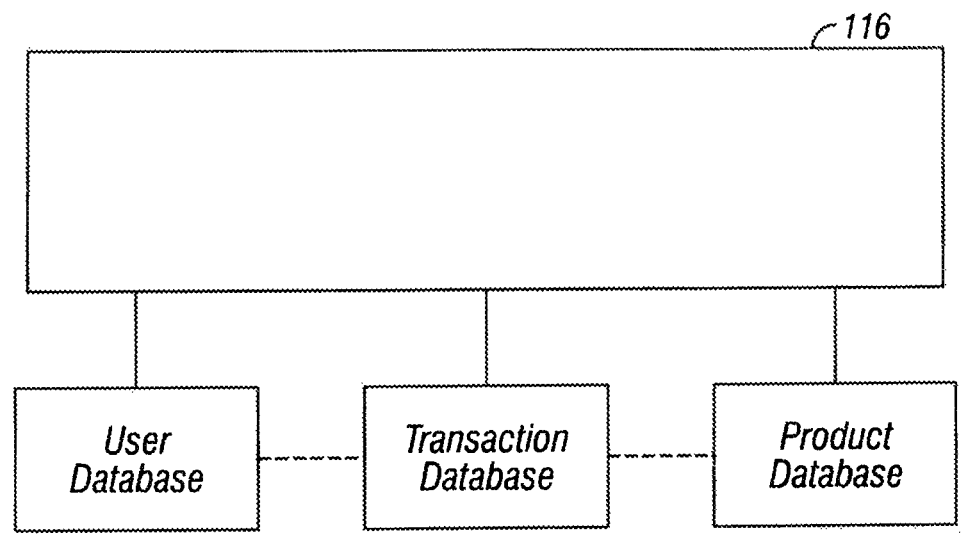

FIG. 15 illustrates one embodiment of an exemplary Network System 101 that can be used with the present invention. As shown in FIG. 15 a wireless packet data service Network System 102 that can be utilized with the monitoring device 10. An enterprise Network System 104, which may be a packet-switched network, can include one or more geographic sites and be organized as a local area network (LAN), wide area network (WAN) or metropolitan area network (MAN), and the like. One or more application servers 106-1 through 106-N can be included and disposed as part of the enterprise network 104 are operable to provide or effectuate a host of internal and external services such as email, video mail, Network Systems 101 access, corporate data access, messaging, calendaring and scheduling, information management, and the like using the unique IDs of the wearable devices 10. The monitoring device 10 can be in communication with a variety of personal information devices other than the monitoring device 10, including but not limited to, computers, laptop computers, mobile devices, and the like.

Additionally, system server 16 may be interfaced with the enterprise Network System 104 to access or effectuate any of the services from a remote location using a monitoring device 10. A secure communication link with end-to-end encryption may be established that is mediated through an external IP network, i.e., a public packet-switched network such as Network Systems 108, as well as the wireless packet data service Network System 102 operable with a monitoring device 10 via suitable wireless Network System 101 infrastructure that includes a base station (BS) 110. In one embodiment, a trusted relay Network System 101 112 may be disposed between Network Systems 108 and the infrastructure of wireless packet data service Network System 102.

In another embodiment, the infrastructure of the trusted relay network 112 may be integrated with the wireless packet data service network 102, and the functionality of the relay infrastructure can be consolidated as a separate layer within a "one-network" environment. Additionally, as non-limiting examples, monitoring device 10 may be capable of receiving and sending messages, web browsing, interfacing with corporate application servers, and the like, regardless of the relationship between the networks 102 and 112. Accordingly, a "network node" may include both relay functionality and wireless network infrastructure functionality in some exemplary implementations.

In one embodiment, the wireless packet data service Network System 102 is implemented in any known or heretofore unknown communications technologies and network protocols, as long as a packet-switched data service is available therein for transmitting packetized information. For instance, the wireless packet data service Network System 102 may be comprised of a General Packet Radio Service (GPRS) network that provides a packet radio access for mobile devices using the cellular infrastructure of a Global System for Mobile Communications (GSM)-based carrier network. In other implementations, the wireless packet data service Network System 102 may comprise an Enhanced Data Rates for GSM Evolution (EDGE) network, an Integrated Digital Enhanced Network (IDEN), a Code Division Multiple Access (CDMA) network, a Universal Mobile Telecommunications System (UMTS) network, or any 3rd Generation (3G) network.

Referring now to FIGS. 16(*a*) through 16(*d*), in one embodiment, the monitoring device 10 is in communication with an interaction engine 120 that can be at a mobile device 74 or system 32. The interface engine can be a software application running on mobile device 74 associated with another party, including but not limited to a merchant, an associate, a friend, and the like. The enables the monitoring device 10 user and a merchant to interact with a transaction engine 114 to and enter into a financial transaction for the transfer of funds from a third party payment system 116 that is independent of the monitoring device 10 user's financial account 118, and complete a transaction. It should be noted that the payment system 116 can be affiliated with the financial account 118 or can be a separate and non-affiliated with the financial account 118. The interaction engine 120 can take input of information related to a transfer of funds from the monitoring device 10 users' financial accounts 118 as input to the transaction engine 114 to initiate and complete a financial transaction, including but not limited the purchase and payment of goods and services. In one embodiment, this input to the interaction engine 114 can include, an amount of a transaction, additional items related to the transaction, authorization and/or signature of the monitoring device 10 users.

In one embodiment, the mobile device 74 receives information from the monitoring device 10, e.g., the unique ID.

The interaction engine 120 can also present products or services provided by a merchant to directly to or through system 32 to the monitoring device 10 user. In one embodiment, the monitoring device 10 users can use the mobile device 74, the WEB, and the like, to view, text, pictures, audio, and videos, and browse through the products and services on the mobile device 74, personal computers, other communication devices, the WEB, and anything that is BLUETOOTH®, anything associated with Network Systems 101, and the like.

In one embodiment, the transaction engine 114, which can be at the mobile device 74, or external to the mobile device 74, including but not limited to monitoring device 10 and the like, takes decoded financial transaction card information from a decoding engine 122, internal or external to the mobile device 74, and a transaction amount from an interaction engine 120, also internal or external to the mobile device. The transaction engine 114 then contacts the payment service 116, and or the monitoring device 10 users' financial account 118, such as an acquiring bank that handles such authorization request, directly or through the payment system 116, which may then communicate with a financial transaction card issuing bank to either authorize or deny the transaction. The payment system 116 can include a user database, a transaction database, a product database, and the like. These databases can also be external to payment system 116. If the third party authorizes the transaction, then the transaction engine 114 transfers funds deducted from the account of the monitoring device 10 user, or the payment system 116 can already have those funds readily available, to an account of a third party which can be another monitoring device 10 user, a merchant, and the like, and provides transaction or transfer of fund results to the interaction engine 120 for presentation to a third party.

In one embodiment, the transaction engine 114 does not have the financial account or financial card information of the monitoring device 10 user that is doing the transfer. In some embodiments, the transaction engine 114 keeps only selected information of the monitoring device 10 user's financial accounts 118 or financial transaction cards.

In one embodiment, the wearable device communicates directly, without mobile device 74, with the payment system 116 and/or the user's financial account 118 or associated financial institution.

In one embodiment, the transaction engine 114 communicates and interacts with the financial account 118 or associated financial institution directly or through the payment system 116, through a user database, product database, and transaction database, which databases can be separate from or included in the payment system 116, over a Network System 101. The Network System 101 can be a communication network, as recited above, and can be based on well-known communication protocols, including but not limited to, a TCP/IP protocol.

With social networking applications, the monitoring device 10, with its unique ID, is an ID device. Information from the monitoring device 10 relating to social networking, and the like, communicates with system 32. In this manner, the wearable devices 10, with their own unique ID's, can be recognized. This can occur at different locations, close by, distanced, and notifications can be sent to the different users wearing a monitoring device 10 for a variety of social networking and other communication applications. Additionally, monitoring device 10, with its sensors 14 and ID can communicate directly to social networking sites, Network System 101 Systems, cloud services, and the like.

In one embodiment, with the current permissions given by the wearable device users, marketers, companies or individuals who wish can deliver advertisement monitoring device 10 users. More particularly, system 32 can be configured to allow marketers, and the like, to deliver advertisements to consumers to buy products or services offered by the marketer. Advertisements can also be sent to monitoring device 10 users with the appropriate permissions. In one embodiment, system 32 maintains the anonymity of the monitoring device 10 users while allowing the marketers to have their advertisements delivered to those that fall within their defined market segment.

In one embodiment, the wearable device ID of a user provides a method of identifying and contacting users of a social networking service. The method may include the steps of signing up for a social networking service, displaying the wearable device ID, viewing another person's unique wearable device ID displayed by another user, and finding that user on a social networking service website by searching for the user using the wearable device ID viewed.

System 32 may serve a number of purposes without straying from the scope of the present invention. For example, the social networking service may allow monitoring device 10 users to engage in non-romantic relationships, keep in touch with acquaintances, friends and family, professional business relationships, and romantic relationships, may allow communication between wearable device users on a message board or Network Systems 101 forum, and may allow users to follow up on missed-connections that otherwise would not have been realized.

In one embodiment, the step of providing personal information to start an account with system 10 for different applications may be performed by a purchasing or acquiring a monitoring device 10, with a unique assigned ID, and the user can fill in an online form. This form may require users to fill in fields on the form. These fields may include: first and last name, email address, a desired password, phone number, gender, birth date, address, geographic region, education information, employment information, interests, relationship information and interests, family information, religious views, ethnicity, physical features including hair color, eye color, measurements, and the like, type of relationship being sought, living situation, answers to quiz questions, and a personal description about interesting personality traits, among other things. In addition, users may upload one or a plurality of photographs for other users to view, or for users to store the photo or photos on the server of system 32.

In another embodiment the step of providing personal information to start an account with system 32 by monitoring device 10 users may be performed automatically. In this embodiment, system 32 can access a social networking service, access, via computer, contact lists or other sources of information that may include the type of information listed above.

In a further embodiment, the step of providing personal information to system 32 can be automated by importing data containing the personal information required from other social networking services including but not limited to Facebook®, LinkedIn®, MySpace®, Match.com®, EHarmony.com®, a user's email or contact list, v-card, and the like.

The unique wearable device ID may allow the user to be searched and identified by other users and potential users.

Also, a computer generated email address may be provided to a user. In one embodiment, this email address may be the user's user ID followed by "@iseenya.com." In another embodiment, the email address may be the user's user ID directed to another domain name.

In one embodiment, a computer generated personal page may be provided to a monitoring device 10 user. The personal page may utilize a computer to automatically import the information provided when signing up with system 32 or a social networking service. In another embodiment, the information and formatting of the personal page can be customizable.

When mobile device 74 is used, it communicates with one or more sensors 14 that are at the monitoring device 10, as more fully herein. The mobile device can 74 pull from system 32 updates from the server 16, including but not limited to settings such as alarms, name of the wearable device wearer using the ID, a sensor 14 and the like. Sensors 14 at the monitoring device 10 can send streams of information, both encrypted and non-encrypted to the mobile device and then to the server at system 32. Server 16 sends encrypted, and can also send non-encrypted information, to mobile device 74. Processing of this information can be achieved at the mobile device 74, and/or server 16. Mobile device 74 can receive raw sensor information from the monitoring device 10. This information can be compressed as well as non-compressed. A compression algorithm, at the wearable device and/or mobile device 74 or system 32, can be used in order to minimize the amount of information that server 16 sends. System 32 can include additional encryption and/or decryption systems.

Figure 17:
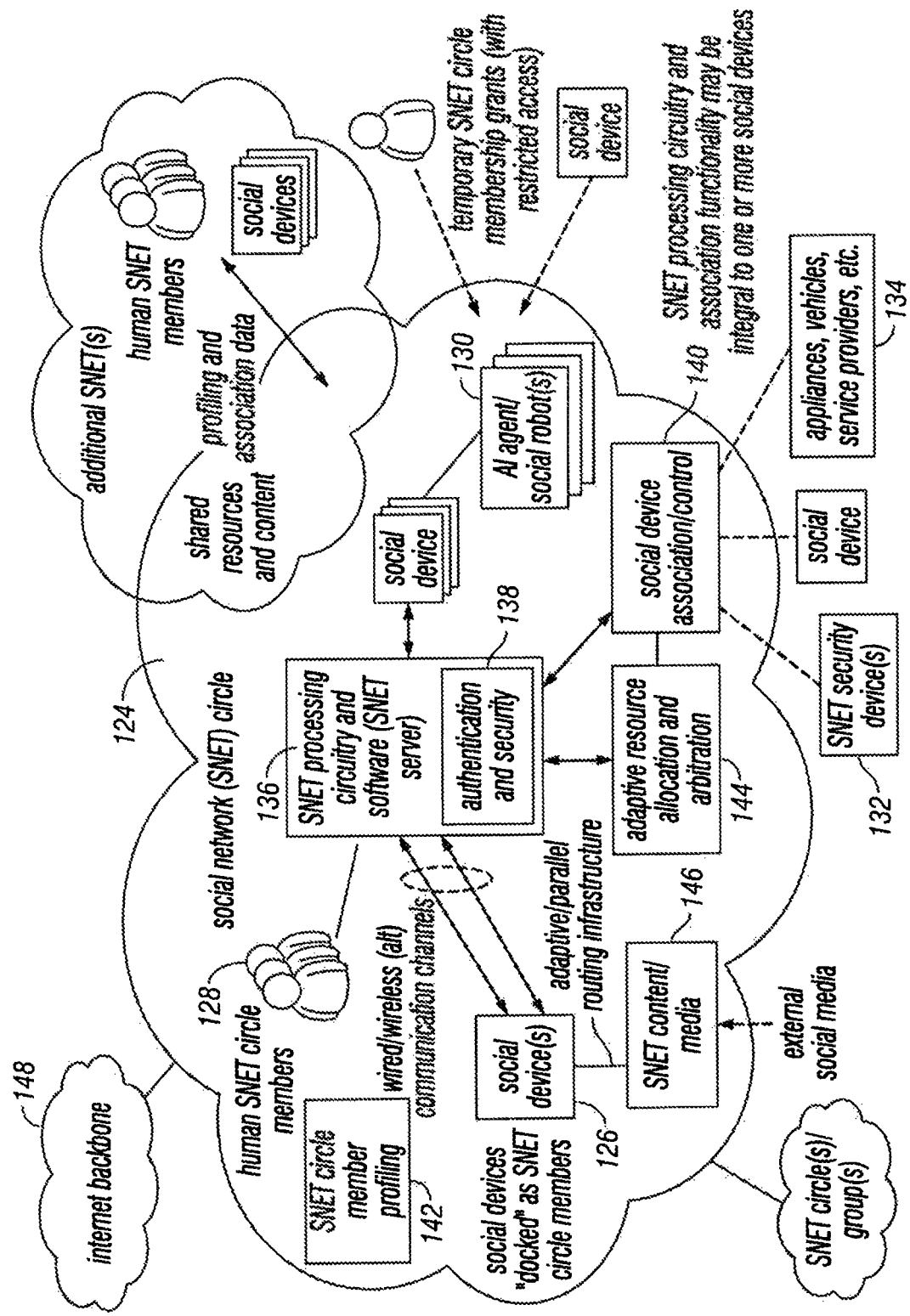
FIG. 17 illustrates an embodiment of a social network circle with social devices in accordance with one embodiment of the present invention.

Referring now to FIG. 17, a social network circle/group 124 (hereinafter "SNET circle") comprising social devices 126, including monitoring device 10, is shown. Beyond traditional social networking features and services, a SNET circle 124 and associated social devices 124 according to various embodiments of the invention include numerous novel features and attributes as described more fully below with general reference to the illustration. Monitoring device 10 can utilize network 101 for communication with the SNET circle, as well as with other social networking sites, or through system 32.

Briefly, membership in the SNET circle 124 may comprise docked and undocked social devices 124 and human SNET circle members [104] 128, as well as proxies thereof. Further, SNET circle 124 nodes may include device services and software (e.g., applications) of various types participating as members. By way of example, SNET circle members might include artificial intelligence agents/social robots 130, SNET security device(s) 132, appliances, vehicles and service providers 134, common or authorized members/functionality of other SNET circles 124, and the like. Further, access to specific content and resources of a SNET circle 124 may be shared with members of additional SNET(s) 124, including remote or web-based applications. Such access can be conditioned on acceptable profiling and association data. Similarly, social devices or individuals may be granted temporary or ad hoc memberships, with or without restricted access.

In the illustrated embodiment, formation, maintenance and operation of SNET circle 124 is performed by standalone or distributed SNET processing circuitry and software 136. It is noted that the "SNET processing circuitry" may comprise hardware, software, applications, or various combinations thereof, and be configurable to support various functionalities disclosed herein. Further, the SNET processing circuitry 136 may be included in a standalone server, server farm, cloud-based resources, Network System 101, system 32 and/or the various types of devices described below, and incorporate authentication and security functionality 138. In addition, specialized middleware may also be utilized by SNETs according to the invention, including standardized middleware with an associated certification process. Interactions and interdependencies within the SNET circle 124 may involve one or more of a social device association/control module 140, a SNET circle member profiling module 142, and an adaptive resource allocation and arbitration module 144 as described more fully below.

Distribution of internal and external SNET content/media 146 can be accomplished in a variety of ways in accordance with various embodiments of the invention. For example, media distribution may involve an adaptive or parallel Network System 101 routing infrastructure involving a wide variety of communication protocols and wired and/or wireless communications channels. SNET content/media 146 may comprise, for example, various user-driven (advertising) channels, pictures, videos, links, online text, etc. Access to such content, as well as communications with and remote access to social devices 124 of the SNET circle 124, may occur over a Network Systems backbone 148, cellular communication system, WAN, LAN, and the like.

Figure 18:
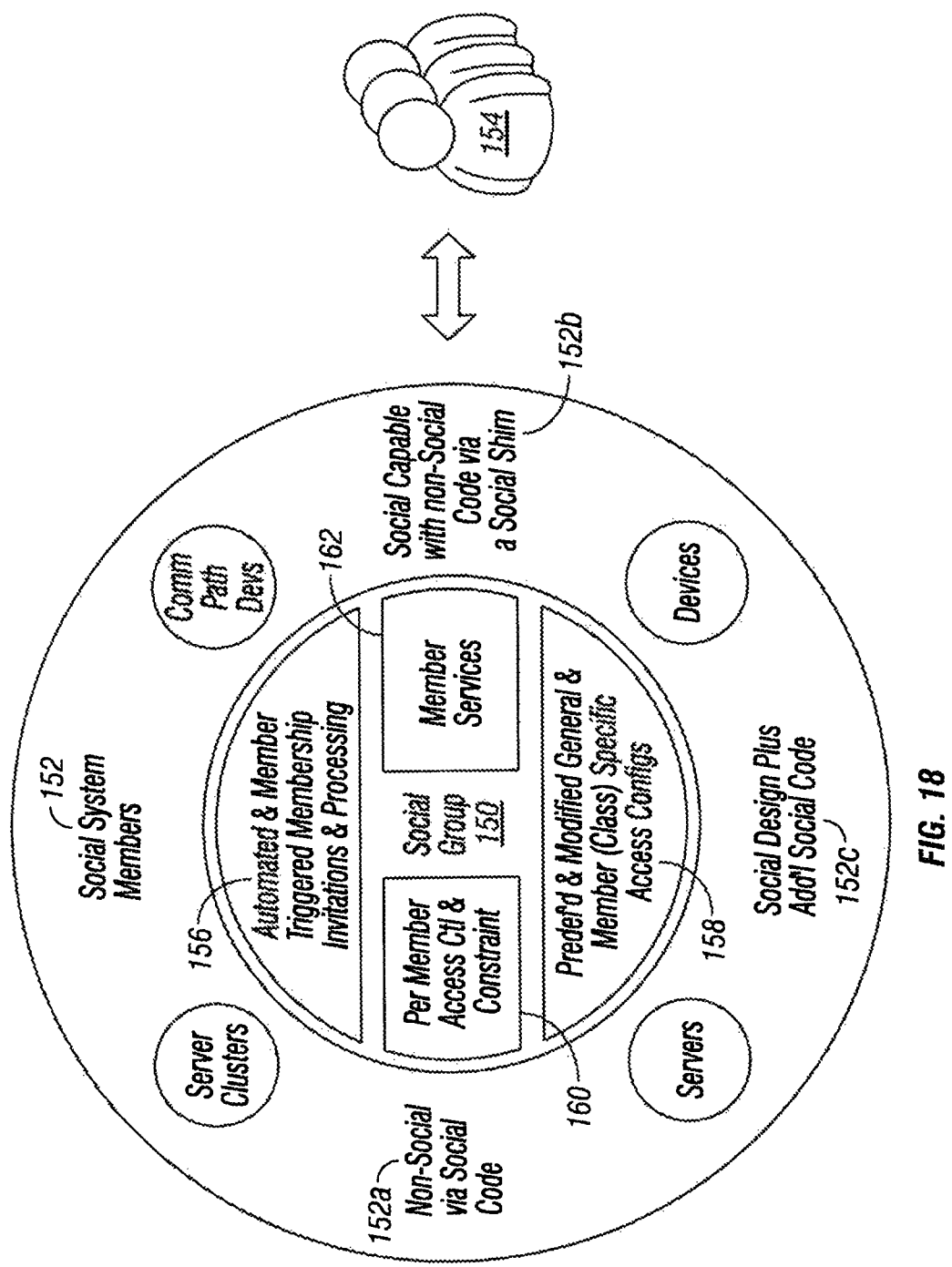
FIG. 18 illustrates an embodiment of a social group with a variety of members in accordance with one embodiment of the present invention.

FIG. 18 illustrates an embodiment of a social group 150 comprising a variety of members in accordance with the present invention that can communicate through their wearable devices 10 and other devices, including but not limited to mobile devices 74. In this embodiment, membership in the social group 150 may include a variety of novel social system members [204] 152 functioning in various capacities within the social group 150. As will be understood, certain of the social system members 152 may support direct or indirect associations between the social group 150 and human members/non-members and users 154.

In the illustrated embodiment, social system members (or nodes) 152 include one or more local or remote servers and server clusters that provide a support infrastructure for social group functionality and member operations (routing, data storage, services, etc.). Communications within the social group and with non-members may occur via dedicated or multi-function communication path devices.

Social system members 152 further include devices configured to operate as nodes within the social group 150. Social functionality in such devices and other social system members 152 can be implemented through various means. For example, a device may have integral hardware/firmware/software to support social group access and member operations. Alternatively, a general purpose device 152a may include social code that enables participation in the social group 150. In a further embodiment, a device 152b designed to include social functionality may participate in the social group 150 through a combination of non-social code and a social shim layer or driver wrapper. In yet another embodiment, a member device 152c having a social design may utilize additional social code, including code specific to a social group 150.

Participation in the social group 150 is supported through functionality that includes automated and member-triggered membership invitations and processing (membership management) 156. More particularly, membership management 156 may function to invite prospective members to participate in the social group 150 through automatic, automated and member-triggered processes. For example, membership management 156 might be configured by a human user 154 to establish a social group 150 by automatically inviting/accepting social system members having certain characteristics (such as devices owned or controlled by the user or acquaintances of the user).

Processing of accepted invitations and unsolicited requests to join the social group 150 may be conditioned upon input or authorization from an existing social system member(s) 152 or human user(s) 154 (e.g., through a user interface). Similarly, membership management 156 may be configured to generate automated suggestions regarding which prospective members receive an invitation. Various other approaches, such as those described herein, can be used to establish membership in accordance with the invention.

Access to and visibility of resources of a social group 150, including services and data, may be managed through general and member class-specific access configurations 158. For example, if membership in the social group 150 includes family members and associated devices, a uniform access configuration (or separate device and human configurations) could be applied across the class in an automatic or automated manner. In other embodiments, access control and constraints are imposed on a per-member basis.

The social group 150 may offer a wide variety of member services 162, including both internal and external services accessible by social system members 152. By way of example, the social group 150 may offer email or other communication services between full members and/or authorized guest members and visitors. As with other resources of the social group 150, access control and constraints on member services 162 may be applied to individual members or classes of members.

Figure 19:
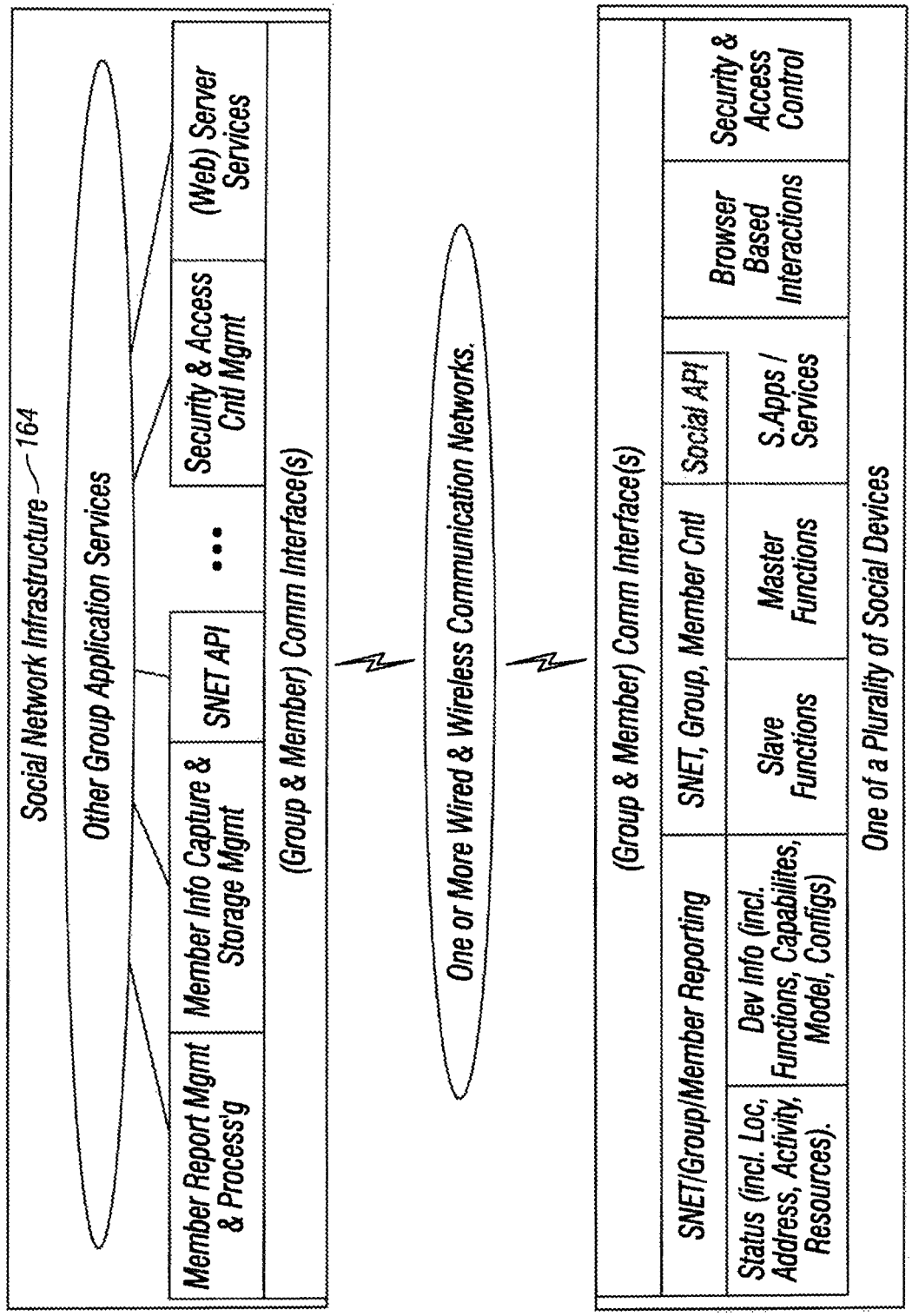
FIG. 19 is a functional block diagram illustrating a social network infrastructure and social devices in accordance with one embodiment of the invention.

FIG. 19 is a functional block diagram illustrating a social network (SNET) infrastructure 164, as more fully described and disclosed in EP 2582116, fully incorporated herein by reference.

Figure 20:
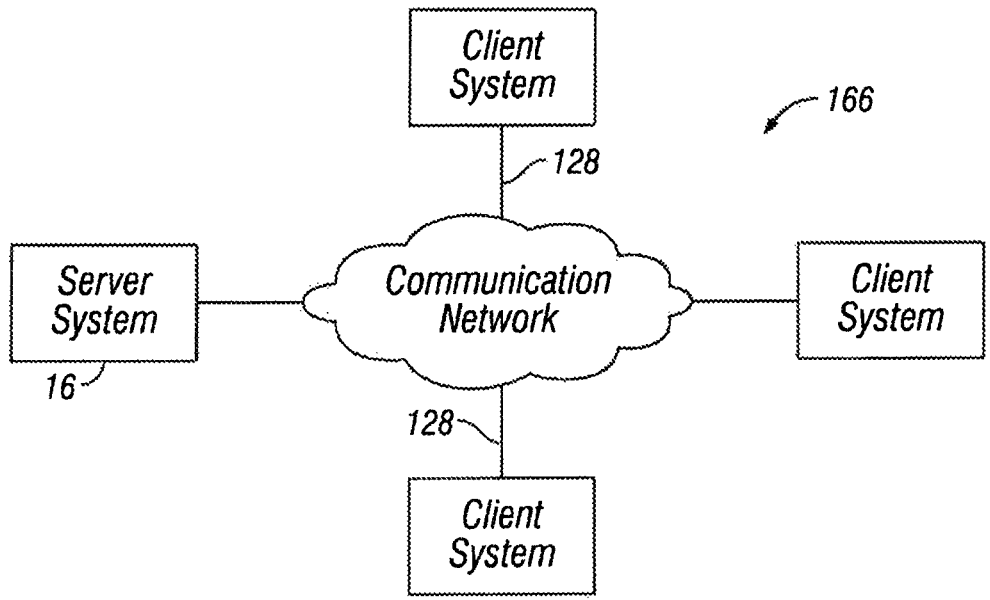
FIG. 20 illustrates a simplified block diagram of a client-server system and network in one embodiment of the present invention.

In one embodiment, illustrated in FIG. 20, wearable devices 10 are in communication with a distributed computer network 166 that can include networks 102, 104, 112, coupled to Network Systems 108 and system 32 via a plurality of communication links 168. Communication network 166 provides a mechanism for communication with system 16, monitoring device 10, social media networks, mobile devices 74, payment systems, 116, the engines 114, 120, 122, components of system 16, and with all third parties, as described above.

The communication network 166 may itself be comprised of many interconnected computer systems and communication links. Communication links 168 may be hardwire links, optical links, satellite or other wireless communications links, wave propagation links, or any other mechanisms for communication of information. Various communication protocols may be used to facilitate communication between the various systems shown in FIG. 20. These communication protocols may include TCP/IP, HTTP protocols, wireless application protocol (WAP), vendor-specific protocols, customized protocols, and others.

While in one embodiment, communication network 166 is the Network System 101, in other embodiments, communication network 166 may be any suitable communication network 166 including a local area network (LAN), a wide area network (WAN), a wireless network, an intranet, a private network, a public network, a switched network, and combinations of these, and the like.

System 32 is responsible for receiving information requests from wearable devices 10, third parties, and the like, performing processing required satisfying the requests, and for forwarding the results corresponding to the requests backing to the requesting monitoring device 10 and other systems. The processing required to satisfy the request may be performed by server 16 or may alternatively be delegated to other servers connected to communication network 166.

Figure 21:
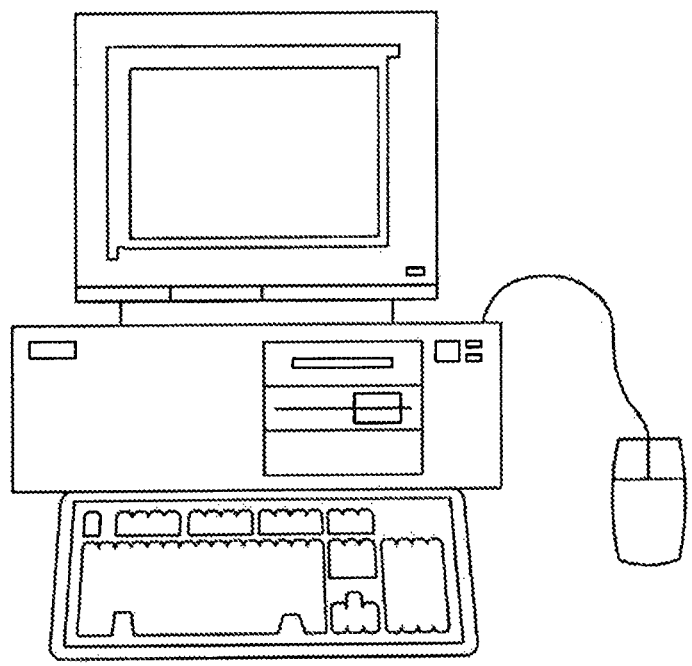
FIG. 21 illustrates a more detailed diagram of an exemplary client or server computer that can be used in one embodiment of the present invention.

FIG. 21 shows an exemplary computer system that can be utilized with the wearable devices 10. In an embodiment, a user interfaces with system 32 using a monitoring device 10 and then through a computer workstation system, such as shown in FIG. 21, a mobile device, and the like.

The communication network 166 may be the Network System 101, among other things. The network may be a wireless, a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11e, 802.11g, 802.11i, 802.11n, and 802.11ac, just to name a few examples), near field communication (NFC), radio-frequency identification (RFID), mobile or cellular wireless (e.g., 2G, 3G, 4G, 3GPP LTE, WiMAX, LTE, Flash-OFDM, HIPERMAN, iBurst, EDGE Evolution, UMTS, UMTS-TDD, IxRDD, and EV-DO). For example, signals from a computer may be transferred, at least in part, wirelessly to components or other computers.

Figure 22:
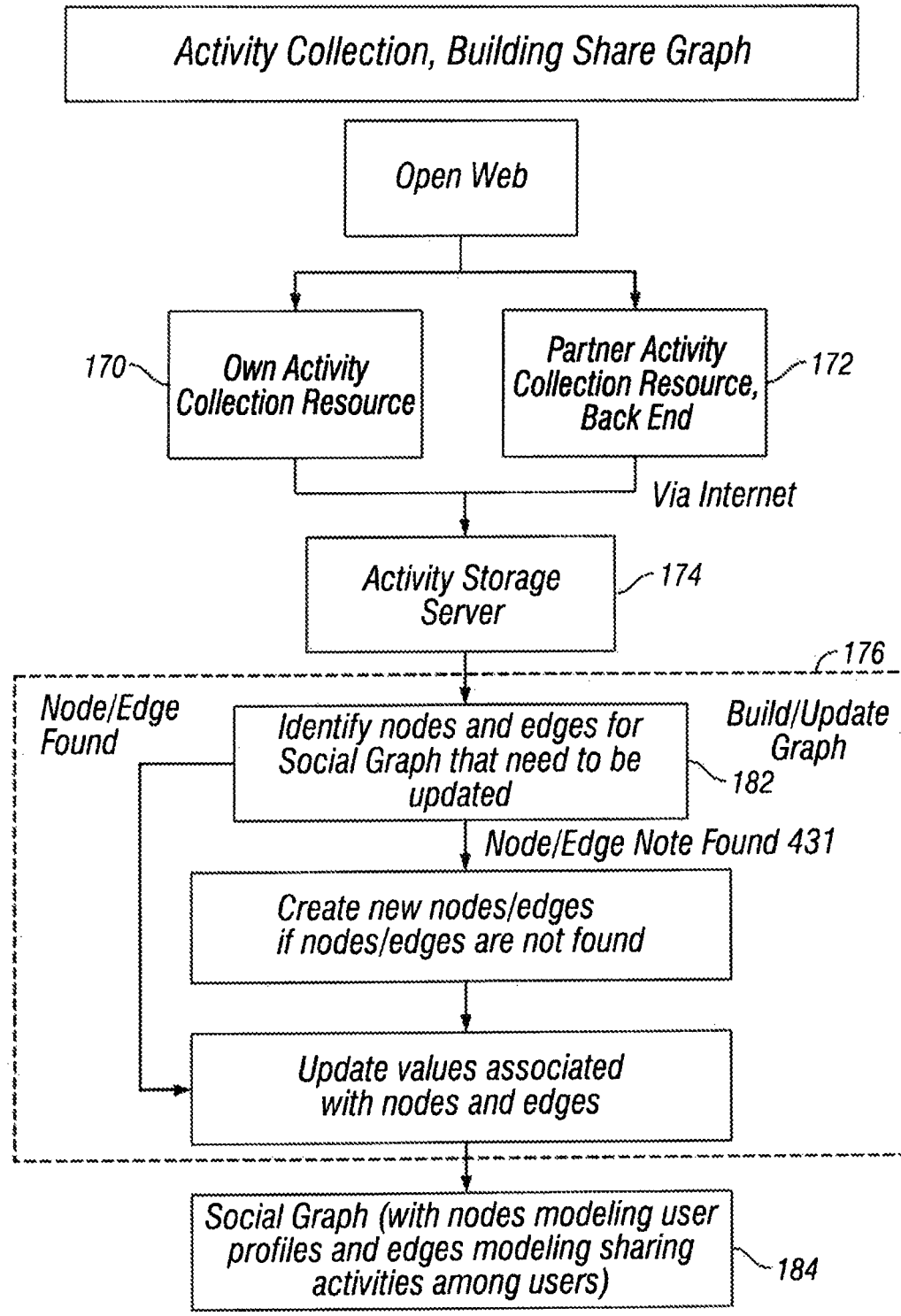
FIG. 22 illustrates a system for activity collection and building a social graph including sharing activity between users in one embodiment of the present invention.

FIG. 22 shows a system for activity collection and building a social graph for network monitoring device 10 users. The system monitors users as they surf the Web, their activities, locations, status, interests, and other things, This can be achieved without regard to whether the wearable device users 10 are logged into a membership site, such as a social networking site.

Resources 170 and 172 gather activity data and pass this data to an activity storage server 174, typically via Network Systems 108. Partner resource 172 may be processed by a partner back end, and then this data is passed to activity storage server 174.

Monitoring device 10 users can use social media sharing application or sites. Applications (e.g., a mobile device app or sites allow sharing of information with others. These can be used to collect activity data. A monitoring device 10 user (sender) can share information (e.g., video, photo, link, article, or other) by posting to a site. The monitoring device 10 user can post directly on the site or use an application program, such as a mobile application on a smartphone or tablet computer. When another user (recipient) clicks or vies the link, there is connection activity between the sender and recipient. This activity data is captured by system 32.

Messenger applications such as those on mobile device 74 or sites can allow Network Systems or Web messaging with others. Network Systems messaging is different from short messaging server (SMS) or text messaging. Messenger applications can be used to collect sharing activity data.

Users use messenger application to send links and other information to other users, and also achieve this using their wearable devices 10. A user (sender) can copy a link (e.g., via a clipboard) and send to one or more users via the messenger application with mobile device 74 and with its monitoring device 10. When a recipient user clicks on the link, there is connection activity between the sender and recipient for that link.

Sharing activity data can be captured as described above. There can be different data collectors for different devices and platforms. The activity data is transmitted to and stored at activity storage server 174, typically through Network Systems. Server 174 stores the data for further processing. There can be a significant amount of real-time data that is collected for processing. Distributed computing and processing can be used to process the data.

The activity data collected is stored at server 174, usually in a database or file systems on hard drives of server 174. There may be many terabytes of data that need are to be processed. Taking the stored activity data as input is a build-update graph component (e.g., executable code running on one or more servers or other computers). Build-update graph component 178 can run on the same server that stores the activity data, or may run on a separate server that accesses storage server 174.

In one embodiment, a build-update graph 180 builds or updates a social graph using the collected activity data. The social graph can be stored in one or more databases or file systems. In one embodiment, build-update graph 180 can include three components: (1) identify nodes and edges for social graph that need to be updated, (2) create new nodes/edges if nodes/edges are not found, and (3) update values associated with nodes and edges.

For the incoming activity data collected, identify nodes 182 scan through and find the nodes and edges of the social graph that need to be updated.

When system 32 is processing a user activity data it has the ID of the monitoring device 10 user and attributes this activity to that monitoring device 10 user.

When a node or edge is found, update values update the node or an edge (e.g., associated with the node). When a node or edge is not found, a new node or edge is created in the graph. The result of build/update graph is a social graph 184 with nodes modeling user profiles and edge modeling sharing activities among users.

Figure 23:
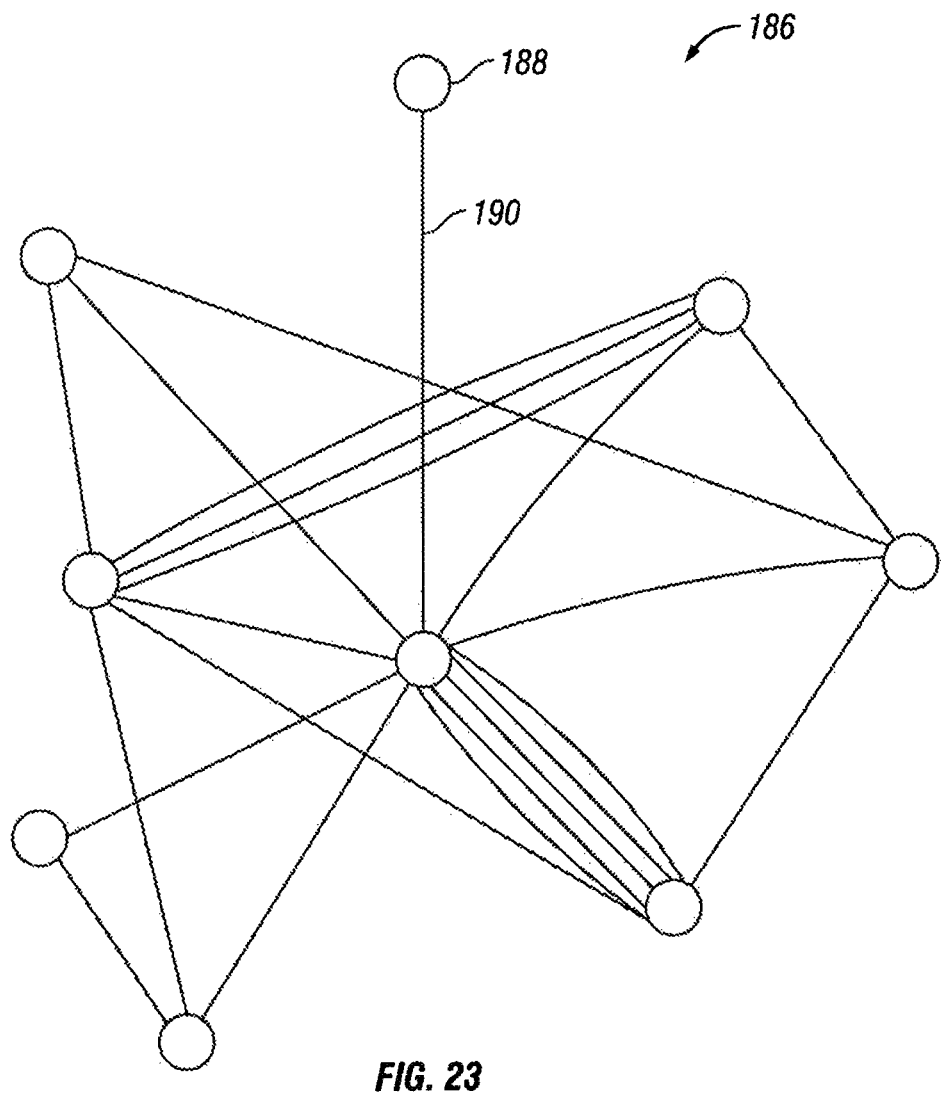
FIG. 23 illustrates a social graph with nodes representing users and edges representing sharing activity between the users in one embodiment of the present invention.

FIG. 23 shows a sample social graph 186 where circles 188 represent nodes and lines are edges 190 representing sharing interactions between nodes 182. There can be one or more edges 190 between two nodes 182. Several edges 190 between nodes 182 can indicate sharing activities along several categories: e.g., travel, computers, sports, and others.

Nodes 182 connected together directly have one degree of separation. Nodes 182 connected through one other node have two degrees of separation. Depending on a number of intervening nodes 182 between two nodes 182, this will be a number of degrees of separation between the two nodes 182.

In a specific implementation, edges 190 between nodes 182 indicate sharing activities along several categories such as travel, computers, sports, and the like. For each additional new sharing category, an additional edge 190 is added. In a specific implementation, for each additional new sharing interest category, an additional edge 190 is added. Further, in an implementation, the sharing interaction or edges 190 between the nodes 182 can be weighted (e.g., weighting in a range from 0 to 1), so that certain types of sharing interactions are given different significance. Weight can be used to represent a relative strength of interaction related to a particular interest category.

Some types of sharing activities that are tracked for the social graph (or share graph) include: sending messages between users; sending files between users; sending videos between users; sending an e-mail (e.g., Web e-mail) with a link from one user to another such as sharing a link to various social media sites; and sending instant messages between users. For mobile devices 74 the sharing activities can further include: sending SMS-type messages between users. In some embodiments, messages can be sending from wearable devices 10.

Once two users connect, such as one monitoring device 10 sending another monitoring device 10 user a message containing a link concerning a topic. When the recipient user clicks on the link from the sender user, system 32 will add an edge 190 to graph 186 to represent the activity. An edge 190 is added to the graph 186 to represent this sharing activity between the two users.

In a specific implementation, two monitoring device 10 users are connected when one user (sender) shares information with another user or group and the other user (recipient) consumes the information that was sent (e.g., clicked-back on the shared link, opened an attachment, opened a message). For example, simply placing a link on Facebook® wall so that all Facebook® "friends" can see this link or tweeting a link to Twitter® followers will not create a connection between the sender, or sharer, and people in the graph. This would create significant noise in the system. The connections are created between the sender and only those users who clicked back on (or otherwise consumed) the message.

In one embodiment, more recently sent messages are given a greater weight than older messages.

Figure 24:
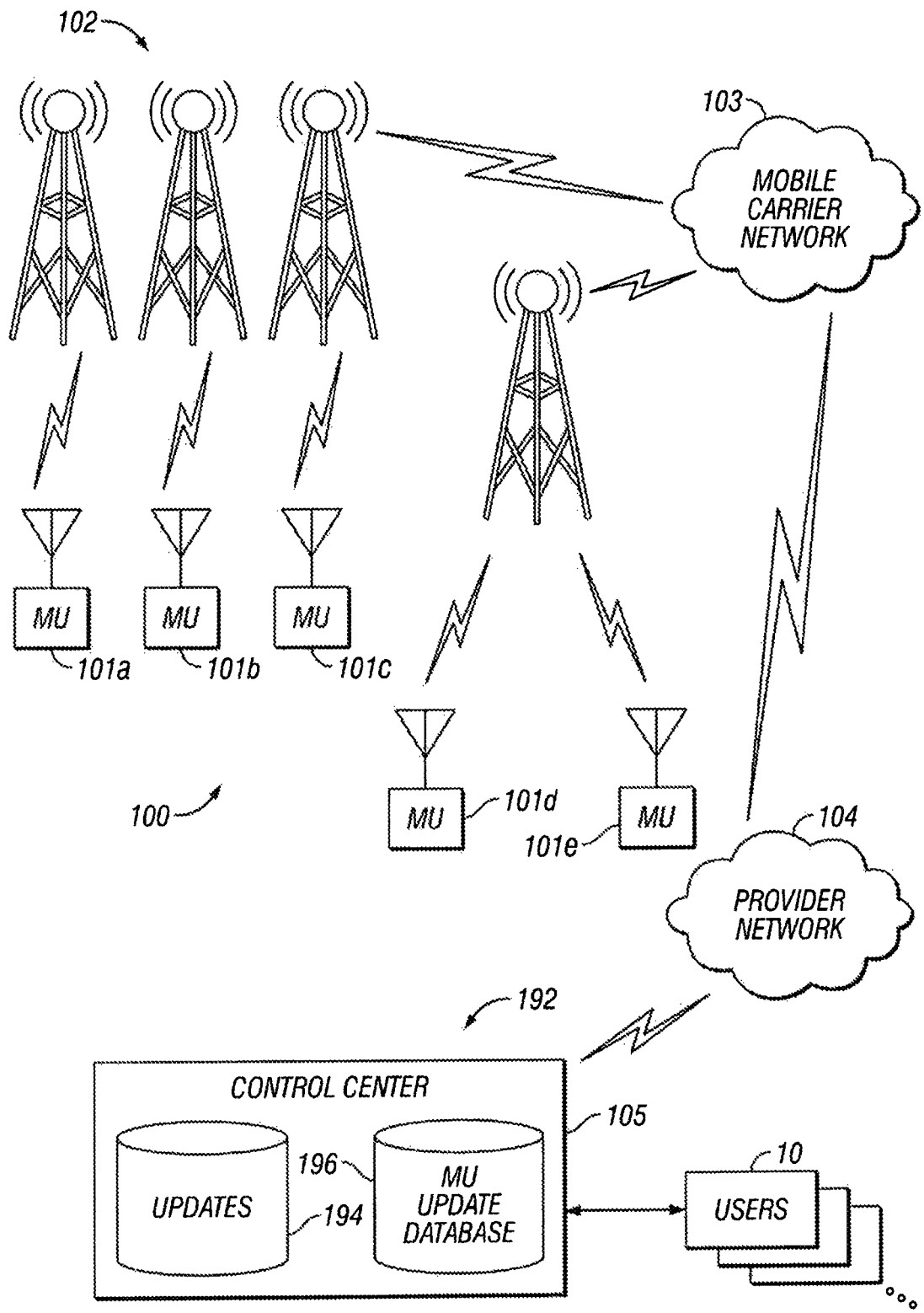
FIG. 24 is a block diagram of an embodiment of a system for distributing firmware updates to a large number of monitoring devices.

Referring now to FIG. 24, in one embodiment, telemetry system 32 monitors and provides firmware updates to a plurality of monitoring devices 10 that are programmed to report location, data and/or status periodically, in response to an event, or in response to a request by telemetry system 32. The monitoring devices 10 through a Network System 101 (not shown) are in communication with a control or monitoring center 192 which collects the location and/or status data for each of all or a selected portion of the monitoring devices 10.

When programming, software, firmware, configuration or similar updates are available for the monitoring devices 10, the control center 192 collects those firmware updates and the identity of the monitoring devices 10 requiring those updates and stores that information. Separate databases may be employed for the updates 194 and the monitoring device 10 update status 196, or the databases may be combined. Users can access control center 192 to upload updates, check on the status of their monitoring device 10 or to retrieve location, data and reporting information related to the monitoring devices 10. The control center 192 can then attempt to contact each mobile device requiring the update or can wait until it receives a message from each monitoring device 10. Once the control center 192 establishes contact, it initializes the firmware update process and begins sending the update to each monitoring device 10 to which contact has been established. Once a monitoring device 10 receives the entire update and has installed it, it can send a confirmation to the control center 192 which is then noted in the MU update database 196. If the confirmation is not received, for instance because a communication link was broken and the entire update was not received, the control center 192 tries to re-contact each non-updated monitoring device 10 and each monitoring device 10 to which the control center 192 has not yet made contact.

For each monitoring device 10 that has received and confirmed the update, the MU update database 196 is updated to reflect that the monitoring device 10 is up to date. The control center 192 continues this process until each of the monitoring devices 10 has confirmed the installation of the updated firmware. The users of each monitoring device 10 can be sent reports reflecting the status of the software update process. While a particular number of monitoring devices 10 are represented in FIG. 24, any number of monitoring devices 10 can be accommodated using the concepts described herein.

Figure 25:
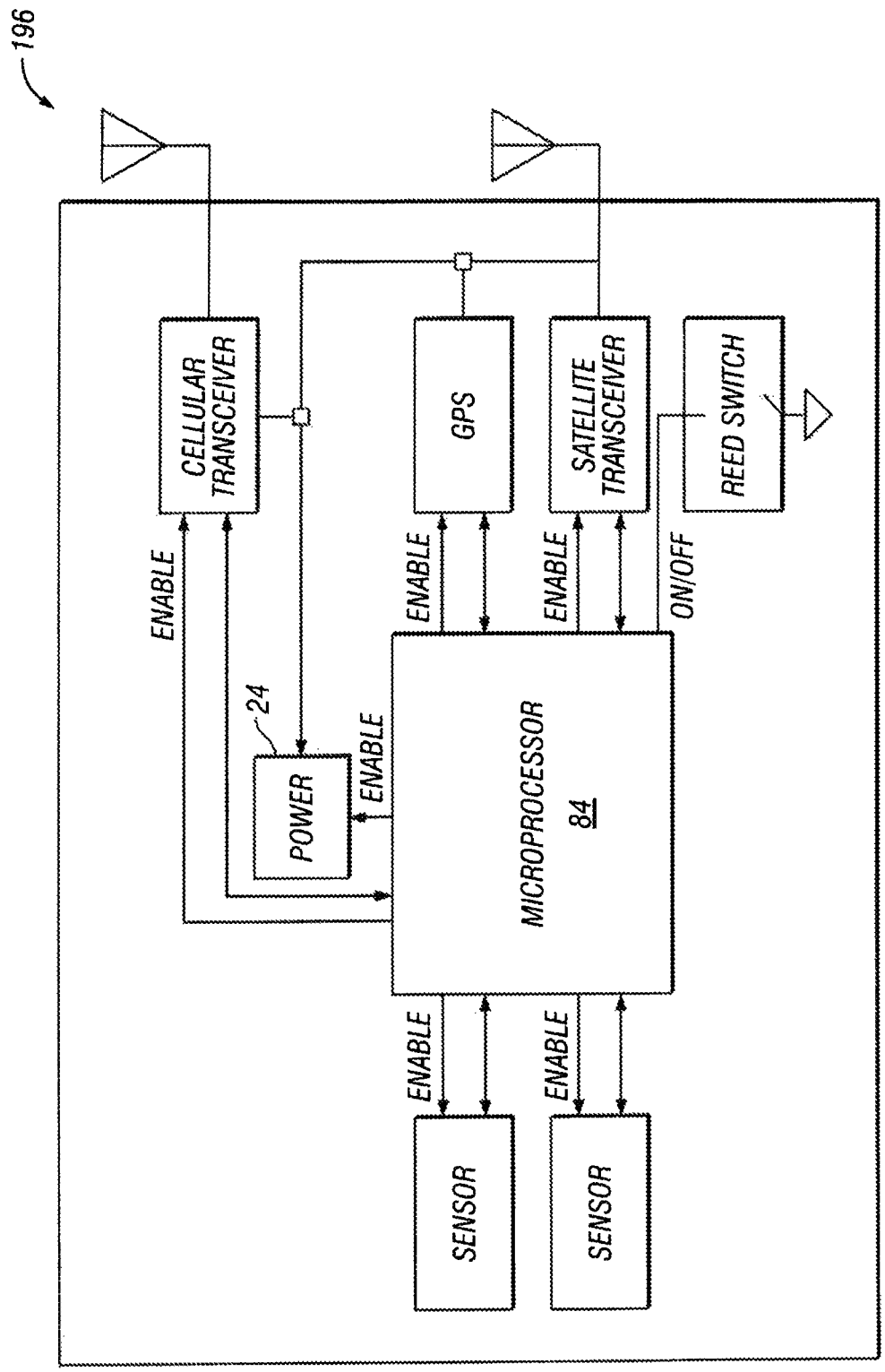
FIG. 25 is a block diagram of an embodiment of an asset tag for a monitoring device having wireless communications capabilities.

FIG. 25 discloses one embodiment of monitoring device 10, with the ID or asset tag. The tag can includes microprocessor 84 programmable to execute desired instructions and to control the operation of tag. The microprocessor 84 may have internal memory capable of storing data and programming information or may use memory external to the microprocessor 84. The tag can also include a cellular transceiver and associated cellular antenna to perform cellular communications. Power for the cellular transceiver is supplied by a power system or battery 24. The tag 196 can also include a satellite location determination device, which can be GPS or satellite service based, and a satellite transmitter, receiver or transceiver, which can use a satellite antenna.

As described, communications with the control center 192 can be done using satellite, Network System 101 or other long range communication systems. Sensors 10 can be embedded in or connected to the monitoring device 10, as described above. A reed switch 207 is an electrical switch that is activated by a magnetic field and can be used to enable or disable the monitoring device 10.

Figure 26:
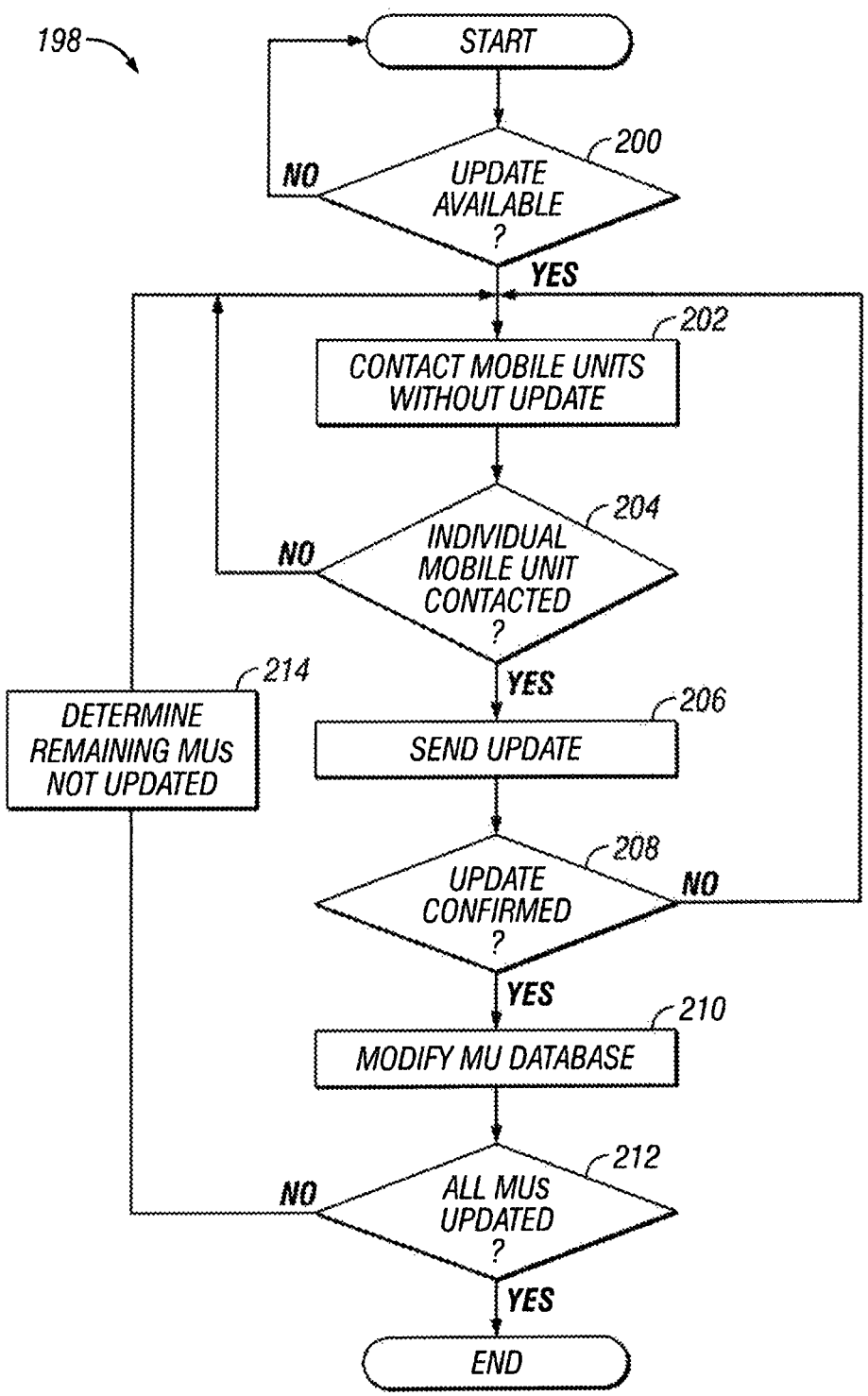
FIG. 26 is a flow chart for an embodiment of a method of distributing firmware updates to a large number of monitoring devices.

Referring now to FIG. 26, a flow chart of an embodiment of a method 198 for updating the software, firmware programming, configuration, or similar updates for remote devices/monitoring devices 10 is described. The method begins in decision block 200 by detecting an available update for one or more of a plurality of monitoring devices 10, each of the monitoring devices geographically distributed from the control center 192. The control center 192 then attempts to contact each monitoring device 10, as shown by block 202, or waits to be contacted by each monitoring device 10. Particular monitoring devices 10 may be initially unavailable to the control center by being out of range or unable to establish a good communications link.

Decision block 204 determines whether individual units have contacted the control center. If a unit has not contacted the control center the method can either wait or return to block 202 where the control center re-contacts the monitoring device 10.

Once a particular monitoring device 10 has been contacted, the control center 192 sends the update to that monitoring device 10 to be installed by the monitoring device 10, as shown by block 206. Once finished, the monitoring device 10 confirms completion as shown by block 208 of the installation and returns to normal operation. If the update is not confirmed by the monitoring device 10 having been installed, the method returns to block 202 to re-attempt the update. The update may fail for a variety of reasons, including loss of communications contact with the control center, or interruption due to events at the monitoring device 10. Once the update has been confirmed at that monitoring device 10, the MU update database at the control center is updated to reflect the completion of the update for that monitoring device 10, as shown by block 210.

The control center 192 periodically checks to see if all the monitoring devices 10 required to install the update have been complete, as shown by block 212, and if not, determines the remaining monitoring devices 10 to be updated, block 214, and attempts to contact those monitoring devices 10 to complete the update process. While method 198 illustrates one embodiment of the update process, one skilled in the art would recognize that variations on the process can be implemented without departing from the scope of the present invention.

Figure 27:
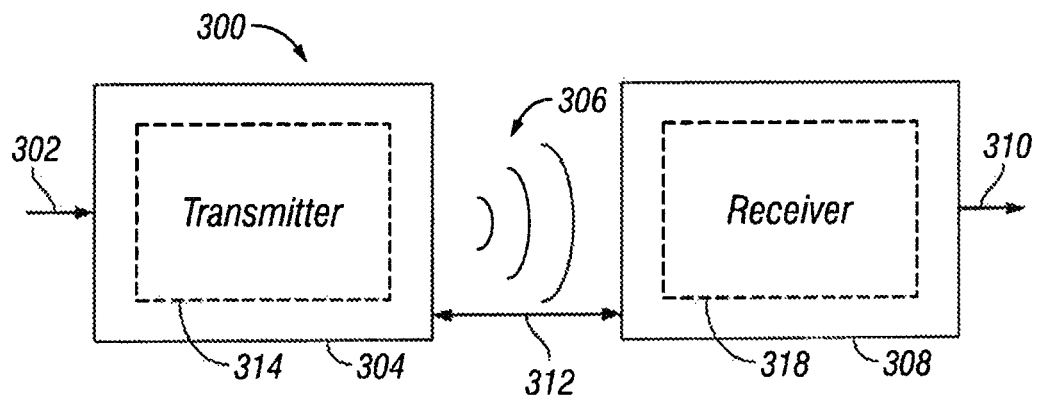
FIG. 27 illustrates one embodiment of a wireless power transfer system that can be used with the present invention.

In one embodiment of the present invention a wireless transmission or charging system 300 is provided that can be part of or distinct from telemetry system, as illustrated in FIG. 27. System 300 is in communication with monitoring devices 10, and also with telemetry system 32 when it is separate from telemetry system 32. Input power 302 is provided to a transmitter 304 for generating a radiated field 306 for providing energy transfer. A receiver 308 couples to the radiated field 306 and generates an output power 310 for storing or consumption by a device (not shown) coupled to the output power 310. Both the transmitter 304 and the receiver 308 are separated by a distance 312. In one exemplary embodiment, transmitter 304 and receiver 308 are configured according to a mutual resonant relationship and when the resonant frequency of receiver 308 and the resonant frequency of transmitter 304 are very close, transmission losses between the transmitter 304 and the receiver 308 are minimal when the receiver 308 is located in the "near-field" of the radiated field 306.

Transmitter 304 can include a transmit antenna 314 for providing a means for energy transmission and receiver 308 further includes a receive antenna 318 for providing a means for energy reception. The transmit and receive antennas are sized according to applications and devices to be associated therewith. An efficient energy transfer can occur by coupling a large portion of the energy in the near-field of the transmitting antenna to a receiving antenna rather than propagating most of the energy in an electromagnetic wave to the far field. When in this near-field a coupling mode may be developed between the transmit antenna 314 and the receive antenna 318. The area around the antennas 314 and 318 where this near-field coupling may occur is referred to herein as a coupling-mode region.

Figure 28:
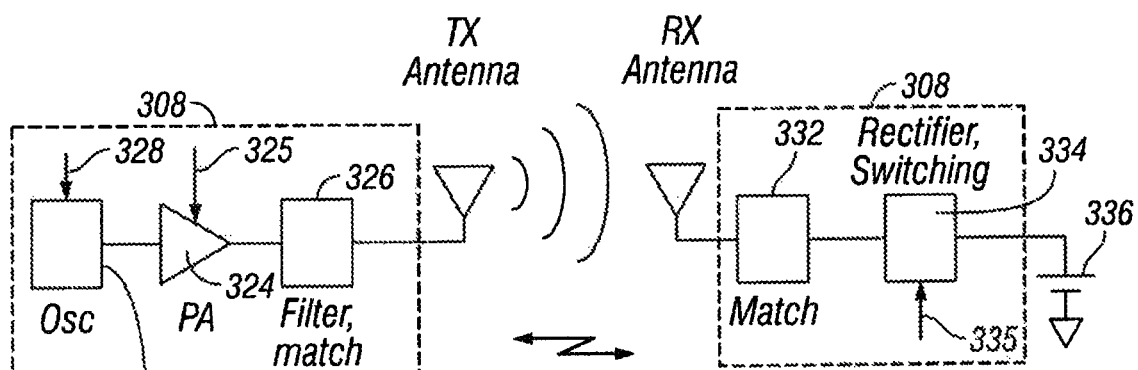
FIG. 28 illustrates another wireless power transfer system that can be used with the present invention.

Referring to FIG. 28, the transmitter 304 can include an oscillator 322, a power amplifier 324 and a filter and matching circuit 326. The oscillator is configured to generate a desired frequency, which may be adjusted in response to adjustment signal 323. The oscillator signal may be amplified by the power amplifier 324 with an amplification amount responsive to control signal 325. The filter and matching circuit 326 may be included to filter out harmonics or other unwanted frequencies and match the impedance of the transmitter 304 to the transmit antenna 314.

The receiver 308 may include a matching circuit 332 and a rectifier and switching circuit 334 to generate a DC power output to charge a battery 336 as shown in FIG. 28 or power a device coupled to the receiver (not shown). The rectifier and switching circuit 334 shown receives a control signal 335. The matching circuit 332 may be included to match the impedance of the receiver 308 to the receive antenna 318. The receiver 308 and transmitter 304 may communicate on a separate communication channel 319.

Figure 29:
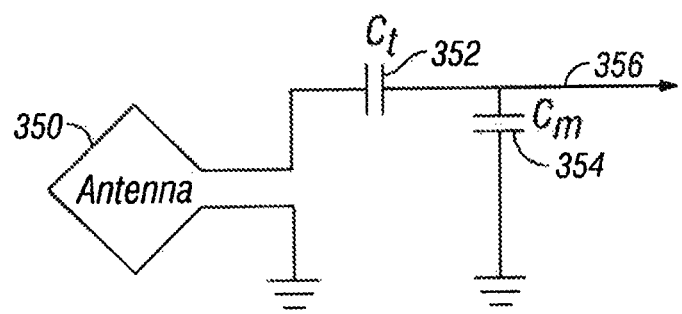
FIG. 29 illustrates one embodiment of a loop antenna for use in one various embodiments of the present invention.

As illustrated in FIG. 29, antennas can be utilized as a "loop" antenna 350, which may also be referred to herein as a "magnetic" antenna. Loop antennas may be configured to include an air core or a physical core such as a ferrite core. Air core loop antennas may be more tolerable to extraneous physical devices placed in the vicinity of the core. Furthermore, an air core loop antenna allows the placement of other components within the core area. In addition, an air core loop may more readily enable placement of the receive antenna 318 (FIG. 28) within a plane of the transmit antenna 314 (FIG. 28) where the coupled-mode region of the transmit antenna 314 (FIG. 28) may be more powerful.

In one embodiment, efficient transfer of energy between the transmitter 304 and receiver 308 occurs during matched or nearly matched resonance between the transmitter 304 and the receiver 308. However, even when resonance between the transmitter 304 and receiver 308 are not matched, energy may be transferred at a lower efficiency. Transfer of energy can be by coupling energy from the near-field of the transmitting antenna to the receiving antenna residing in the neighborhood where this near-field is established rather than propagating the energy from the transmitting antenna into free space.

The resonant frequency of the loop or magnetic antennas is based on the inductance and capacitance. Inductance in a loop antenna is generally simply the inductance created by the loop, whereas, capacitance is generally added to the loop antenna's inductance to create a resonant structure at a desired resonant frequency. As a non-limiting example, capacitor 352 and capacitor 354 may be added to the antenna to create a resonant circuit that generates resonant signal 356. Accordingly, for larger diameter loop antennas, the size of capacitance needed to induce resonance decreases as the diameter or inductance of the loop increases. Furthermore, as the diameter of the loop or magnetic antenna increases, the efficient energy transfer area of the near-field increases. Of course, other resonant circuits are possible. As another non-limiting example, a capacitor may be placed in parallel between the two terminals of the loop antenna. In addition, those of ordinary skill in the art will recognize that for transmit antennas the resonant signal 356 may be an input to the loop antenna 350.

In some embodiments, power is coupled between two antennas that are in the near-fields of each other. The near-field is an area around the antenna in which electromagnetic fields exist but may not propagate or radiate away from the antenna. They can be confined to a volume that is near the physical volume of the antenna. As non-limiting examples, magnetic type antennas such as single and multi-turn loop antennas can be used for both transmit (Tx) and receive (Rx) antenna systems since magnetic near-field amplitudes tend to be higher for magnetic type antennas in comparison to the electric near-fields of an electric-type antenna (e.g., a small dipole). This can provide higher coupling between the pair. Furthermore, "electric" antennas (e.g., dipoles and monopoles) or a combination of magnetic and electric antennas is also contemplated.

The Tx antenna can be operated at a frequency that is low enough and with an antenna size that is large enough to achieve good coupling (e.g., >−4 dB) to a small receive antenna at significantly larger distances than allowed by far field and inductive approaches mentioned earlier. If the transmit antenna is sized correctly, high coupling levels (e.g., −1 to −4 dB) can be achieved when the receive antenna on a host device is placed within a coupling-mode region (i.e., in the near-field) of the driven transmit loop antenna.

Figure 30:
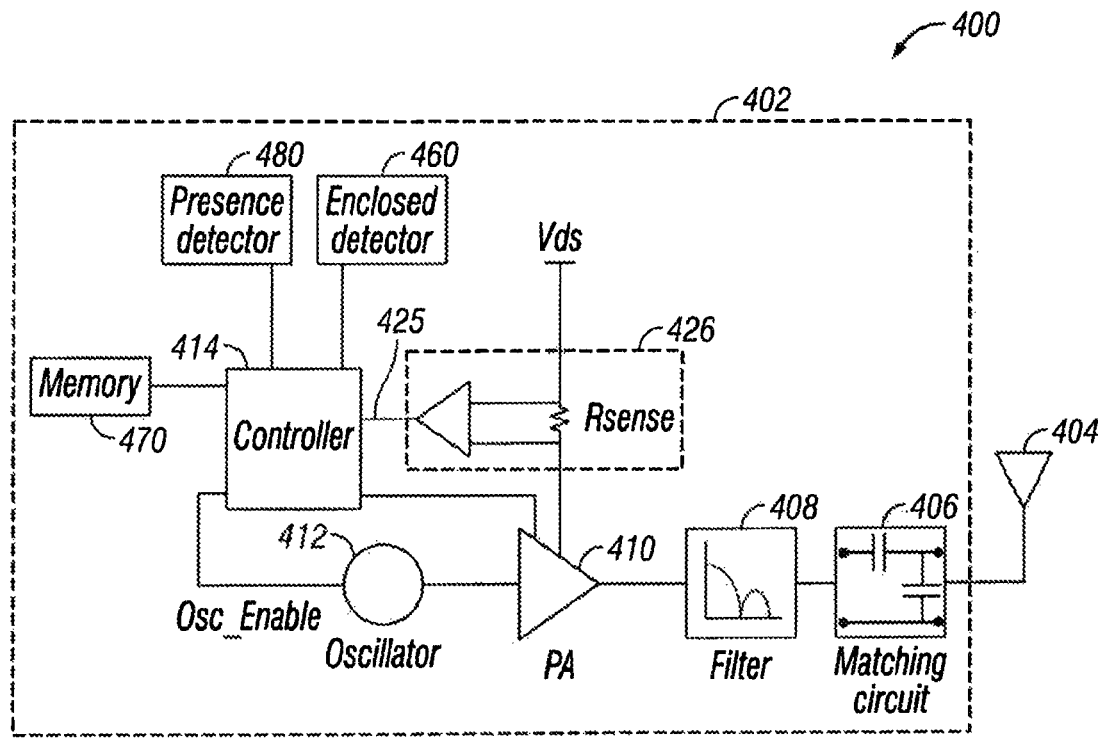
FIG. 30 illustrates one embodiment of a transmitter that can be used with the present invention.

FIG. 30 illustrates an embodiment of a transmitter 400 that can be utilized the transmitter 400 includes transmit circuitry 402 and a transmit antenna 404. Generally, transmit circuitry 402 provides RF power to the transmit antenna 404 by providing an oscillating signal resulting in generation of near-field energy about the transmit antenna 404. By way of example, transmitter 400 may operate at the 13.56 MHz ISM band.

In one embodiment, transmit circuitry 402 includes a fixed impedance matching circuit 406 for matching the impedance of the transmit circuitry 402 (e.g., 50 ohms) to the transmit antenna 404 and a low pass filter (LPF) 408 configured to reduce harmonic emissions to levels to prevent self-jamming of devices coupled to receivers 308 (FIG. 27). In other embodiments of the matching circuit can include inductors and transformers. In one embodiment, the low pass filter has different filter topologies, including but not limited to, notch filters that attenuate specific frequencies while passing others and may include an adaptive impedance match, that can be varied based on measurable transmit metrics, such as output power to the antenna or DC current draw by the power amplifier.

Transmit circuitry 402 can include a power amplifier 410 that drives an RF signal as determined by an oscillator 412 (also referred to herein as a signal generator). The transmit circuitry may be comprised of discrete devices or circuits, or alternately, may be comprised of an integrated assembly. An exemplary RF power output from transmit antenna 404 may be on the order of 2.5 to 8.0 Watts.

Transmit circuitry 402 can include a controller 414 for enabling the oscillator 412 during transmit phases (or duty cycles) for specific receivers, for adjusting the frequency of the oscillator, for adjusting the output power level, for implementing a communication protocol for interacting with neighboring devices through their attached receivers. The controller 414 is also for determining impedance changes at the transmit antenna 404 due to changes in the coupling-mode region due to receivers placed therein.

The transmit circuitry 402 can include a load sensing circuit 416 for detecting the presence or absence of active receivers in the vicinity of the near-field generated by transmit antenna 404. By way of example, a load sensing circuit 416 monitors the current flowing to the power amplifier 410, which is affected by the presence or absence of active receivers in the vicinity of the near-field generated by transmit antenna 404. Detection of changes to the loading on the power amplifier 410 are monitored by controller 414 for use in determining whether to enable the oscillator 412 for transmitting energy to communicate with an active receiver.

Transmit antenna 404 can be an antenna strip with a thickness, width and metal type selected to keep resistive losses low. The transmitter 400 may gather and track information about the whereabouts and status of receiver devices that may be associated with the transmitter 400. Thus, the transmitter circuitry 402 may include a presence detector 480, an enclosed detector 490, or a combination thereof, connected to the controller 414 (also referred to as a processor herein). The controller 414 may adjust an amount of power delivered by the amplifier 410 in response to presence signals from the presence detector 480 and the enclosed detector 490. The transmitter can receive power through a number of power sources, including but not limited to, an AC-DC converter to convert conventional AC power present in a building, a DC-DC converter to convert a conventional DC power source to a voltage suitable for the transmitter 400, or directly from a conventional DC power source.

In one embodiment, the presence detector 480 can be a motion detector utilized to sense the initial presence of a device to be charged that is inserted into the coverage area of the transmitter. After detection, the transmitter may be turned on and the RF power received by the device may be used to toggle a switch on the receiver device in a pre-determined manner, which in turn results in changes to the driving point impedance of the transmitter.

In one embodiment, the presence detector 480 is a detector capable of detecting a human, for example, by infrared detection, motion detection, or other suitable means. In various embodiments, regulations can be provided that limit an amount of power that a transmit antenna can transmit at a specific frequency.

As a non-limiting example, the enclosed detector 490 (may also be referred to herein as an enclosed compartment detector or an enclosed space detector) may be a device such as a sense switch for determining when an enclosure is in a closed or open state. When a transmitter is in an enclosure that is in an enclosed state, a power level of the transmitter may be increased.

Figure 31:
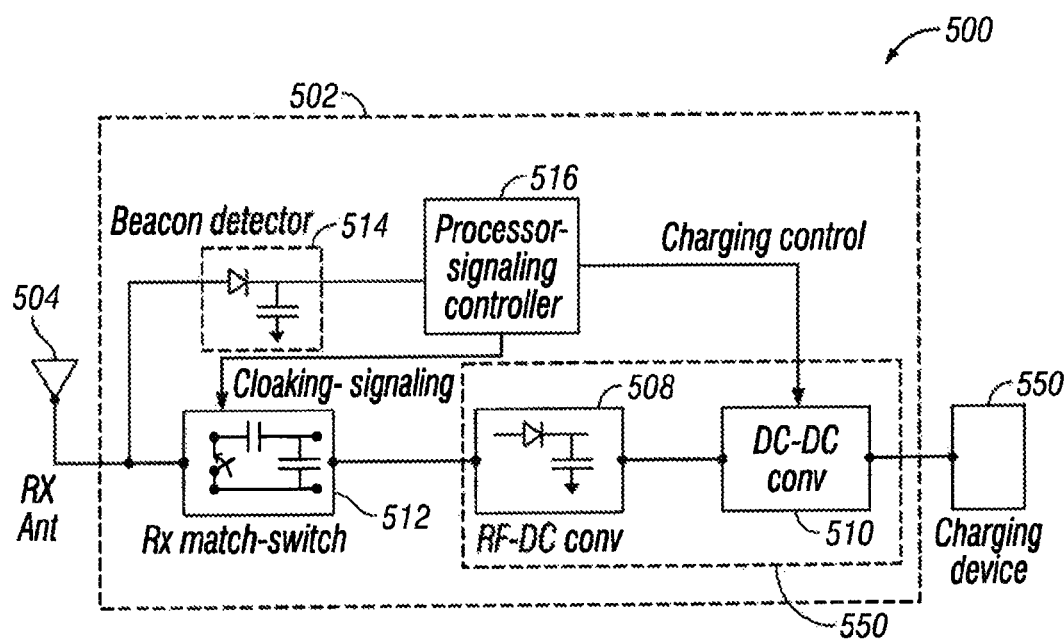
FIG. 31 illustrates one embodiment of a receiver that can be used with the present invention.

As illustrated in FIG. 31, a receiver 500 includes receive circuitry 502 and a receive antenna 504. Receiver 500 further couples to device 550 for providing received power thereto. It should be noted that receiver 500 is illustrated as being external to device 550 but may be integrated into device 550. Generally, energy is propagated wirelessly to receive antenna 504 and then coupled through receive circuitry 502 to device 550.

The receive antenna 504 is tuned to resonate at the same frequency, or near the same frequency, as transmit antenna 404 (FIG. 30). Receive antenna 404 may be similarly dimensioned with transmit antenna 404 or may be differently sized based upon the dimensions of the associated device 550. By way of example, device 550 may be a portable electronic device having diametric or length dimension smaller that the diameter of length of transmit antenna 404. In such an example, receive antenna 504 may be implemented as a multi-turn antenna in order to reduce the capacitance value of a tuning capacitor (not shown) and increase the receive antenna's impedance. By way of example, receive antenna 504 may be placed around the substantial circumference of device 550 in order to maximize the antenna diameter and reduce the number of loop turns (i.e., windings) of the receive antenna and the inter-winding capacitance.

Receive circuitry 502 provides an impedance match to the receive antenna 504. Receive circuitry 502 includes power conversion circuitry 506 for converting a received RF energy source into charging power for use by device 550. Power conversion circuitry 506 includes an RF-to-DC converter 508 and may also in include a DC-to-DC converter 510. RF-to-DC converter 508 rectifies the RF energy signal received at receive antenna 504 into a non-alternating power while DC-to-DC converter 510 converts the rectified RF energy signal into an energy potential (e.g., voltage) that is compatible with device 550. Various RF-to-DC converters are contemplated, including partial and full rectifiers, regulators, bridges, doublers, as well as linear and switching converters.

Receive circuitry 502 may further include switching circuitry 512 for connecting receive antenna 504 to the power conversion circuitry 506 or alternatively for disconnecting the power conversion circuitry 506. Disconnecting receive antenna 504 from power conversion circuitry 506 not only suspends charging of device 550, but also changes the "load" as "seen" by the transmitter 200 (FIG. 28), which can be used to "cloak" the receiver from the transmitter.

As disclosed above, transmitter 400 includes load sensing circuit 416 which detects fluctuations in the bias current provided to transmitter power amplifier 410. Accordingly, transmitter 400 has a mechanism for determining when receivers are present in the transmitter's near-field.

In an exemplary embodiment, communication between the transmitter and the receiver refers to a device sensing and charging control mechanism, rather than conventional two-way communication. In other words, the transmitter uses on/off keying of the transmitted signal to adjust whether energy is available in the near-field. The receivers interpret these changes in energy as a message from the transmitter. From the receiver side, the receiver uses tuning and de-tuning of the receive antenna to adjust how much power is being accepted from the near-field. The transmitter can detect this difference in power used from the near-field and interpret these changes as a message from the receiver.

In one embodiment, receive circuitry 502 has signaling detector and beacon circuitry 514 used to identify received energy fluctuations that can correspond to informational signaling from the transmitter to the receiver. The signaling and beacon circuitry 514 can detect the transmission of a reduced RF signal energy (i.e., a beacon signal) and to rectify the reduced RF signal energy into a nominal power for awakening either un-powered or power-depleted circuits within receive circuitry 502 in order to configure receive circuitry 502 for wireless charging.

Receive circuitry 502 can have processor 516 for coordinating the processes of receiver 500 described herein including the control of switching circuitry 512 described herein. Cloaking of receiver 500 can also occur upon the occurrence of other events including detection of an external wired charging source (e.g., wall/USB power) providing charging power to device 550. Processor 516, in addition to controlling the cloaking of the receiver, can also monitor beacon circuitry 514 to determine a beacon state and extract messages sent from the transmitter. Processor 516 can also adjust DC-to-DC converter 510 for improved performance.

In some exemplary embodiments, the receive circuitry 520 can signal a power requirement to a transmitter in the form of, for example, desired power level, maximum power level, desired current level, maximum current level, desired voltage level, and maximum voltage level. Based on these levels, and the actual amount of power received from the transmitter, the processor 516 can adjust the operation of the DC-to-DC converter 510 to regulate its output in the form of adjusting the current level, adjusting the voltage level, or a combination thereof.

Figure 32:
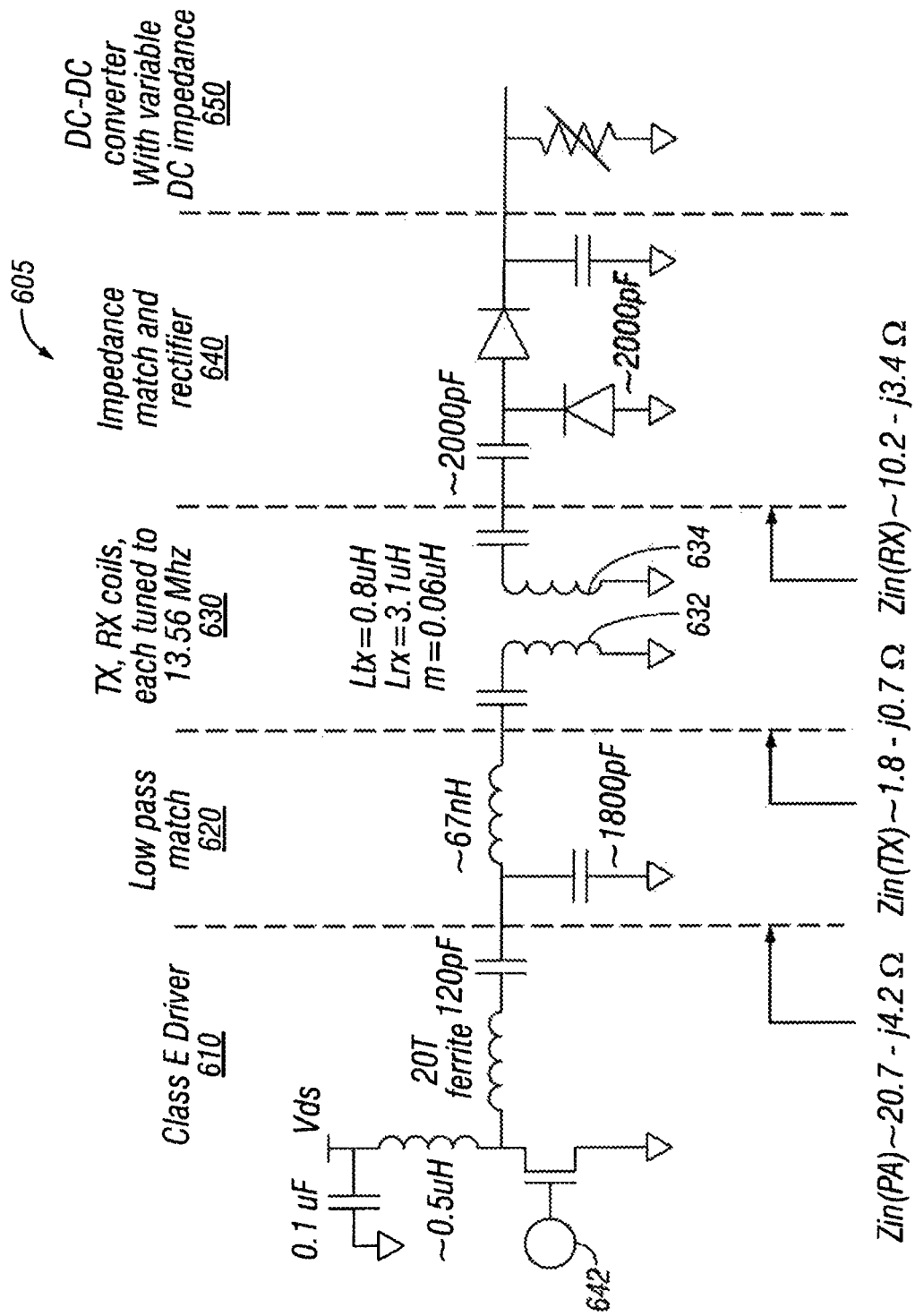
FIG. 32 illustrates one embodiment of transmit circuitry and receive circuitry that can be used with the present invention.

FIG. 32 shows a schematic of transmit circuitry and receive circuitry showing coupling there between and an adjustable DC load 650. As shown in FIG. 32, a charging system 605 can be characterized by a coupled coil transformer model 630 where the transmitter electronics are connected to a primary coil 632 (i.e., a transmit antenna) and the rectifier/regulator electronics on the receiver side are connected to a secondary coil 634 (i.e., a receive antenna).

A driver 610 generates an oscillating signal at a desired resonance frequency, such as, for example, about 13.56 MHz. As one example, this driver 610 can be configured as a class E driver as illustrated in FIG. 32. A low pass matching circuit 620 filters and impedance matches the signal from the driver 610 to the transmit antenna 632 of the coupled coil transformer model 630.

Energy is transferred through near field radiation to the receive antenna 634 of the coupled coil transformer model 630. The oscillating signal coupled to the receive antenna 634 is coupled to an impedance match and rectifier circuit 640 to provide an AC impedance match for the receive antenna 634 and rectify the oscillating signal to a substantially DC signal. A DC-to-DC converter 650 converts the DC signal from the rectifier 640 to a DC output useable by circuitry on a receiver device (not shown). The DC-to-DC converter 650 is also configured to adjust the DC impedance seen by the rectifier 640, which in turn adjusts the overall AC impedance of the input to the rectifier 640. As a result, changes in the DC impedance at the input of the DC-to-DC converter 650 can create a better match to the impedance of the receive antenna 634 and better mutual coupling between the receive antenna 634 and the transmit antenna 632.

The self inductances (Ltx and Lrx), mutual inductance (m), and loss resistances of the transformer model 630 can be derived from the measured or simulated coupling characteristics of the antenna pair.

It can be shown that given the mutual inductance (m), and the resistive losses, R1 and R2 of the transmit and receive antennas, respectively, there is an optimum load for the receive antenna that will maximize power transfer efficiency. This optimal load can be defined as:

$R \text{ eff} = R1*[1+(\text{omega}*m)2/(R1*R2)]5.$

Typically, Reff can be in a range from 1 to 20 ohms. Through the use of DC load control, the RF load seen by the receive coil 634 can be set to its most efficient value, as the mutual inductance (m) varies due to the reasons described above.

Another use for controlling the RF load is that a variation in load can be used to control the power delivered to the receiver device. This can be at the expense of some efficiency, but enables the maximum use of available power when serving a mix of wireless devices in various charge states.

In one embodiment, RF load can be used to widen the bandwidth of the transfer function, a result which depends on the matching network 620 between a very low impedance, or reactive impedance, transmit power amplifier 610, typical for wireless changing amplifiers, and the transmitting antenna 632. This bandwidth adjustment can work best over a large variation in the mutual inductance (m) and load if the input matching circuit includes a third tuned inductance (not shown), mutually coupled to the TX antenna 632. In this case, the bandwidth will increase linearly with increasing RF load resistance if the power amplifier has a very low source impedance.

This input series tuned DC-to-DC converter 650 results in a second impedance inversion, the first being between the transmit and receive antennas (632 and 634). As a result, when the load impedance increases the input impedance increases. This allows the load to "cloak" the receiver from the transmitter simply by raising the load impedance of the receiver.

Without this cloaking feature, the load from the receiver would have to present a short in order to cloak, using a mechanism such as element 312 discussed above with reference to FIG. 31. As a result, a charging pad with no receiver device present would appear as a highly tuned short circuit rather than an open circuit. Furthermore, when multiple uncloaked loads are present the total input conductance for the transmit antenna 632 will be the sum of the individual conductance's of the receive antennas 634 and power will be distributed according to their relative value.

Figure 33A:
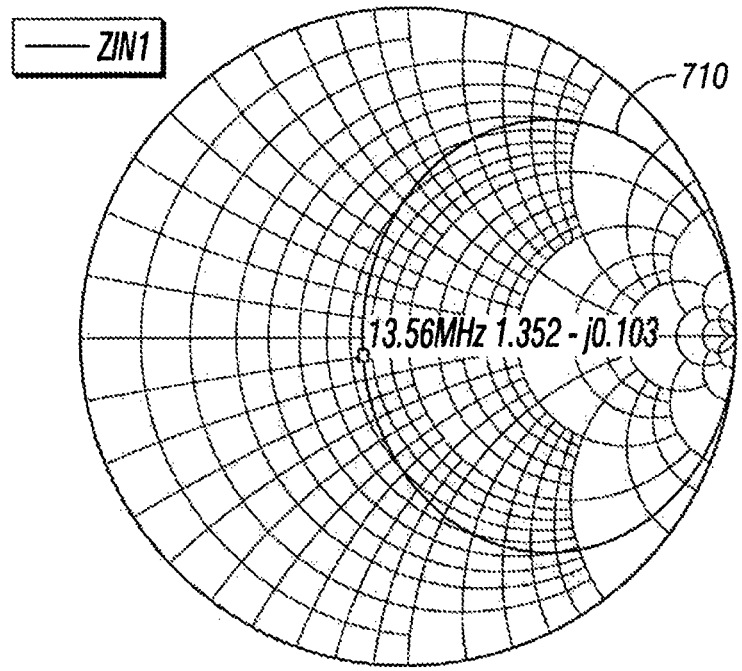
FIGS. 33(a) and 33(b) show Smith charts illustrating change in input impedance of a coupled coil pair responsive to a change in DC impedance at the receiver device.
Figure 33B:
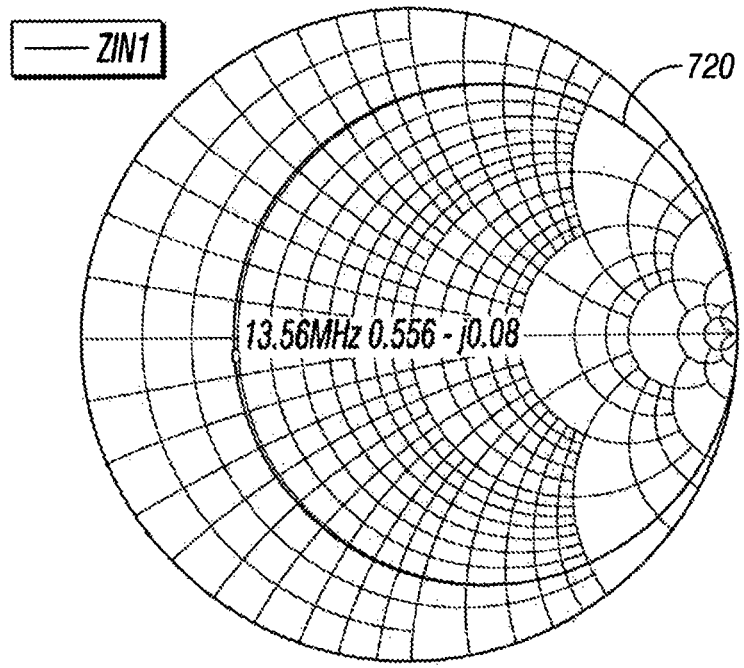

FIGS. 33(a) and 33(b) show Smith charts illustrating change in input impedance of a coupled coil pair (no inductive match added) responsive to a change in DC impedance at the receiver device. In FIGS. 33(a) and 33(b), the darkened circles 710 and 720, respectively, indicate constant resistance circles.

Referring to FIGS. 33(a) and 33(b), a DC impedance Rdc of about 10.2 ohms at the input to the DC-to-DC converter 650 results in a complex input impedance at the transmit antenna 632 of about 50 ohms and very little reactance. Referring to FIGS. 33(a) and 32, a DC impedance Rdc of about 80 ohms at the input to the DC-to-DC converter 650 results in a complex input impedance at the transmit antenna 632 of much less than 50 ohms, with very little reactance.

Figure 34A:
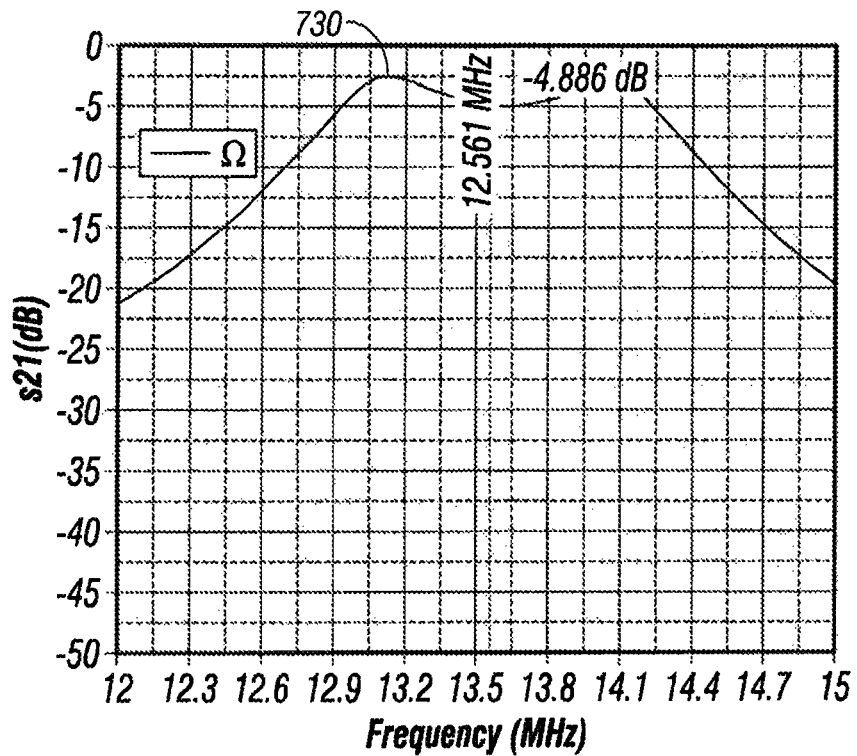
FIGS. 34(a) and 34(b) are amplitude plots showing improved coupling between a coupled coil pair responsive to a change in DC impedance at the receiver device in one embodiment of the present invention.
Figure 34B:
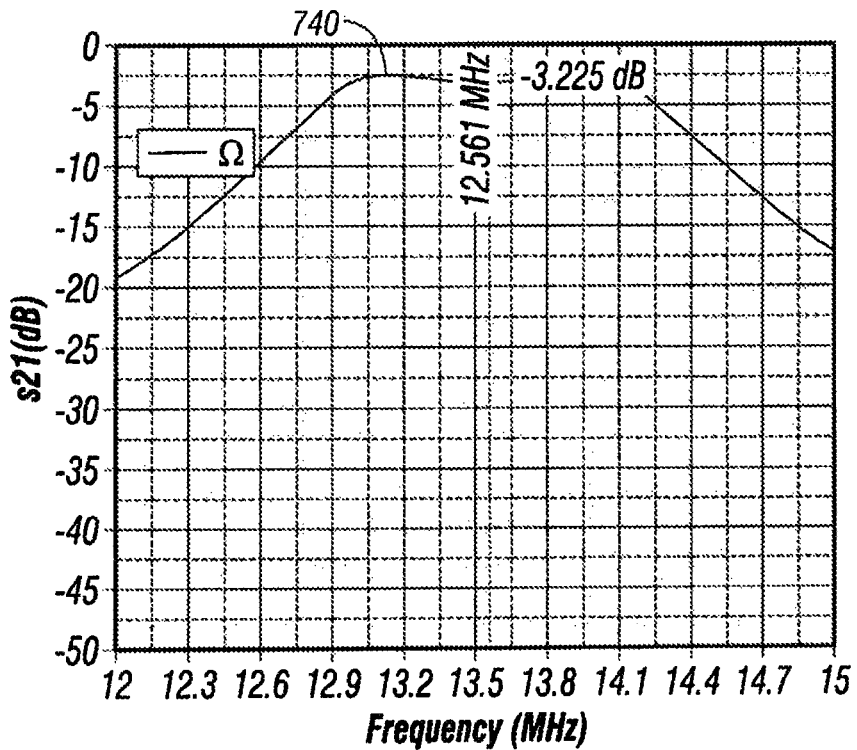

FIGS. 34(a) and 34(b) show amplitude plots (730 and 740, respectively) show improved coupling between a coupled coil pair responsive to a change in DC impedance at the receiver device. In FIG. 34(a) the amplitude at the center frequency of 13.56 MHz is about −4.886 dB. After adjusting the input impedance to the DC-to-DC converter 450 (FIG. 32), the amplitude at the center frequency of 13.56 MHz is improved to about −3.225 dB resulting in better coupling between the receive antenna and the transmit antenna, which results in more power transferred to the receive antenna.

Figure 35A:
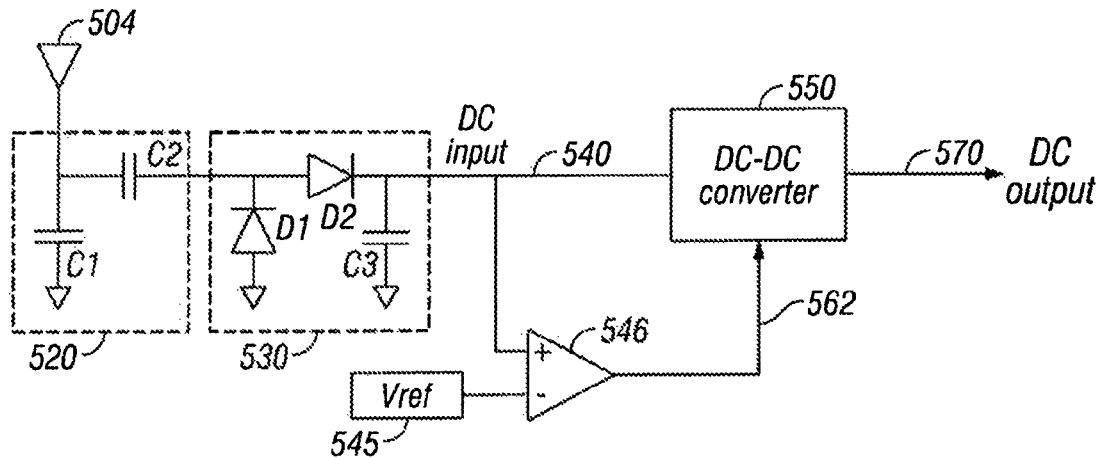
FIGS. 35(a) and 35(b) are schematics of receiver devices for adjusting DC impedance at the receiver device in one embodiment of the present invention.
Figure 35B:
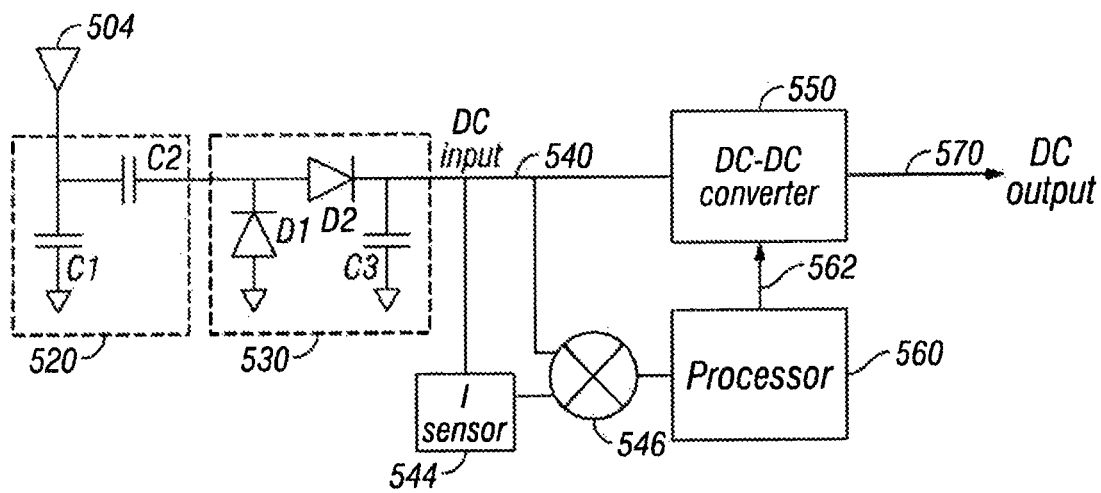

FIGS. 35(a) and 35(b) show simplified schematics of receiver devices illustrating exemplary embodiments for adjusting DC impedance at the receiver device. In both FIGS. 9A and 9B, the receive antenna 504 feeds an exemplary impedance matching circuit 520 including capacitors C1 and C2. An output from the impedance matching circuit 520 feeds a simple rectifier 530 (as one example) including diodes D1 and D2 and capacitor C3 for converting the RF frequency to a DC voltage. Of course, many other impedance matching circuits 520 and rectifiers 530 are contemplated as within the scope of embodiments of the present invention. A DC-to-DC converter 550 converts the DC input signal 540 from the rectifier to a DC output signal 570 suitable for use by a receiver device (not shown).

FIG. 35(a) illustrates a simple apparatus for maintaining an optimal power point impedance in a wireless power transmission system. A comparator, 548 compares the DC input signal 540 to a voltage reference 545, which is selected such that for a given expected power, the impedance as seen by the transmitter will result in the maximum amount of power coupled to the DC output signal 570. The output 561 of the comparator 548 feeds the DC-to-DC converter 550 with a signal to indicate whether the DC-to-DC converter 550 should increase or decrease its input DC impedance. In embodiments that use a switching DC-to-DC converter 550, this output of the comparator 561 can be converted to a pulse-width-modulation (PWM) signal, which adjusts the input DC impedance, as is explained below. This input voltage feedback circuit regulates input DC impedance by increasing the PWM pulse width as the voltage increases, thus decreasing impedance and voltage.

FIG. 35(b) an apparatus that can be used for maintaining an optimal power point impedance in a wireless power transmission system. In FIG. 35(b), a current sensor 544 can be included and a multiplexer 546 can be used to switch whether voltage or current at the DC input signal 540 is sampled by a processor 560 at any given time. In this system, voltage (Vr) and current (Ir) of the DC input signal 540 is measured, and a PWM signal 562 to the DC-to-DC converter 550 can be varied over a pre-allowed range. The processor 560 can determine which pulse width for the PWM signal 562 produces the maximum power (i.e., current times voltage), which is an indication of the best DC input impedance. This determined pulse width can be used for operation to transfer an optimal amount of power to the DC output signal 570. This sample and adjust process can be repeated as often as desired to track changing coupling ratios, transmit powers or transmit impedances.

DC impedance is defined by (voltage/current). Therefore, at any given current and desired impedance, there exists a desired voltage=(current*desired impedance). With a PWM converter, this desired voltage (and as a result desired impedance) can be achieved by providing a feedback term that compares the input voltage to the (current*desired impedance) term, and adjusts the pulse width up or down to maintain that term.

Figure 36A:
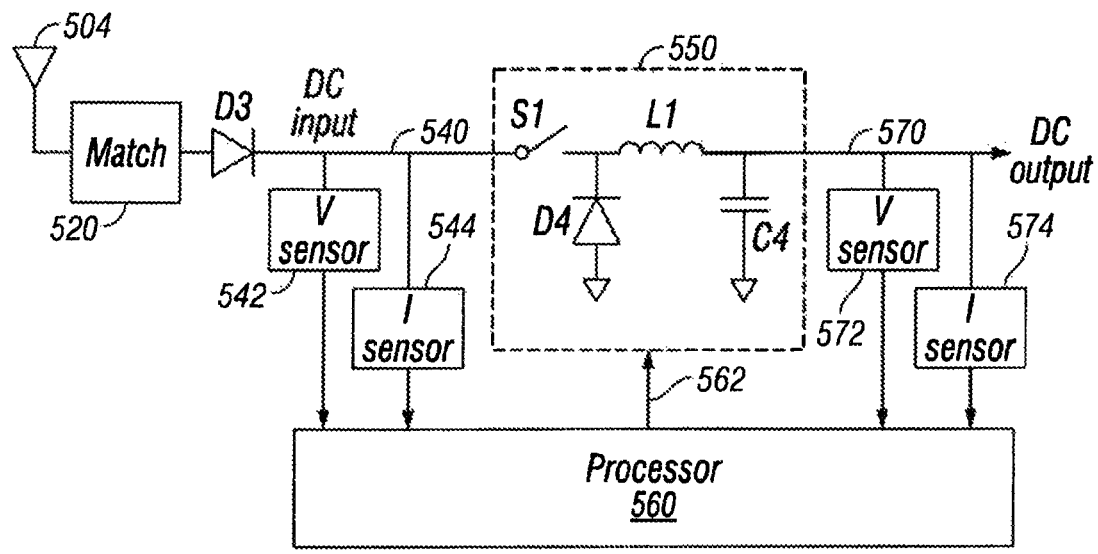
FIGS. 36(a) through 36(b) are schematics of receiver devices illustrating embodiments for adjusting DC impedance at the receiver device using a pulse-width modulation converter of the present invention.
Figure 36B:
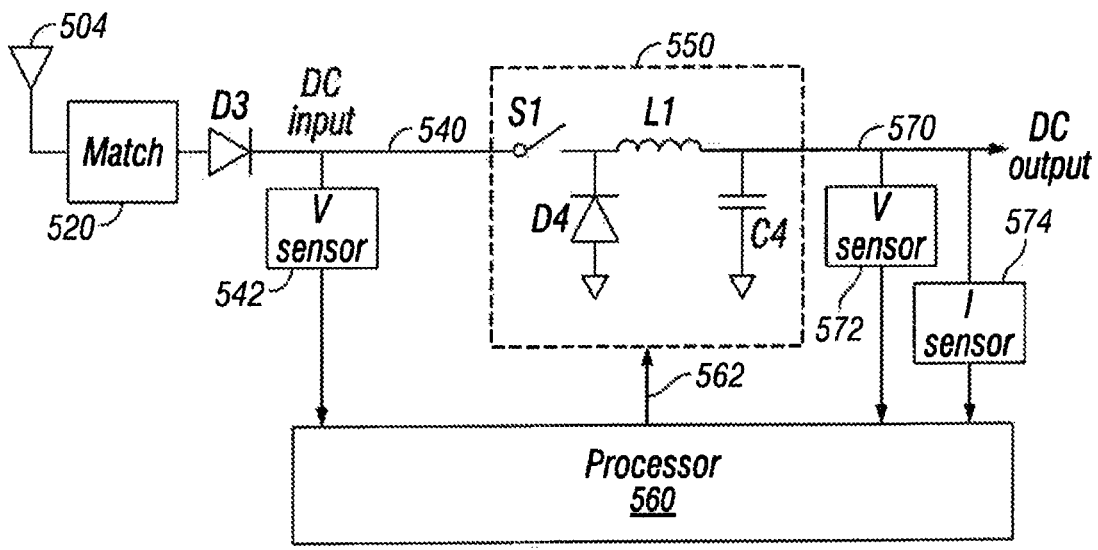

FIGS. 36(a) through 36(b) illustrate simplified schematics of receiver devices illustrating exemplary embodiments for adjusting DC impedance at the receiver device using a pulse-width modulation converter. In FIGS. 10A-10D, common elements include the receive antenna 504 feeding an impedance matching circuit 520. An output from the impedance matching circuit 520 feeds a simple rectifier, which is shown simply as diode D3. Of course, many other impedance matching circuits 520 and rectifiers are contemplated as within the scope of embodiments of the present invention. A DC-to-DC converter 550 converts the DC input signal 540 from the rectifier to a DC output signal 570 suitable for use by a receiver device (not show). A processor 560 samples parameters of the DC input signal 540, the DC output signal 270, or a combination thereof and generates a PWM signal 562 for the DC-to-DC converter 550.

The DC-to-DC converter 550 is a switch-mode converter wherein the PWM signal 562 controls a switch S1 to periodically charge a filtering circuit including diode D4, inductor L1, and capacitor C4. Those of ordinary skill in the art will recognize the DC-to-DC converter 550 as a buck converter, which converts a voltage on the DC input signal 540 to a lower voltage on the DC output signal 570. While not shown, those of ordinary skill in the art will also recognize that the switch-mode DC-to-DC converter 550 can also be implemented as a boost converter to generate a DC output signal 570 with a voltage that is higher the voltage on the DC input signal 540.

In most cases, a requirement to regulate the output voltage of the wireless power receiver will be most important. For battery charging, for example, it is often critical to not exceed a maximum output current or a maximum output voltage. This means that often the output voltage control term will dominate the control rules for the pulse width of the PWM signal 562.

In one embodiment, DC impedance control uses a feedback term in the switch-mode DC-to-DC converter 550 to effectively simulate a steady-state DC resistance in the receiver. In other words, the DC impedance is controlled by adjusting the frequency or duty cycle of the PWM signal 562 to the switch-mode DC-to-DC converter 550 to simulate a given DC impedance.

Feedback for the system is created by sampling one or more characteristics of the DC input signal 540, the DC output signal 570, or a combination thereof by a processor 560. The processor 560 then uses this sampled information, possibly along with other information such as expected power transfer and efficiency of the DC-to-DC converter 550 to adjust the PWM signal 562, which adjust the DC input signal and the DC output signal to close the feedback loop.

Individual differences of what is sampled and how the parameters of the PWM signal are generated are discussed with reference to four different exemplary embodiments illustrated as FIGS. 10A-10D.

In FIG. 36(a), the processor 560 samples a voltage of the DC input signal 540, a current of the DC input signal 540, a voltage of the DC output signal 570, and a current of the DC output signal 570.

In some embodiments, a voltage sensor 542 can be used between the DC input signal 540 and the processor 560. Similarly, a voltage sensor 572 can be used between the DC output signal 570 and the processor 560. In other embodiments the voltage sensors 542 and 572 may not be needed and the processor 460 can directly sample voltages on the DC input signal 540 and the DC output signal 570.

In some embodiments, a current sensor 544 can be used between the DC input signal 540 and the processor 560. Similarly, a current sensor 574 can be used between the DC output signal 570 and the processor 560. In other embodiments the current sensors 544 and 574 may not be needed and the processor 560 can directly sample current on the DC input signal 540 and the DC output signal 570.

With current and voltage measurements of both the DC input signal 540 and the DC output signal 570, the processor 560 can determine all the parameters needed for the power conversion system. Power-in on the DC input signal 540 can be determined as voltage-in times current-in. Power-out on the DC output signal 570 can be determined as voltage-out times current-out. Efficiency of the DC-to-DC converter 550 can be determined as a difference between power-out and power-in. The DC impedance of the DC input signal 540 can be determined as voltage-in divided by current-in.

The processor 560 can periodically sample all of the inputs (e.g., about once every second, or other suitable period) to determine power output at that time. In response, the processor 560 can change the duty cycle of the PWM signal 562, which will change the DC impedance of the DC input signal 540. For example, a narrow pulse width on the PWM signal 562 allows the input voltage to stay relatively high and the input current to stay relatively low, which leads to a higher DC impedance for the DC input signal 540. Conversely, a wider pulse width on the PWM signal 562 allows more current to be drawn from the DC input signal 540, resulting in a lower input voltage and a lower DC impedance for the DC input signal 540.

The periodic sampling and adjusting creates the feedback loop that can find an optimal DC impedance for the DC input signal 540, and as a result, an optimal power for the DC output signal 570. Details of finding these values are discussed below with reference to FIG. 37.

In FIG. 36(*b*), the processor 560 samples a voltage of the DC input signal 540, a voltage of the DC output signal 570, and a current of the DC output signal 570. As explained above with reference to FIG. 36(*c*), the voltage sensor 542, the voltage sensor 572, and the current sensor 574 can be included between their respective signals and the processor 560 depending on the embodiment.

As with FIGS. 36(*c*) and 36(*d*), power-out on the DC output signal 570 can be determined as voltage-out times current-out. In many cases, the efficiency of the DC-to-DC converter 550 will be known and relatively constant over the desired operating range. Thus, the processor 560 can estimate power-in on the DC input signal 540 based on power-out and an estimation of efficiency at the current operation point for the DC-to-DC converter 550. With power-in estimated, and voltage-in measured, the DC impedance of the DC input signal 540 can be determined. Once again, the periodic sampling and adjusting creates the feedback loop that can find an optimal DC impedance for the DC input signal 540, and as a result, an optimal power for the DC output signal 570.

In FIG. 36(*c*), the processor 560 samples a voltage of the DC input signal 540 and a current of the DC input signal 540. As explained above with reference to FIG. 36(*c*), the voltage sensor 542 and the current sensor 544 can be included between the DC input signal 540 and the processor 560 depending on the embodiment.

In FIG. 36(*c*), power-in on the DC input signal 540 can be determined as voltage-in times current-in and the DC impedance of the DC input signal 540 can be determined as voltage-in divided by current-in. As with FIG. 36(*d*), in FIG. 36(*c*) the efficiency of the DC-to-DC converter 550 will be known and relatively constant over the desired operating range. Thus, the processor 560 can estimate power-out on the DC output signal 570 based on power-in and an estimation of efficiency at the current operation point for the DC-to-DC converter 550. Once again, the periodic sampling and adjusting creates the feedback loop that can find an optimal DC impedance for the DC input signal 540, and as a result, an optimal power for the DC output signal 570.

In FIG. 36(*d*), the processor 560 samples only voltage of the DC input signal 540. As explained above with reference to FIG. 36(*c*), the voltage sensor 542 can be included between the DC input signal 540 and the processor 560 depending on the embodiment.

In FIG. 36(*d*), a pre-determined estimate can be made as to how much power is expected to be received through the receive antenna and rectifier and delivered on the DC input signal. Using this pre-determined estimate DC impedance of the DC input signal 540 can be determined relative to the voltage-in. As with FIG. 36(*d*), in FIG. 36(*c*) the efficiency of the DC-to-DC converter 550 will be known and relatively constant over the desired operating range. Thus, the processor 560 can estimate power-out on the DC output signal 570 based on the pre-determined power-in estimate and an estimation of efficiency at the current operation point for the DC-to-DC converter 550. Once again, the periodic sampling and adjusting creates the feedback loop that can find an optimal DC impedance for the DC input signal 540, and as a result, an optimal power for the DC output signal 570.

The pre-determined power estimate can be a fixed value programmed in to the receiver device or can be communicated to the receiver device from the transmitter device, which include a mechanism for determining how much of the power transmitted will be coupled to that particular receiver device.

Figure 37A:
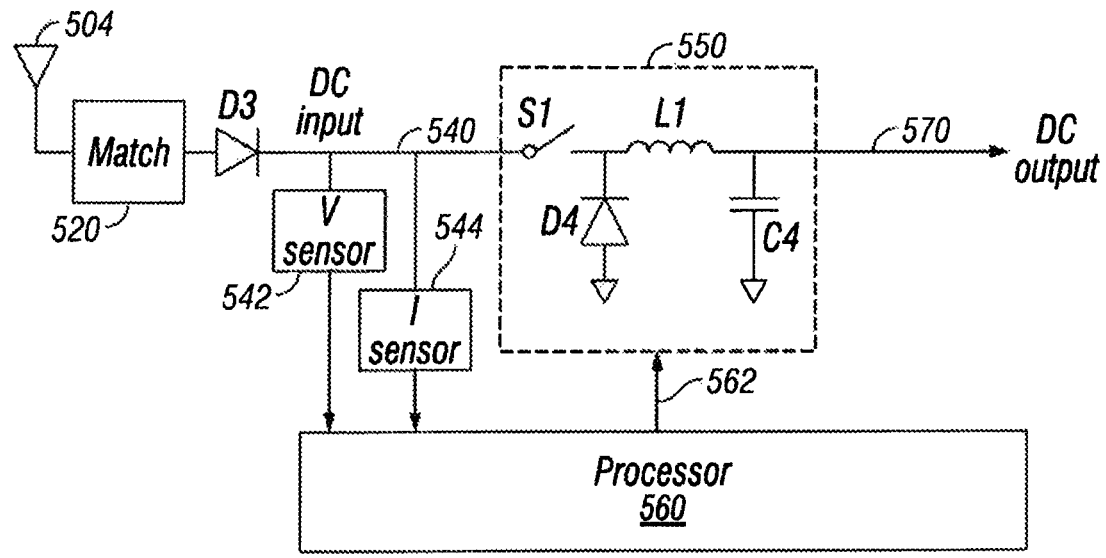
FIG. 37 illustrates various input and output parameters that can be used when adjusting DC impedance at the receiver device.
Figure 37B:
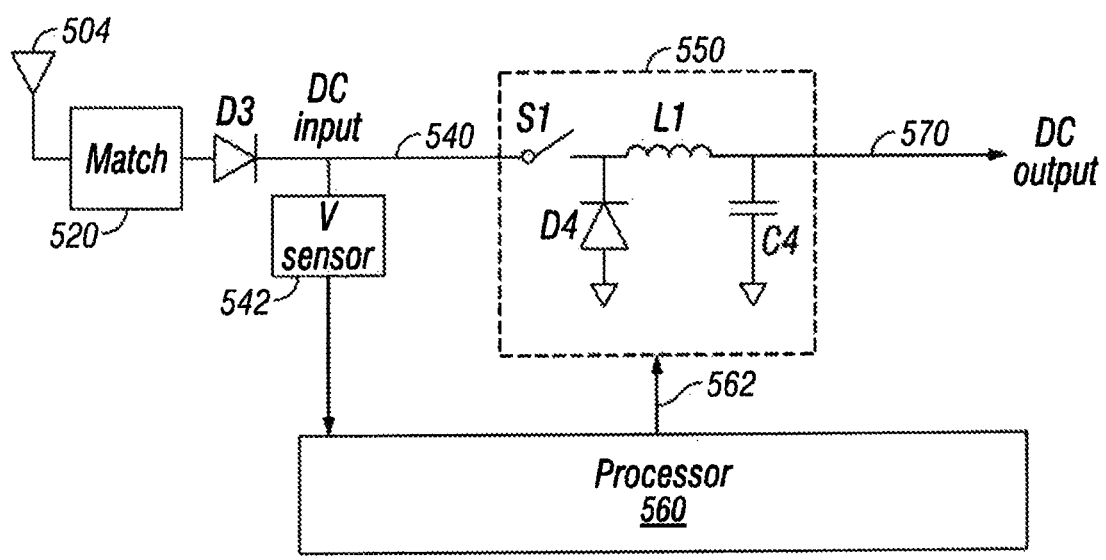

FIG. 37 illustrates various input and output parameters that can be used when adjusting DC impedance at the receiver device. This graph represents a system that has a specific source impedance, but where a load resistor is allowed to vary over a wide range. This load resistor is represented as the variable resistor of the DC-to-DC converter 650 of FIG. 32. Alternatively, the load resistor can be represented by the DC impedance of the DC input signal 540 to the DC-to-DC converter 550 shown in FIGS. 35(*a*)-35(*d*).

In FIG. 37, a 50 ohm source impedance is driven by a signal with a 1:1 source-to-load coupling. Line 820 shows the current through the load resistor. Notice as the load impedance increases, the current decreases due to Ohm's Law. Line 810 shows the voltage across the load resistor. Notice that as the load impedance increases, the voltage increases as well per the resistor divider equation.

These two data sets for current and voltage of the load resistor give the power across the load resistor, as shown by line 840. Note that the power peaks at a certain load impedance. In this case (1:1 load coupling) this maximum power point occurs when the load impedance equals, or is near, the source impedance. If the coupling is different, the peak power point can be shifted as well.

Line 850 represents a PWM setting (out of 100) that has an inverse relationship to output impedance. This is the function exhibited by most buck converters. As can be seen, there is one ideal PWM setting that maximizes power received by the load resistor. Wireless power impedance control schemes used with reference to exemplary embodiments discussed herein attempt to discover and maintain this ideal PWM setting.

In some embodiments, as in FIGS. 32, and 35(*a*) through 35(*d*), the DC impedance of the DC input signal 540, and as a result the AC impedance of the receive antenna can be effectively de-tuned from optimal power transfer to limit the amount of power delivered on the DC output signal 570. This limiting of power can be useful where the receiver device cannot accept the maximum power deliverable from the DC-to-DC converter 550.

The various illustrative logical blocks, modules, and circuits described in connection with the exemplary embodiments disclosed herein can be implemented or performed with a general purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the exemplary embodiments disclosed herein can be embodied directly in hardware, in a software module executed by a processor, or in a combination of the two. A software module can reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of storage medium known in the art. An exemplary storage medium is coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

In various embodiments, the functions described can be implemented in hardware, software, firmware, or any combination thereof. If implemented in software, the functions can be stored on or transmitted over as one or more instructions or code on a computer-readable medium. Computer-readable media includes both computer storage media and communication media including any medium that facilitates transfer of a computer program from one place to another. A storage media can be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

Figure 38:
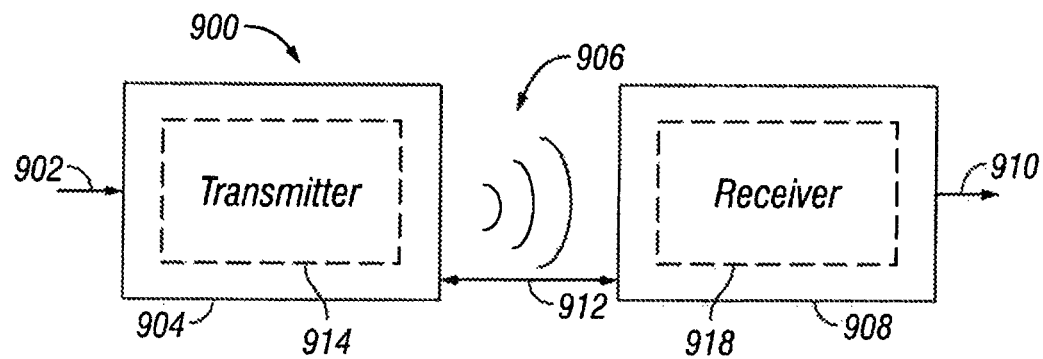
FIG. 38 shows a simplified block diagram of a wireless power transfer system.

FIG. 38 illustrates wireless transmission or charging system 900, in accordance with various exemplary embodiments of the present invention. Input power 902 is provided to a transmitter 904 for generating a radiated field 906 for providing energy transfer. A receiver 908 couples to the radiated field 906 and generates an output power 910 for storing or consumption by a monitoring device 10 coupled to the output power 910. Both the transmitter 904 and the receiver 908 are separated by a distance 912. In one exemplary embodiment, transmitter 904 and receiver 908 are configured according to a mutual resonant relationship and when the resonant frequency of receiver 908 and the resonant frequency of transmitter 904 are exactly identical, transmission losses between the transmitter 904 and the receiver 908 are minimal when the receiver 908 is located in the "near-field" of the radiated field 906.

Transmitter 904 further includes a transmit antenna 914 for providing a means for energy transmission and receiver 908 further includes a receive antenna 918 for providing a means for energy reception. The transmit and receive antennas are sized according to applications and monitoring devices 10 to be associated therewith. As stated, an efficient energy transfer occurs by coupling a large portion of the energy in the near-field of the transmitting antenna to a receiving antenna rather than propagating most of the energy in an electromagnetic wave to the far field. When in this near-field a coupling mode may be developed between the transmit antenna 914 and the receive antenna 918. The area around the antennas 914 and 918 where this near-field coupling may occur is referred to herein as a coupling-mode region.

Figure 39:
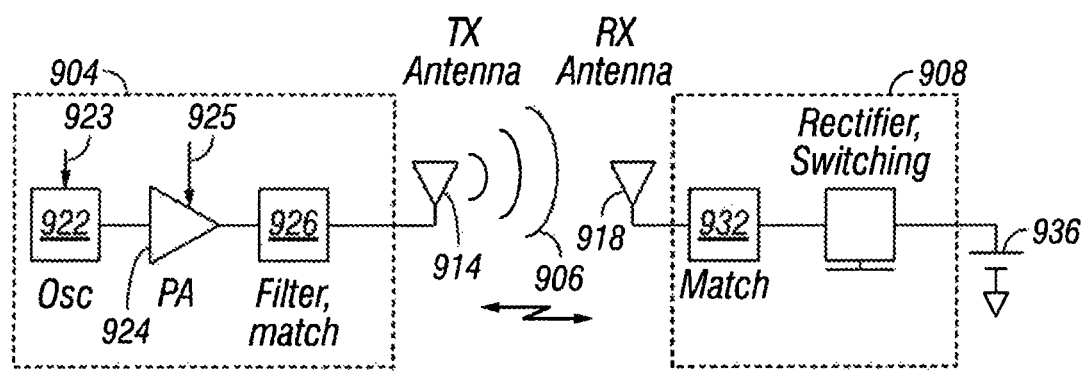
FIG. 39 shows a simplified schematic diagram of a wireless power transfer system.

FIG. 39 shows a simplified schematic diagram of a wireless power transfer system. The transmitter 904 includes an oscillator 922, a power amplifier 924 and a filter and matching circuit 926. The oscillator is configured to generate at a desired frequency, which may be adjusted in response to adjustment signal 923. The oscillator signal may be amplified by the power amplifier 924 with an amplification amount responsive to control signal 925. The filter and matching circuit 926 may be included to filter out harmonics or other unwanted frequencies and match the impedance of the transmitter 904 to the transmit antenna 914.

The receiver may include a matching circuit 932 and a rectifier and switching circuit to generate a DC power output to charge a battery 936 as shown in FIG. 2 or power a monitoring device 10 coupled to the receiver (not shown). The matching circuit 932 may be included to match the impedance of the receiver 908 to the receive antenna 918.

Figure 40:
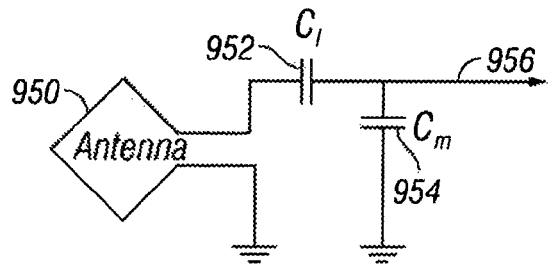
FIG. 40 shows a schematic diagram of a loop antenna for use in exemplary embodiments of the present invention.

As illustrated in FIG. 40, antennas used in exemplary embodiments may be configured as a "loop" antenna 950, which may also be referred to herein as a "magnetic" antenna. Loop antennas may be configured to include an air core or a physical core such as a ferrite core. Air core loop antennas may be more tolerable to extraneous physical devices placed in the vicinity of the core. Furthermore, an air core loop antenna allows the placement of other components within the core area. In addition, an air core loop may more readily enable placement of the receive antenna 918 within a plane of the transmit antenna 914 where the coupled-mode region of the transmit antenna 914 may be more powerful, FIG. 39.

As stated, efficient transfer of energy between the transmitter 904 and receiver 908 occurs during matched or nearly matched resonance between the transmitter 904 and the receiver 908. However, even when resonance between the transmitter 904 and receiver 908 are not matched, energy may be transferred at a lower efficiency. Transfer of energy occurs by coupling energy from the near-field of the transmitting antenna to the receiving antenna residing in the neighborhood where this near-field is established rather than propagating the energy from the transmitting antenna into free space.

The resonant frequency of the loop or magnetic antennas is based on the inductance and capacitance. Inductance in a loop antenna is generally simply the inductance created by the loop, whereas, capacitance is generally added to the loop antenna's inductance to create a resonant structure at a desired resonant frequency. As a non-limiting example, capacitor 952 and capacitor 954 may be added to the antenna to create a resonant circuit that generates resonant signal 956. Accordingly, for larger diameter loop antennas, the size of capacitance needed to induce resonance decreases as the diameter or inductance of the loop increases. Furthermore, as the diameter of the loop or magnetic antenna increases, the efficient energy transfer area of the near-field increases. Of course, other resonant circuits are possible. As another non-limiting example, a capacitor may be placed in parallel between the two terminals of the loop antenna. In addition, those of ordinary skill in the art will recognize that for transmit antennas the resonant signal 956 may be an input to the loop antenna 950.

Exemplary embodiments of the invention include coupling power between two antennas that are in the near-fields of each other. As stated, the near-field is an area around the antenna in which electromagnetic fields exist but may not propagate or radiate away from the antenna. They are typically confined to a volume that is near the physical volume of the antenna. In the exemplary embodiments of the invention, magnetic type antennas such as single and multi-turn loop antennas are used for both transmit (Tx) and receive (Rx) antenna systems since magnetic near-field amplitudes tend to be higher for magnetic type antennas in comparison to the electric near-fields of an electric-type antenna (e.g., a small dipole). This allows for potentially higher coupling between the pair. Furthermore, "electric" antennas (e.g., dipoles and monopoles) or a combination of magnetic and electric antennas is also contemplated.

The Tx antenna can be operated at a frequency that is low enough and with an antenna size that is large enough to achieve good coupling (e.g., >−4 dB) to a small Rx antenna at significantly larger distances than allowed by far field and inductive approaches mentioned earlier. If the Tx antenna is sized correctly, high coupling levels (e.g., −2 to −4 dB) can be achieved when the Rx antenna on a host device is placed within a coupling-mode region (i.e., in the near-field) of the driven Tx loop antenna.

Figure 41:
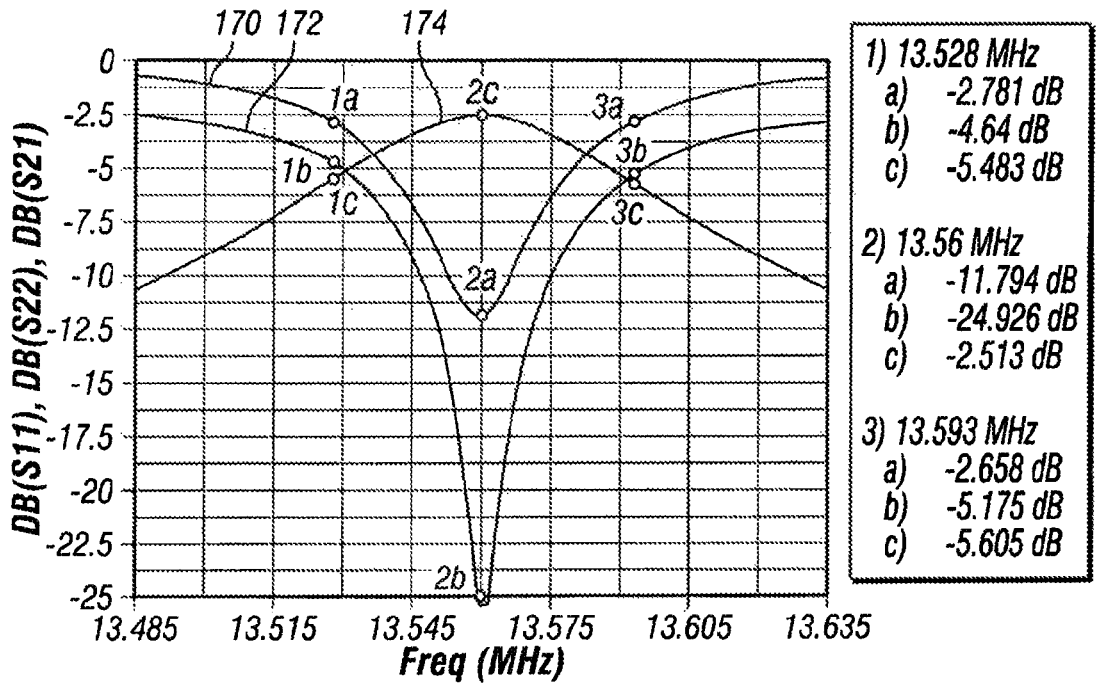
FIG. 41 shows simulation results indicating coupling strength between transmit and receive antennas.

FIG. 41 shows simulation results indicating coupling strength between transmit and receive antennas. In other words, with a large negative number there is a very close impedance match and most of the power is accepted and, as a result, radiated by the transmit antenna. Conversely, a small negative number indicates that much of the power is reflected back from the antenna because there is not a close impedance match at the given frequency. IN this embodiment, the transmit antenna and the receive antenna are tuned to have a resonant frequency of about 13.56 MHz.

At points 1*a* and 3*a*, corresponding to about 13.528 MHz and 13.593 MHz, much of the power is reflected and not transmitted out of the transmit antenna. However, at point 2*a*, corresponding to about 13.56 MHz, it can be seen that a large amount of the power is accepted and transmitted out of the antenna. At points 1*b* and 3*b*, corresponding to about 13.528 MHz and 13.593 MHz, much of the power is reflected and not conveyed through the receive antenna and into the receiver. However, at point 2*b* corresponding to about 13.56 MHz, it can be seen that a large amount of the power is accepted by the receive antenna and conveyed into the receiver. At points 1*c* and 3*c*, corresponding to about 13.528 MHz and 13.593 MHz, much of the power sent out of the transmitter is not available at the receiver because (1) the transmit antenna rejects much of the power sent to it from the transmitter and (2) the coupling between the transmit antenna and the receive antenna is less efficient as the frequencies move away from the resonant frequency. However, at point 2*c* corresponding to about 13.56 MHz, it can be seen that a large amount of the power sent from the transmitter is available at the receiver, indicating a high degree of coupling between the transmit antenna and the receive antenna.

FIGS. 42(*a*) and 42(*b*) show layouts of loop antennas for transmit and receive antennas according to exemplary embodiments of the present invention. Loop antennas may be configured in a number of different ways, with single loops or multiple loops at wide variety of sizes. In addition, the loops may be a number of different shapes, such as, for example only, circular, elliptical, square, and rectangular. FIG. 5A illustrates a large square loop transmit antenna 914S and a small square loop receive antenna 918 placed in the same plane as the transmit antenna 914S and near the center of the transmit antenna 914S. FIG. 5B illustrates a large circular loop transmit antenna 914C and a small square loop receive antenna 918' placed in the same plane as the transmit antenna 914C and near the center of the transmit antenna 914C. The square loop transmit antenna 914S has side lengths of "a" while the circular loop transmit antenna 914C has a diameter of 0.

FIG. 43 shows various placement points for a receive antenna relative to a transmit antenna to illustrate coupling strengths in coplanar and coaxial placements. "Coplanar," as used herein, means that the transmit antenna and receive antenna have planes that are substantially aligned (i.e., have surface normals pointing in substantially the same direction) and with no distance (or a small distance) between the planes of the transmit antenna and the receive antenna. "Coaxial," as used herein, means that the transmit antenna and receive antenna have planes that are substantially aligned (i.e., have surface normals pointing in substantially the same direction) and the distance between the two planes is not trivial and furthermore, the surface normal of the transmit antenna and the receive antenna lie substantially along the same vector, or the two normals are in echelon.

Figure 44:
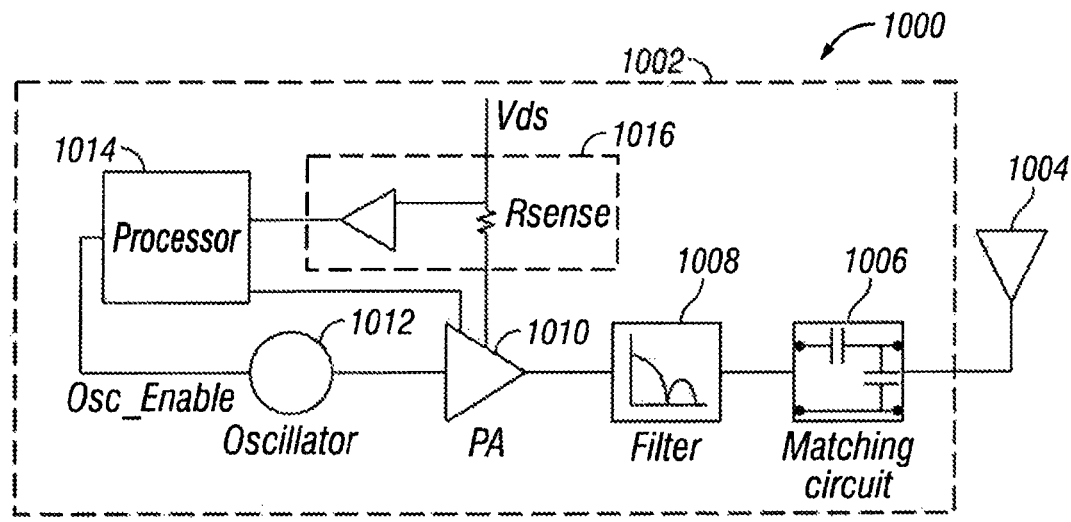
FIG. 44 is a simplified block diagram of a transmitter, in accordance with an exemplary embodiment of the present invention.

FIG. 44 is a simplified block diagram of a transmitter, in accordance with an exemplary embodiment of the present invention. A transmitter 1000 includes transmit circuitry 1002 and a transmit antenna 1004. Generally, transmit circuitry 1002 provides RF power to the transmit antenna 1004 by providing an oscillating signal resulting in generation of near-field energy about the transmit antenna 1004. By way of example, transmitter 1000 may operate at the 13.56 MHz ISM band. Exemplary transmit circuitry 1002 includes a fixed impedance matching circuit 1006 for matching the impedance of the transmit circuitry 1002 (e.g., 50 ohms) to the transmit antenna 1004 and a low pass filter (LPF) 1008 configured to reduce harmonic emissions to levels to prevent self-jamming of monitoring devices 10 coupled to receivers 108. Other exemplary embodiments may include different filter topologies, including but not limited to, notch filters that attenuate specific frequencies while passing others and may include an adaptive impedance match, that can be varied based on measurable transmit metrics, such as output power to the antenna or DC current draw by the power amplifier. Transmit circuitry 1002 further includes a power amplifier 1010 configured to drive an RF signal as determined by an oscillator 1012. The transmit circuitry may be comprised of discrete monitoring devices 10 or circuits, or alternately, may be comprised of an integrated assembly. An exemplary RF power output from transmit antenna 1004 may be on the order of 2.5 Watts.

Transmit circuitry 1002 further includes a processor 1014 for enabling the oscillator 1012 during transmit phases (or duty cycles) for specific receivers, for adjusting the frequency of the oscillator, and for adjusting the output power level for implementing a communication protocol for interacting with neighboring monitoring devices 10 through their attached receivers.

The transmit circuitry 1002 may further include a load sensing circuit 1016 for detecting the presence or absence of active receivers in the vicinity of the near-field generated by transmit antenna 1004. By way of example, a load sensing circuit 1016 monitors the current flowing to the power amplifier 1010, which is affected by the presence or absence of active receivers in the vicinity of the near-field generated by transmit antenna 1004. Detection of changes to the loading on the power amplifier 1010 are monitored by processor 1014 for use in determining whether to enable the oscillator 1012 for transmitting energy to communicate with an active receiver.

Transmit antenna 1004 may be implemented as an antenna strip with the thickness, width and metal type selected to keep resistive losses low. In a conventional implementation, the transmit antenna 1004 can generally be configured for association with a larger structure such as a table, mat, lamp or other less portable configuration. Accordingly, the transmit antenna 1004 generally will not need "turns" in order to be of a practical dimension. An exemplary implementation of a transmit antenna 1004 may be "electrically small" (i.e., fraction of the wavelength) and tuned to resonate at lower usable frequencies by using capacitors to define the resonant frequency. In an exemplary application where the transmit antenna 1004 may be larger in diameter, or length of side if a square loop, (e.g., 0.50 meters) relative to the receive antenna, the transmit antenna 1004 will not necessarily need a large number of turns to obtain a reasonable capacitance.

Figure 45:
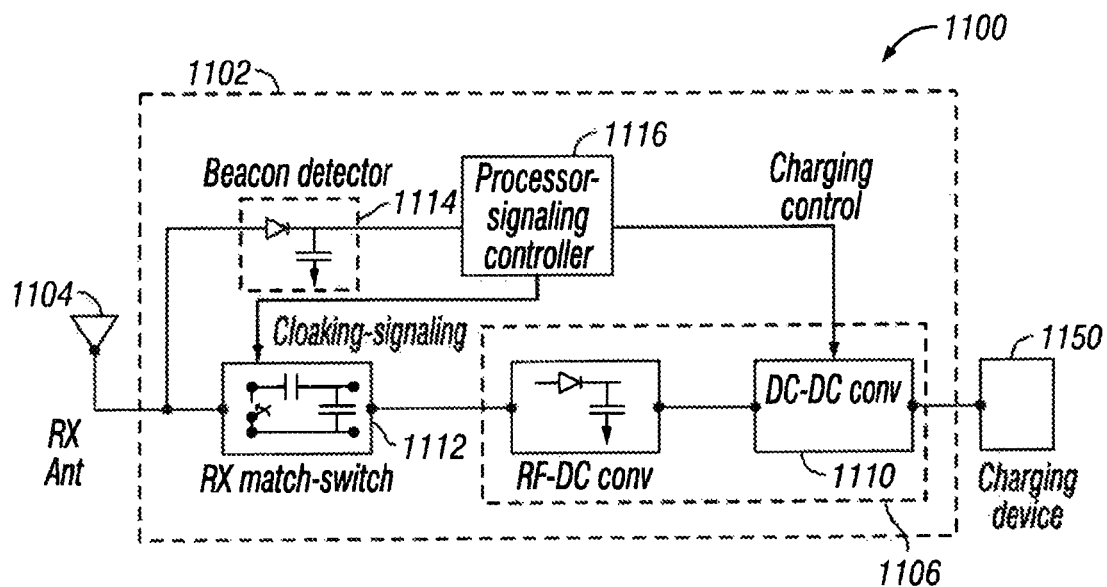
FIG. 45 is a simplified block diagram of a receiver, in accordance with an exemplary embodiment of the present invention.

FIG. 45 is a block diagram of a receiver, in accordance with an exemplary embodiment of the present invention. A receiver 1100 includes receive circuitry 1102 and a receive antenna 1104. Receiver 1100 further couples to monitoring device 10, hereafter monitoring device 1150 for providing received power thereto. It should be noted that receiver 1100 is illustrated as being external to monitoring device 1150 but may be integrated into monitoring device 1150. Generally, energy is propagated wirelessly to receive antenna 1104 and then coupled through receive circuitry 1102 to monitoring device 1150.

Receive antenna 1104 is tuned to resonate at the same frequency, or near the same frequency, as transmit antenna 1004, FIG. 44. Receive antenna 1104 may be similarly dimensioned with transmit antenna 1004 or may be differently sized based upon the dimensions of an associated monitoring device 1150. By way of example, monitoring device 1150 may be a portable electronic monitoring device having diametric or length dimension smaller that the diameter of length of transmit antenna 1004. In such an example, receive antenna 1104 may be implemented as a multi-turn antenna in order to reduce the capacitance value of a tuning capacitor (not shown) and increase the receive antenna's impedance. By way of example, receive antenna 1104 may be placed around the substantial circumference of monitoring device 1150 in order to maximize the antenna diameter and reduce the number of loop turns (i.e., windings) of the receive antenna and the inter-winding capacitance.

Receive circuitry 1102 provides an impedance match to the receive antenna 1104. Receive circuitry 1102 includes power conversion circuitry 1106 for converting a received RF energy source into charging power for use by monitoring device 1150. Power conversion circuitry 1106 includes an RF-to-DC converter 1108 and may also in include a DC-to-DC converter 1110. RF-to-DC converter 1108 rectifies the RF energy signal received at receive antenna 1104 into a non-alternating power while DC-to-DC converter 1110 converts the rectified RF energy signal into an energy potential (e.g., voltage) that is compatible with monitoring device 1150. Various RF-to-DC converters are contemplated including partial and full rectifiers, regulators, bridges, doublers, as well as linear and switching converters.

Receive circuitry 1102 may further include switching circuitry 1112 for connecting receive antenna 1104 to the power conversion circuitry 1106 or alternatively for disconnecting the power conversion circuitry 1106. Disconnecting receive antenna 1104 from power conversion circuitry 1106 not only suspends charging of monitoring device 1150, but also changes the "load" as "seen" by the transmitter 1000 (FIG. 10) as is explained more fully below. As disclosed above, transmitter 1000 includes load sensing circuit 1016 which detects fluctuations in the bias current provided to transmitter power amplifier 1010. Accordingly, transmitter 1000 has a mechanism for determining when receivers are present in the transmitter's near-field.

When multiple receivers 1100 are present in a transmitter's near-field, it may be desirable to time-multiplex the loading and unloading of one or more receivers to enable other receivers to more efficiently couple to the transmitter. A receiver may also be cloaked in order to eliminate coupling to other nearby receivers or to reduce loading on nearby transmitters. This "unloading" of a receiver is also known herein as a "cloaking" Furthermore, this switching between unloading and loading controlled by receiver 1100 and detected by transmitter 1000 provides a communication mechanism from receiver 1100 to transmitter 1000 as is explained more fully below. Additionally, a protocol can be associated with the switching which enables the sending of a message from receiver 1100 to transmitter 1000. By way of example, a switching speed may be on the order of 100 mu sec.

In an exemplary embodiment, communication between the transmitter and the receiver refers to a monitoring device sensing and charging control mechanism, rather than conventional two-way communication. In other words, the transmitter uses on/off keying of the transmitted signal to adjust whether energy is available in the near-filed. The receivers interpret these changes in energy as a message from the transmitter. From the receiver side, the receiver uses tuning and de-tuning of the receive antenna to adjust how much power is being accepted from the near-field. The transmitter can detect this difference in power used from the near-field and interpret these changes as a message from the receiver.

Receive circuitry 1102 may further include signaling detector and beacon circuitry 1114 used to identify received energy fluctuations, which may correspond to informational signaling from the transmitter to the receiver. Furthermore, signaling and beacon circuitry 1114 may also be used to detect the transmission of a reduced RF signal energy (i.e., a beacon signal) and to rectify the reduced RF signal energy into a nominal power for awakening either un-powered or power-depleted circuits within receive circuitry 1102 in order to configure receive circuitry 1102 for wireless charging.

Receive circuitry 1102 further includes processor 1116 for coordinating the processes of receiver 1100 described herein including the control of switching circuitry 1112 described herein. Cloaking of receiver 1100 may also occur upon the occurrence of other events including detection of an external wired charging source (e.g., wall/USB power) providing charging power to monitoring device 1150. Processor 1116, in addition to controlling the cloaking of the receiver, may also monitor beacon circuitry 1114 to determine a beacon state and extract messages sent from the transmitter. Processor 1116 may also adjust DC-to-DC converter 1110 for improved performance.

Figure 46:
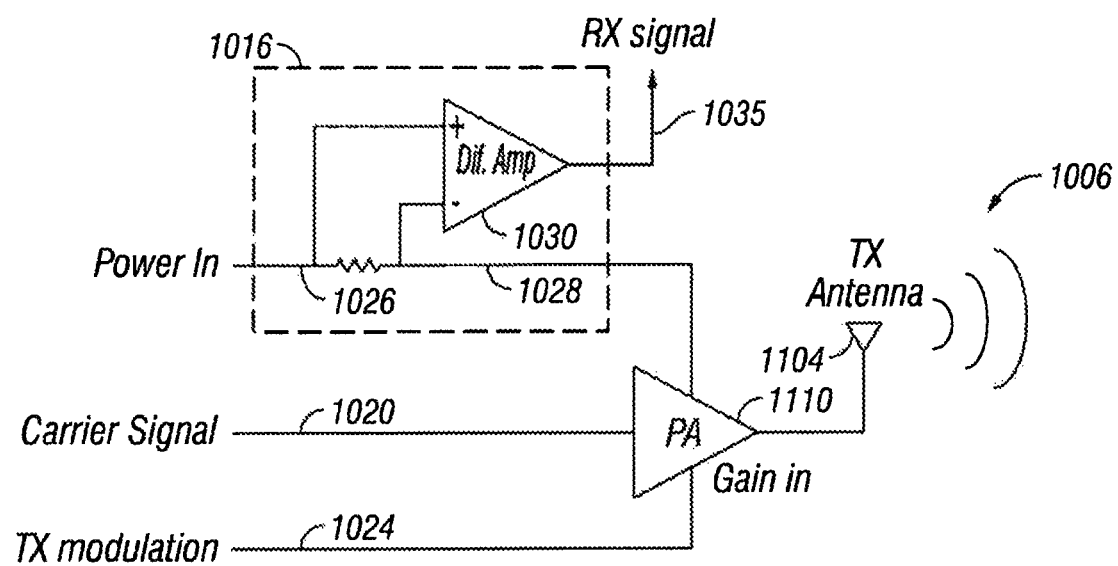
FIG. 46 shows a simplified schematic of a portion of transmit circuitry for carrying out messaging between a transmitter and a receiver.

FIG. 46 shows a simplified schematic of a portion of transmit circuitry for carrying out messaging between a transmitter and a receiver. In some exemplary embodiments of the present invention, a means for communication may be enabled between the transmitter and the receiver. In FIG. 9 a power amplifier 1010 drives the transmit antenna 1004 to generate the radiated field. The power amplifier is driven by a carrier signal 1020 that is oscillating at a desired frequency for the transmit antenna 1004. A transmit modulation signal 1024 is used to control the output of the power amplifier 1010.

The transmit circuitry can send signals to receivers by using an ON/OFF keying process on the power amplifier 1010. In other words, when the transmit modulation signal 1024 is asserted, the power amplifier 1010 will drive the frequency of the carrier signal 1020 out on the transmit antenna 1004. When the transmit modulation signal 1024 is negated, the power amplifier will not drive out any frequency on the transmit antenna 1004.

The transmit circuitry of FIG. 46 also includes a load sensing circuit 1016 that supplies power to the power amplifier 1010 and generates a receive signal 1035 output. In the load sensing circuit 1016 a voltage drop across resistor Rs develops between the power in signal 1026 and the power supply 1028 to the power amplifier 1010. Any change in the power consumed by the power amplifier 1010 will cause a change in the voltage drop that will be amplified by differential amplifier 1030. When the transmit antenna is in coupled mode with a receive antenna in a receiver (not shown in FIG. 9) the amount of current drawn by the power amplifier 1010 will change. In other words, if no coupled mode resonance exist for the transmit antenna 1010, the power required to drive the radiated field will be first amount. If a coupled mode resonance exists, the amount of power consumed by the power amplifier 1010 will go up because much of the power is being coupled into the receive antenna. Thus, the receive signal 1035 can indicate the presence of a receive antenna coupled to the transmit antenna 1035 and can also detect signals sent from the receive antenna, as explained below. Additionally, a change in receiver current draw will be observable in the transmitter's power amplifier current draw, and this change can be used to detect signals from the receive antennas, as explained below.

Figure 47A:
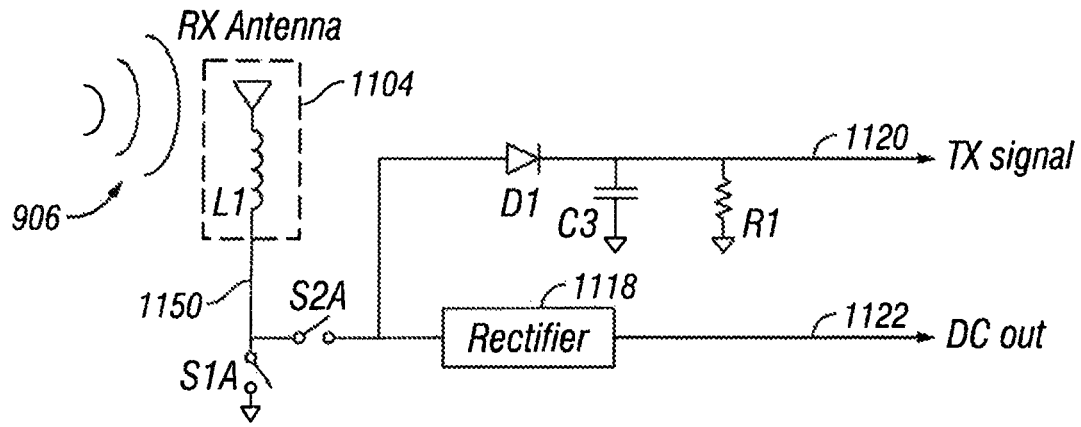
FIGS. 47(a) through 47(c) show a simplified schematic of a portion of receive circuitry in various states to illustrate messaging between a receiver and a transmitter.
Figure 47B:
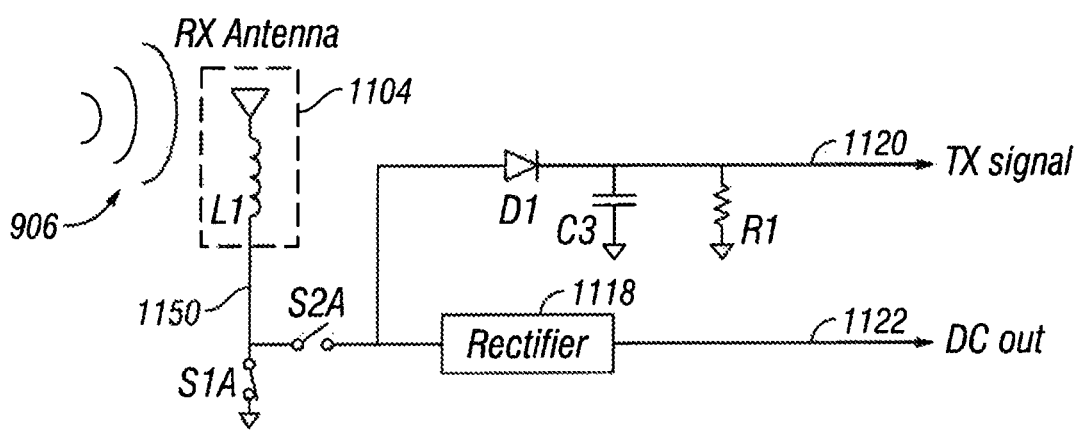
Figure 47C:
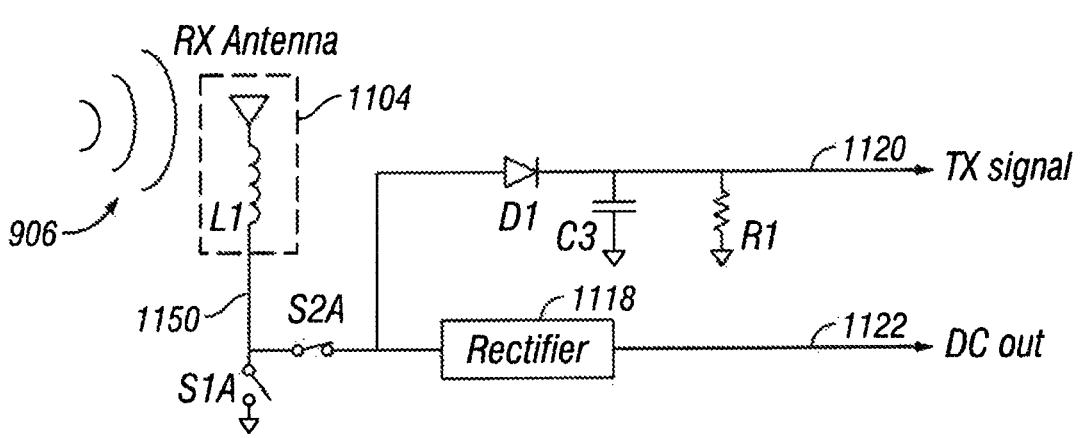
Figure 48A:
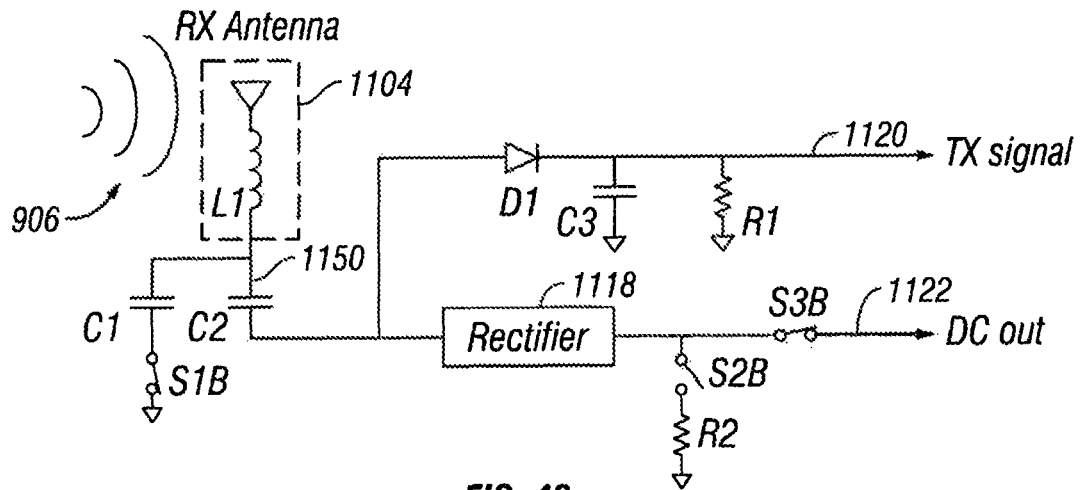
FIGS. 48(a) through 48(c) show a simplified schematic of a portion of alternative receive circuitry in various states to illustrate messaging between a receiver and a transmitter.
Figure 48B:
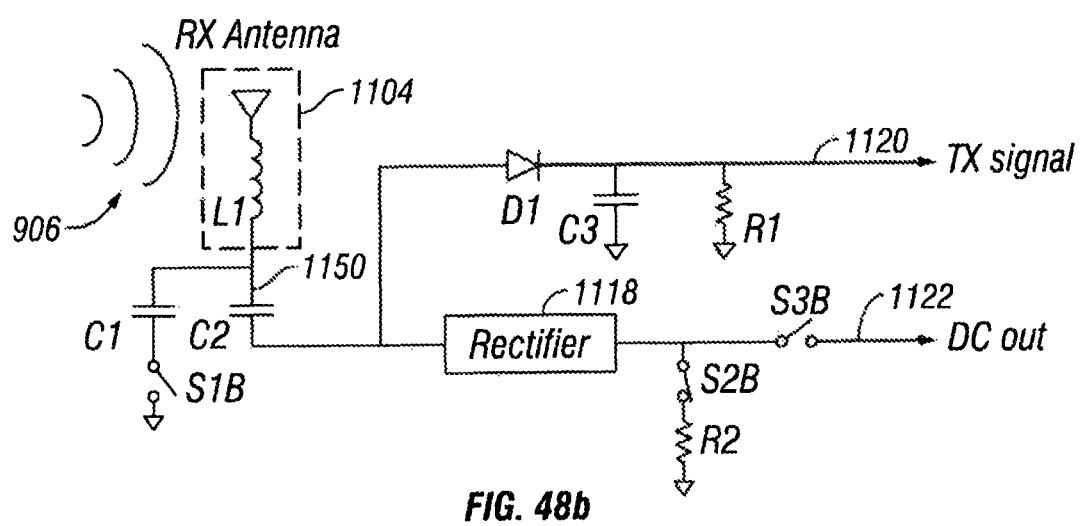
Figure 48C:
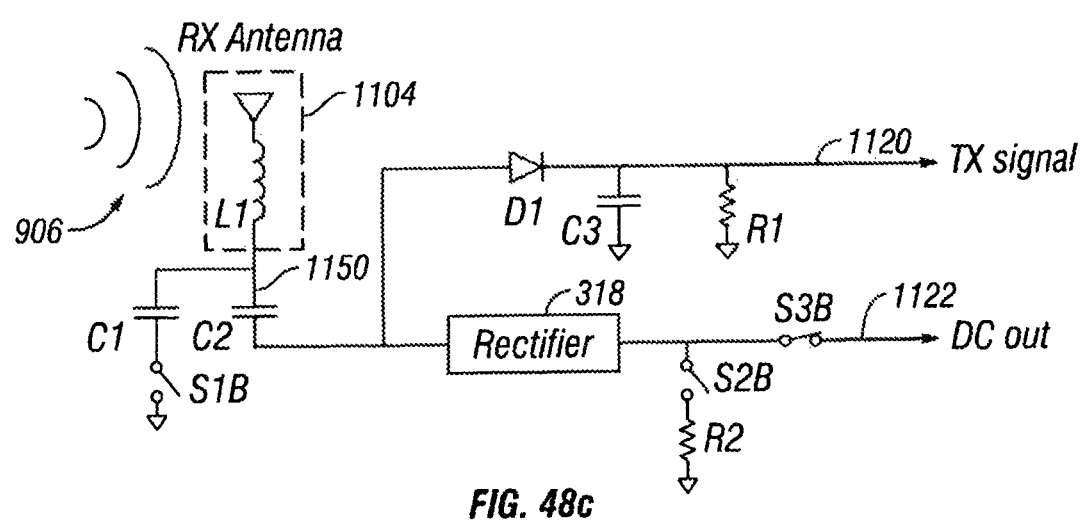

FIGS. 47(a) through 47(c) show a simplified schematic of a portion of receive circuitry in various states to illustrate messaging between a receiver and a transmitter. All of FIGS. 48(a) through 48(c) show the same circuit elements with the difference being state of the various switches. A receive antenna 1104 includes a characteristic inductance L1, which drives node 1150. Node 1150 is selectively coupled to ground through switch S1A. Node 1150 is also selectively coupled to diode D1 and rectifier 1118 through switch S1B. The rectifier 1118 supplies a DC power signal 1122 to a receive monitoring device (not shown) to power the receive monitoring device, charge a battery, or a combination thereof. The diode D1 is coupled to a transmit signal 1120 which is filtered to remove harmonics and unwanted frequencies with capacitor C3 and resistor R1. Thus the combination of D1, C3, and R1 can generate a signal on the transmit signal 1120 that mimics the transmit modulation generated by the transmit modulation signal 1024 discussed above with reference to the transmitter in FIG. 46.

In various embodiments, modulation of the receive monitoring device's current draw and modulation of the receive antenna's impedance can be used to accomplish reverse link signaling. With reference to both FIG. 10A and FIG. 9, as the power draw of the receive monitoring device changes, the load sensing circuit 1016 detects the resulting power changes on the transmit antenna and from these changes can generate the receive signal 1035.

In the exemplary embodiments of FIGS. 48(a) through 48(c), the current draw through the transmitter can be changed by modifying the state of switches S1A and S2A. In FIG. 48(a), switch S1A and switch S2A are both open creating a "DC open state" and essentially removing the load from the transmit antenna 1004. This reduces the current seen by the transmitter.

In FIG. 48(b), switch S1A is closed and switch S2A is open creating a "DC short state" for the receive antenna 1104. Thus the state in FIG. 10B can be used to increase the current seen in the transmitter.

In FIG. 48(c), switch S1A is open and switch S2A is closed creating a normal receive mode (also referred to herein as a "DC operating state") wherein power can be supplied by the DC out signal 322 and a transmit signal 320 can be detected. In the state shown in FIG. 48(c) the receiver receives a normal amount of power, thus consuming more or less power from the transmit antenna than the DC open state or the DC short state.

Reverse link signaling may be accomplished by switching between the DC operating state, FIG. 48(c), and the DC short state, FIG. 48(b). Reverse link signaling also may be accomplished by switching between the DC operating state and the DC open state, FIGS. 48(c) and 48(a) respectively.

Figure 49A:
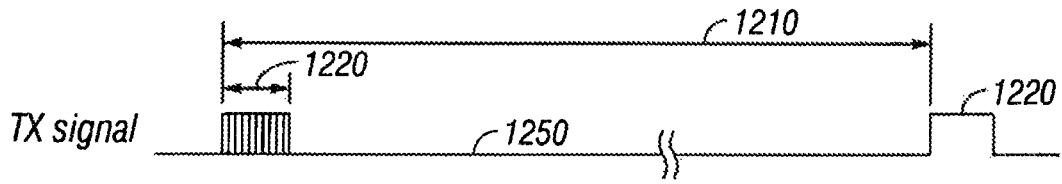
FIGS. 49(a) through 49(c) are timing diagrams illustrating a messaging protocol for communication between a transmitter and a receiver.
Figure 49B:
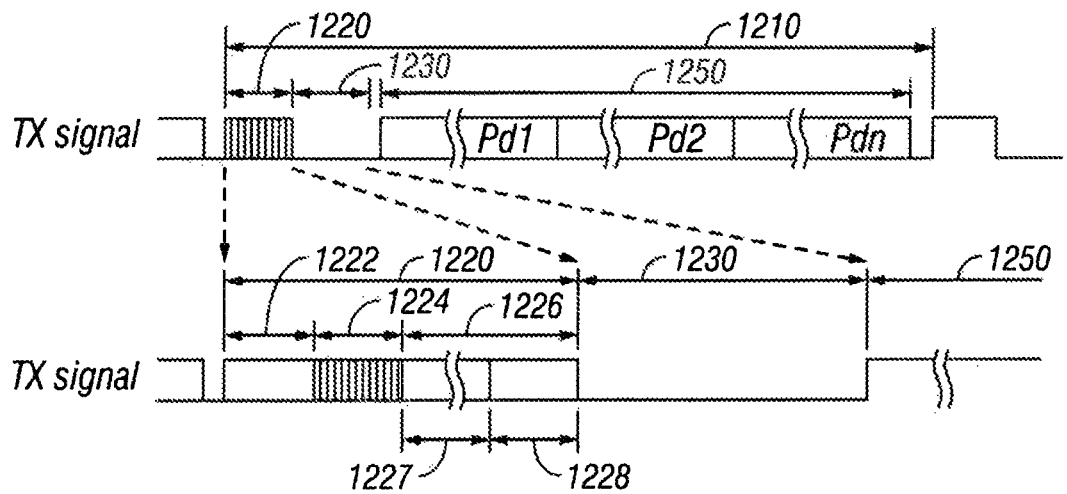
Figure 49C:
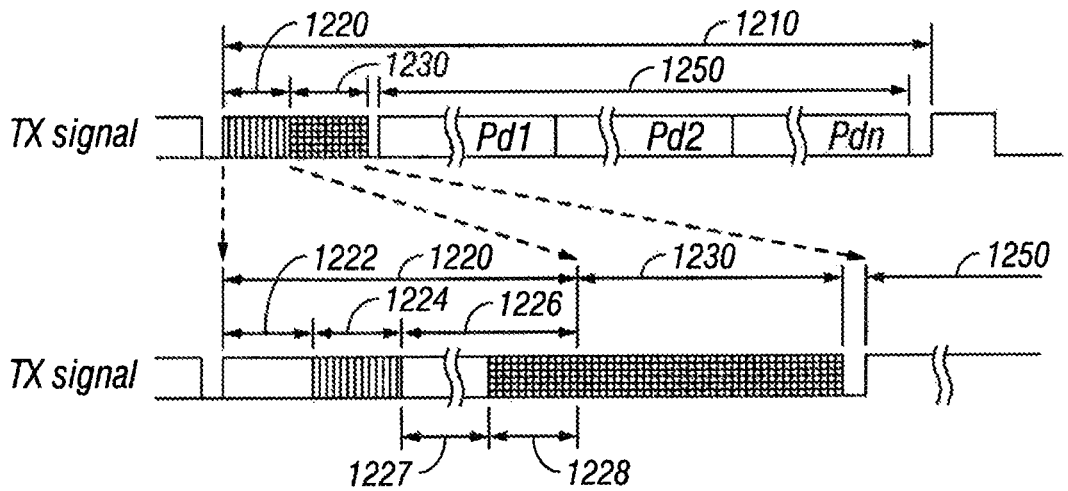

FIGS. 49(a) through 49(c) shows a simplified schematic of a portion of alternative receive circuitry in various states to illustrate messaging between a receiver and a transmitter. All of FIGS. 49(a) through 49(c) illustrate the same circuit elements with the difference being state of the various switches. A receive antenna 1104 includes a characteristic inductance L1, which drives node 1150. Node 1150 is selectively coupled to ground through capacitor C1 and switch SIB. Node 1150 is also AC coupled to diode D1 and rectifier 1118 through capacitor C2. The diode D1 is coupled to a transmit signal 1120 which is filtered to remove harmonics and unwanted frequencies with capacitor C3 and resistor R1. Thus the combination of D1, C3, and R1 can generate a signal on the transmit signal 1120 that mimics the transmit modulation generated by the transmit modulation signal 1024 discussed above with reference to the transmitter of FIG. 46.

The rectifier 1118 is connected to switch S2B, which is connected in series with resistor R2 and ground. The rectifier 1118 also is connected to switch S3B. The other side of switch S3B supplies a DC power signal 1122 to a receive monitoring device (not shown) to power the receive monitoring device, charge a battery, or a combination thereof.

In FIGS. 49(a) through 49(c) the DC impedance of the receive antenna 1104 is changed by selectively coupling the receive antenna to ground through switch SIB. In contrast, in the exemplary embodiments of FIGS. 11A-11C, the impedance of the antenna can be modified to generate the reverse link signaling by modifying the state of switches S1B, S2B, and S3B to change the AC impedance of the receive antenna 1104. In FIGS. 49(a) through 49(c) the resonant frequency of the receive antenna 1104 may be tuned with capacitor C2. Thus, the AC impedance of the receive antenna 1104 may be changed by selectively coupling the receive antenna 1104 through capacitor C1 using switch S1B, essentially changing the resonance circuit to a different frequency that will be outside of a range that will optimally couple with the transmit antenna. If the resonance frequency of the receive antenna 1104 is near the resonant frequency of the transmit antenna, and the receive antenna 1104 is in the near-field of the transmit antenna, a coupling mode may develop wherein the receiver can draw significant power from the radiated field 106.

In FIG. 49(a), switch S1B is closed, which de-tunes the antenna and creates an "AC cloaking state," essentially "cloaking" the receive antenna 1104 from detection by the transmit antenna 1004 because the receive antenna does not resonate at the transmit antenna's frequency. Since the receive antenna will not be in a coupled mode, the state of switches S2B and S3B are not particularly important to the present discussion.

In FIG. 49 (b), switch S1B is open, switch S2B is closed, and switch S3B is open, creating a "tuned dummy-load state" for the receive antenna 1104. Because switch S1B is open, capacitor C1 does not contribute to the resonance circuit and the receive antenna 1104 in combination with capacitor C2 will be in a resonance frequency that may match with the resonant frequency of the transmit antenna. The combination of switch S3B open and switch S2B closed creates a relatively high current dummy load for the rectifier, which will draw more power through the receive antenna 1104, which can be sensed by the transmit antenna. In addition, the transmit signal 1120 can be detected since the receive antenna is in a state to receive power from the transmit antenna.

As illustrated in FIG. 49(c), switch S1B is open, switch S2B is open, and switch S3B is closed, creating a "tuned operating state" for the receive antenna 1104. Because switch S1B is open, capacitor C1 does not contribute to the resonance circuit and the receive antenna 1104 in combination with capacitor C2 will be in a resonance frequency that may match with the resonant frequency of the transmit antenna. The combination of switch S2B open and switch S3B closed creates a normal operating state wherein power can be supplied by the DC out signal 1122 and a transmit signal 1120 can be detected.

Reverse link signaling may be accomplished by switching between the tuned operating state and the AC cloaking state. Reverse link signaling also may be accomplished by switching between the tuned dummy-load state and the AC cloaking state. Reverse link signaling also may be accomplished by switching between the tuned operating state and the tuned dummy-load state because there will be a difference in the amount of power consumed by the receiver, which can be detected by the load sensing circuit in the transmitter.

Referring again to FIG. 46, as a non-limiting example, when in a coupled mode signals may be sent from the transmitter to the receiver. In addition, when in a coupled mode signals may be sent from the receiver to the transmitter, as discussed above with reference to FIGS. 48 (a) through 48 (c) and 49 (a) through 49 (c).

Referring now to FIGS. 49 (a) through 49 (c), timing diagrams are illustrated that are non-limiting examples of an exemplary messaging protocol for communication between a transmitter and a receiver using the signaling techniques discussed above. In one exemplary approach, signals from the transmitter to the receiver are referred to herein as a "forward link" and use a simple AM modulation between normal oscillation and no oscillation. Other modulation techniques are also contemplated. As a non-limiting example, a signal present may be interpreted as a 1 and no signal present may be interpreted as a 0.

In one embodiment, reverse link signaling is provided by modulation of power drawn by the receive monitoring device, which can be detected by the load sensing circuit in the transmitter. As a non-limiting example, higher power states may be interpreted as a 1 and lower power states may be interpreted as a 0. It should be noted that the transmitter must be on for the receiver to be able to perform the reverse link signaling. In addition, the receiver should not perform reverse link signaling during forward link signaling. Furthermore, if two receive monitoring devices attempt to perform reverse link signaling at the same time a collision may occur, which will make it difficult, if not impossible for the transmitter to decode a proper reverse link signal.

In the exemplary embodiment described herein, signaling is similar to a Universal Asynchronous Receive Transmit (UART) serial communication protocol with a start bit, a data byte, a parity bit and a stop bit. Of course, any serial communication protocol may be suitable for carrying the exemplary embodiment of the present invention described herein. For simplicity of description, and not as a limitation, the messaging protocol will be described such that the period for communicating each byte transmission is about 10 mS.

FIG. 49(a) illustrates a simple and low power form of the messaging protocol. A synchronization pulse 1220 will be repeated every recurring period 1210 (about one second in the one embodiment). As a non-limiting example, the sync pulse on time may be about 40 mS. The recurring period 1210 with at least a synchronization pulse 1220 may be repeated indefinitely while the transmitter is on. Note that "synchronization pulse" is somewhat of a misnomer because the synchronization pulse 1150 may be a steady frequency during the pulse period as illustrated by the "white" pulse 1220'. The synchronization pulse 1220 may also include signaling at the resonant frequency with the ON/OFF keying discussed above and as illustrated by the "hatched" pulse 1220. FIG. 49 (a) illustrates a minimal power state wherein power at the resonant frequency is supplied during the synchronization pulse 1220 and the transmit antenna is off during a power period 1250. All receive monitoring devices are allowed to receive power during the synchronization pulse 1220.

Referring to FIG. 49 (b), the recurring period 1210 with a synchronization pulse 1220, a reverse link period 1230 and a power period 1250' are illustrated. In this embodiment, the transmit antenna is on and supplies full power by oscillating at the resonant frequency and not performing any signaling. The upper timing diagram illustrates the entire recurring period 1210 and the lower timing diagram illustrates an exploded view of the synchronization pulse 1220 and the reverse link period 1230. The power period 1250' may be segmented into different periods for multiple receive monitoring devices as is explained below. FIG. 49 (b) shows three power segments Pd1, Pd2, and Pdn for three different receive monitoring devices.

When forward link signaling occurs, the synchronization pulse 1220 may include a warm-up period 1222, a forward link period 1224, and a listening period 1226. The listening period 1226 may include a handover period 1227 and a beginning reverse link period 1228. During the synchronization pulse 1220, the transmitter may send out a forward link message during the forward link period 1200 (indicated by the "hatched" section) and waits for a reply from a receiver during the listening period 1226. In FIG. 12B, no receivers reply, which is indicated by the "white" sections during the listening period 1226.

FIG. 49 (c) is similar to FIG. 49 (b) except that a receiver replies during the beginning reverse link period 1228 and the reverse link period 1230, as indicated by the "cross-hatched" sections. In one embodiment, during the synchronization pulse 1220, the transmitter sends out a forward link message during the forward link period 1200 and waits for a reply from a receiver during the listening period 1226. Any receivers that are going to reply begin their reply before the end of the handover period 1227, during the beginning reverse link period 1228, and possibly during the reverse link period 1230.

As non-limiting examples, five different scenarios are disclosed. . . . In the first scenario, initially no receive monitoring devices are within the coupling-mode region of the transmitter and one receive monitoring device enters the coupling-mode region. When no monitoring device are present in the coupling-mode region the transmitter will remain in the low power state as illustrated in FIG. 49(a) and repeat the synchronization pulse 1220 every recurring period 1210. The synchronization pulse 1220 will include a NDQ during the forward link period 1224 and the transmitter will listen for a reply during the listening period 1226. If no reply is received, the transmitter shuts down until time for the synchronization pulse 1220 of the next recurring period 1210.

When a new receive monitoring device is introduced to the coupling-mode region, the receive monitoring device is initially on and listening for a synchronization pulse 1220. The new receive monitoring device may use the synchronization pulse 1220 for power but should go into a cloaked or non-power reception mode (referred to herein as "getting off the bus") during the power period 1250'. In addition, the new receive monitoring device listens for transmit commands and ignores all transmit commands except an NDQ. When a new receive monitoring device receive an NDQ, it remains on during the handover period 1227, the beginning reverse link period 1228, and possibly the reverse link period 1230. After the forward link period 1224 and before the end of the handover period 1227, the receive monitoring device responds with a NDR, a monitoring device ID of zero (a new monitoring device ID is assigned by the transmitter), a power amount request, a random number and a checksum. The new receive monitoring device then gets off the bus during the power period 1250'.

If the transmitter receives the NDR correctly, it responds on the next synchronization pulse 1220 with a slot assignment (SA) for the new receive monitoring device. The SA includes a monitoring device ID for the new receive monitoring device, a start time, an end time, and a checksum. The start time and end time for this SA will be zero indicating that the new receive monitoring device should not get on the bus for any time period during the power period 1250'. The new receive monitoring device will receive a subsequent SA with actual start times and end times assigning a specific power segment Pdn when it can get on the bus. If the new receive monitoring device does not receive a proper checksum, in remains in new monitoring device mode and responds again to an NDQ.

In the second scenario, no receive monitoring devices are within the coupling-mode region of the transmitter and more than one receive monitoring device enters the coupling-mode region. In this mode, when two new receive monitoring devices are introduced to the coupling-mode region they are initially on the bus all the time. The new receive monitoring devices may use the synchronization pulse 1220 for power but should get off the bus during the power period 1250' once a synchronization pulse 1220 has been received. In addition, the new receive monitoring devices listen for transmit commands and ignore all transmit commands except an NDQ. When the new receive monitoring device receive an NDQ, they remain on during the handover period 1227, the beginning reverse link period 1228, and possibly the reverse link period 1230. After the forward link period 1224 and before the end of the handover period 1227, the receive monitoring devices responds with a NDR, a monitoring device ID of zero (a new monitoring device ID will be assigned by the transmitter), a power amount request, a random number and a checksum.

However, because two or more receive monitoring devices are responding at the same time, and likely have different random numbers and checksums, the message received by the transmitter will be garbled, and the checksum in the transmitter will not be accurate. As a result, the transmitter will not send out a SA on the subsequent synchronization pulse 1220.

When an immediate SA is not forthcoming after an NDR, each of the receive monitoring devices waits a random number of subsequent NDQs before responding with an NDR. For example, two monitoring devices both respond to the first NDQ so no subsequent SA happens. Device 1 decides to wait four NDQs before responding to another NDQ. Device 2 decides to wait two NDQs before responding to another NDQ. As a result, on the next NDQ sent out by the transmitter, neither monitoring device responds with an NDR. On the next NDQ sent out by the transmitter, only monitoring device 2 responds with an NDR, the transmitter successfully receives the NDR and sends out an SA for monitoring device 2. On the next NDQ, monitoring device 2 does not respond because it is no longer a new monitoring device and monitoring device 1 does not respond because its random waiting period has not elapsed. On the next NDQ sent out by the transmitter, only monitoring device 1 responds with an NDR, the transmitter successfully receives the NDR and sends out an SA for monitoring device 1.

In the third scenario, at least one receive monitoring device is in the coupling-mode region and a new receive monitoring device enters the coupling-mode region. In this mode, the new receive monitoring devices is introduced to the coupling-mode region and is initially on the bus all the time. The new receive monitoring devices may use the synchronization pulse 1220 for power but should get off the bus during the power period 1250' once a synchronization pulse 1220 has been received. In addition, the new receive monitoring devices listen for transmit commands and ignore all transmit commands except an NDQ. Periodically, the transmitter will issue an NDQ to see if any new monitoring devices have entered the coupling-mode region. The new monitoring device will then reply with an NDR. On the subsequent synchronization pulse 1220, the transmitter will issue an SA for the new monitoring device with no power slots assigned. The transmitter then recalculates power allocation for all the monitoring devices in the coupling-mode region and generates new SAs for each monitoring device so there are no overlapping power segments Pdn. After each monitoring device receives its new SA, it begins getting on the bus only during its new Pdn.

In the fourth scenario, normal power delivery operation continues with no receive monitoring device entering or leaving the coupling-mode region. During this scenario, the transmitter will periodically ping each monitoring device with a monitoring device query (DQ). The queried monitoring device responds with a monitoring device status (DS). If the DS indicates a different power request, the transmitter may reallocate power allocation to each of the monitoring devices in the coupling-mode region. The transmitter will also periodically issues an NDQ as was explained above for the third scenario.

In the fifth scenario, a monitoring device is removed from the coupling-mode region. This "removed" state may be that the monitoring device is physically removed from the coupling-mode region, the monitoring device is shut off, or the monitoring device cloaks itself, perhaps because it does not need any more power. As stated earlier, the transmitter periodically sends out a DQ for all the monitoring devices in the coupling-mode region. If two consecutive DQs to a specific monitoring device do not return a valid DS, the transmitter removes the monitoring device from its list of allocated monitoring devices and reallocates the power period 1250' to the remaining monitoring devices. The transmitter will also assign the missing monitoring device a power allocation of zero time in case it is still receiving by is unable to transmit. If a monitoring device was erroneously removed from the power allocation, it may regain power allocation by responding to and NDQ with a proper NDR.

In an exemplary embodiment, a wireless charging monitoring devices may display a visible signal, such as, for example, a light to the user indicating that it has successfully entered the charging region and registered itself to the local transmitter. This will give the user positive feedback that a monitoring device is indeed prepared to charge.

FIGS. 50(a) through 50(d) are block diagrams illustrating a beacon power mode for transmitting power between a transmitter and a one or more receivers. FIG. 50 (a) illustrates a transmitter 1320 having a low power "beacon" signal 1325 when there are no receive monitoring devices in the beacon coupling-mode region 1310. The beacon signal 1325 may be, as a non-limiting example, such as in the range of about 10 to about 20 mW RF. This signal may be adequate to provide initial power to a monitoring device to be charged when it is placed in the coupling-mode region.

Figure 50A:
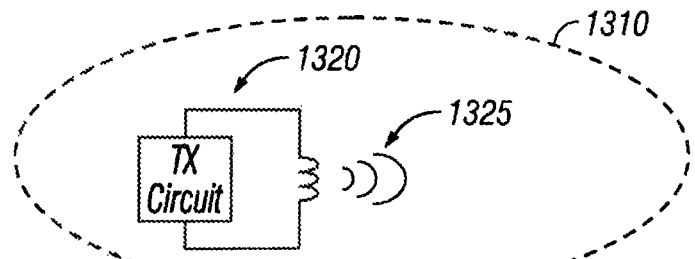
FIGS. 50(a) through 50(d) are simplified block diagrams illustrating a beacon power mode for transmitting power between a transmitter and a receiver.
Figure 50B:
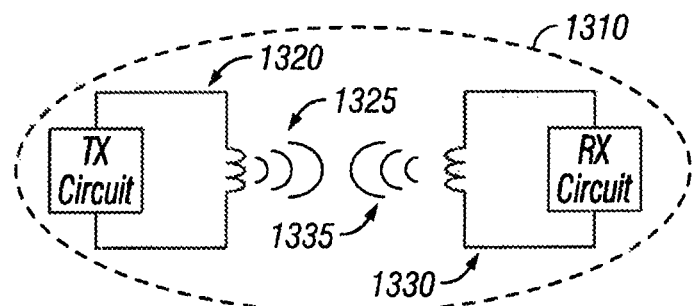

FIG. 50(b) illustrates a receive monitoring device 1330 placed within the beacon coupling-mode region 1310 of the transmitter 1320 transmitting the beacon signal 1325. If the receive monitoring device 1330 is on and develops a coupling with the transmitter it will generate a reverse link coupling 1335, which is really just the receiver accepting power from the beacon signal 1325. This additional power, may be sensed by the load sensing circuit 1016, FIG. 46, of the transmitter. As a result, the transmitter may go into a high power mode.

Figure 50C:
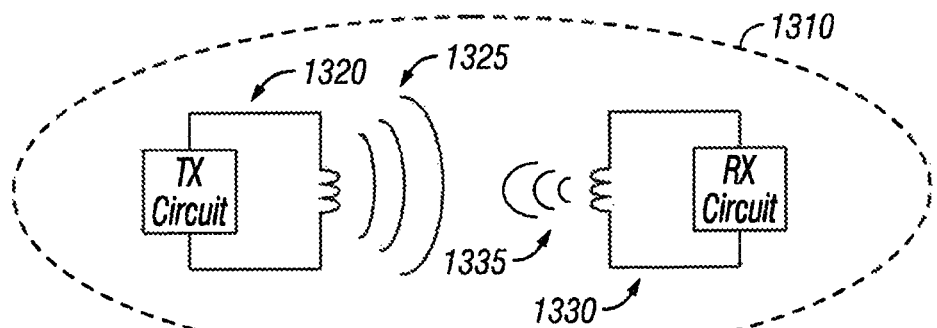

FIG. 50(c) illustrates the transmitter 1320 generating a high power signal 1325' resulting in a high power coupling-mode region 1310'. As long as the receive monitoring device 1330 is accepting power and, as a result, generating the reverse link coupling 1335, the transmitter will remain in the high power state. While only one receive monitoring device 1330 is illustrated, multiple receive monitoring devices 1330 may be present in the coupling-mode region 1310. If there are multiple receive monitoring device 1330 they will share the amount of power transmitted by the transmitter based on how well each receive monitoring device 1330 is coupled. For example, the coupling efficiency may be different for each receive monitoring device 1330 depending on where the monitoring device is placed within the coupling-mode region 1310 as was explained above with reference to FIGS. 46 and 47.

Figure 50D:
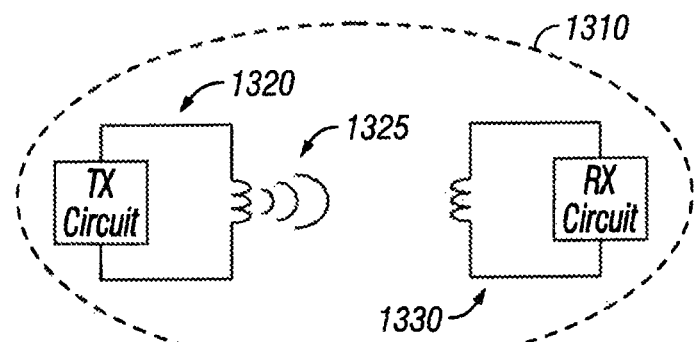

FIG. 50(d) illustrates the transmitter 1320 generating the beacon signal 1325 even when a receive monitoring device 1330 is in the beacon coupling-mode region 1310. This state may occur when the receive monitoring device 1330 is shut off, or the monitoring device cloaks itself, perhaps because it does not need any more power.

As with the time-multiplexing mode, the receiver and transmitter may communicate on a separate communication channel (e.g., BLUETOOTH®, zigbee, etc.). With a separate communication channel, the transmitter may determine when to switch between beacon mode and high power mode, or create multiple power levels, based on the number of receive monitoring devices in the coupling-mode region 1310 and their respective power requirements.

Certain embodiments of the invention include enhancing the coupling between a relatively large transmit antenna and a small receive antenna in the near-field power transfer between two antennas through introduction of additional antennas into the system of coupled antennas that will act as repeaters and will enhance the flow of power from the transmitting antenna toward the receiving antenna.

In some embodiments, one or more extra antennas are used that couple to the transmit antenna and receive antenna in the system. These extra antennas comprise repeater antennas, such as active or passive antennas. A passive antenna may include simply the antenna loop and a capacitive element for tuning a resonant frequency of the antenna. An active element may include, in addition to the antenna loop and one or more tuning capacitors, an amplifier for increasing the strength of a repeated near-field radiation.

The combination of the transmit antenna and the repeater antennas in the power transfer system may be optimized such that coupling of power to very small receive antennas is enhanced based on factors such as termination loads, tuning components, resonant frequencies, and placement of the repeater antennas relative to the transmit antenna.

A single transmit antenna exhibits a finite near-field coupling mode region.

Accordingly, a user of a monitoring device charging through a receiver in the transmit antenna's near-field coupling mode region may require a considerable user access space that would be prohibitive or at least inconvenient. Furthermore, the coupling mode region may diminish quickly as a receive antenna moves away from the transmit antenna.

A repeater antenna may refocus and reshape a coupling mode region from a transmit antenna to create a second coupling mode region around the repeater antenna, which may be better suited for coupling energy to a receive antenna.

FIG. 51 (a) illustrates a large transmit antenna 1410C with three smaller repeater antennas 1420C disposed coplanar with, and within a perimeter of, the transmit antenna 1410C. The transmit antenna 1410C and repeater antennas 1420C are formed on a table 1440. Various monitoring devices including receive antennas 1430C are placed at various locations within the transmit antenna 1410C and repeater antennas 14200. The exemplary embodiment of FIG. 14A may be able to refocus the coupling mode region generated by the transmit antenna 1410C into smaller and stronger repeated coupling mode regions around each of the repeater antennas 1420C. As a result, a relatively strong repeated near-field radiation is available for the receive antennas 1430C. Some of the receive antennas are placed outside of any repeater antennas 1420C. Recall that the coupled mode region may extend somewhat outside the perimeter of an antenna. Therefore, receive antennas 1430C may be able to receive power from the near-field radiation of the transmit antenna 1410C as well as any nearby repeater antennas 1420C. As a result, receive antennas placed outside of any repeater antennas 1420C, may be still be able to receive power from the near-field radiation of the transmit antenna 1410C as well as any nearby repeater antennas 1420C.

FIG. 51 (b) illustrates a large transmit antenna 1410D with smaller repeater antennas 1420D with offset coaxial placements and offset coplanar placements relative to the transmit antenna 1410D. A monitoring device including a receive antenna 1430D is placed within the perimeter of one of the repeater antennas 1420D. As a non-limiting example, the transmit antenna 1410D may be disposed on a ceiling 1446, while the repeater antennas 1420D may be disposed on a table 1440. The repeater antennas 1420D in an offset coaxial placement may be able to reshape and enhance the near-field radiation from the transmitter antenna 1410D to repeated near-field radiation around the repeater antennas 1420D. As a result, a relatively strong repeated near-field radiation is available for the receive antenna 1430D placed coplanar with the repeater antennas 1420D.

While the various transmit antennas and repeater antennas have been shown in general on surfaces, these antennas may also be disposed under surfaces (e.g., under a table, under a floor, behind a wall, or behind a ceiling), or within surfaces (e.g., a table top, a wall, a floor, or a ceiling).

Figure 52:
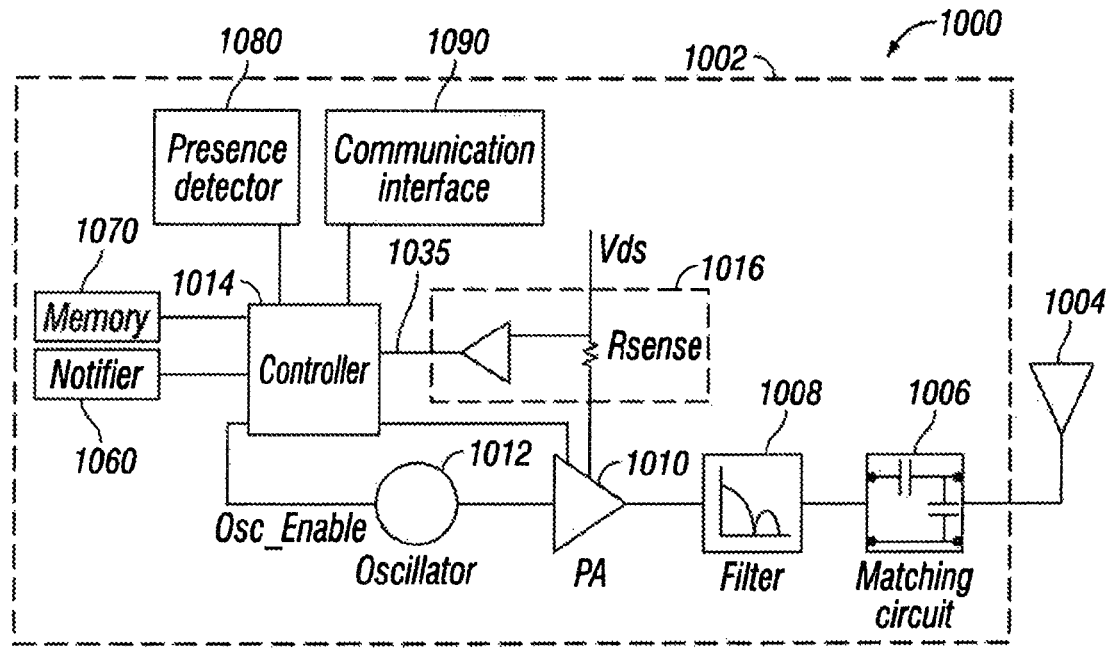
FIG. 52 is a simplified block diagram of a transmitter including a notification element.

FIG. 52 is a block diagram of a transmitter 1000 for transmitting power to, communicating with, and tracking receiver monitoring devices according to one or more embodiments of the present invention. A transmitter 1000 may gather and track information about the whereabouts and status of receiver monitoring devices that may be associated with the transmitter 1000. The transmitter 1000 of FIG. 15 is similar to that of FIG. 44 and, therefore, does not need to be explained again. However, in FIG. 52 the transmitter circuitry 1002 may include a presence detector 1080, an enclosed detector 1090, or a combination thereof, connected to the controller 1014 (also referred to as a processor herein). The controller 1014 may adjust an amount of power delivered by the amplifier 1010 in response to presence signals from the presence detector 1080 and the enclosed detector 1090. The transmitter may receive power through a number of power sources, such as, for example, an AC-DC converter to convert conventional AC power present in a building, a DC-DC converter (not shown) to convert a conventional DC power source to a voltage suitable for the transmitter 1000, or directly from a conventional DC power source.

As a non-limiting example, the presence detector 1080 may be a motion detector utilized to sense the initial presence of a monitoring device to be charged that is inserted into the coverage area of the transmitter. After detection, the transmitter may be turned on and the RF power received by the monitoring device may be used to toggle a switch on the Rx monitoring device in a pre-determined manner, which in turn results in changes to the driving point impedance of the transmitter.

As another non-limiting example, the presence detector 1080 may be a detector capable of detecting a human, for example, by infrared detection, motion detection, or other suitable means. In some exemplary embodiments, there may be regulations limiting the amount of power that a transmit antenna may transmit at a specific frequency. In some cases, these regulations are meant to protect humans from electromagnetic radiation. However, there may be environments where transmit antennas are placed in areas not occupied by humans, or occupied infrequently by humans, such as, for example, garages, factory floors, shops, and the like. If these environments are free from humans, it may be permissible to increase the power output of the transmit antennas above the normal power restrictions regulations. In other words, the controller 1014 may adjust the power output of the transmit antenna 1004 to a regulatory level or lower in response to human presence and adjust the power output of the transmit antenna 1004 to a level above the regulatory level when a human is outside a regulatory distance from the electromagnetic field of the transmit antenna 1004.

As a non-limiting example, the enclosed detector 1090 (may also be referred to herein as an enclosed compartment detector or an enclosed space detector) may be a monitoring device such as a sense switch for determining when an enclosure is in a closed or open state. When a transmitter is in an enclosure that is in an enclosed state, a power level of the transmitter may be increased.

In certain embodiments, a method by which the transmitter 1000 does not remain on indefinitely may be used. In this case, the transmitter 1000 may be programmed to shut off after a user-determined amount of time. This feature prevents the transmitter 1000, notably the power amplifier 1010, from running long after the wireless monitoring devices in its perimeter are fully charged. This event may be due to the failure of the circuit to detect the signal sent from either the repeater or the receive coil that a monitoring device is fully charged. To prevent the transmitter 1000 from automatically shutting down if another monitoring device is placed in its perimeter, the transmitter 1000 automatic shut off feature may be activated only after a set period of lack of motion detected in its perimeter. The user may be able to determine the inactivity time interval, and change it as desired. As a non-limiting example, the time interval may be longer than that needed to fully charge a specific type of wireless monitoring device under the assumption of the monitoring device being initially fully discharged.

The transmit circuitry 1002 can include a user-perceivable notifier 1060 for indicating to a user notification information about receiver monitoring devices that are in the coupling-mode region of the transmit antenna 1004. In addition, the transmit circuitry 1002 may include a memory 1070 for storing information about the receiver monitoring devices that it communicates with as well as other data and processing instructions.

Figure 53:
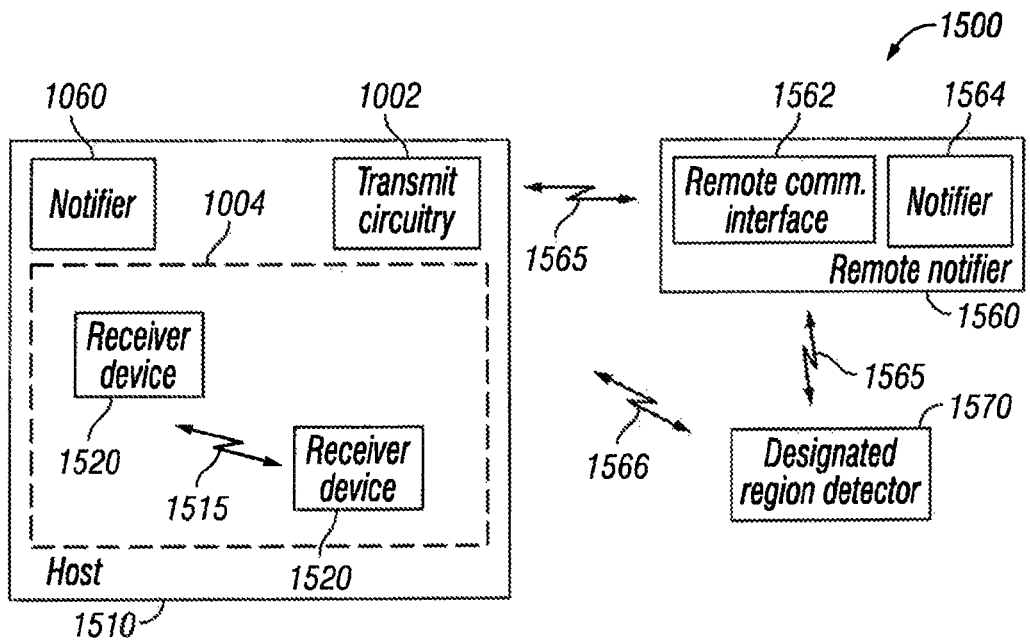
FIG. 53 is a simplified block diagram of wireless power transfer system including notification elements.

FIG. 53 is a block diagram of wireless power transmitting system 700 including notification elements 1060 and 760. The system 700 includes a host monitoring device 710 with a transmitter including transmit circuitry 1002 and a transmit antenna 1004. The host monitoring device 710 may also include a user-perceivable notifier 1060. Multiple receiver monitoring devices 720 with receive antennas may be placed in a coupling-mode region of the transmit antenna 1004. When in the coupling-mode region, the receiver monitoring devices 720 may receive power from the host monitoring device 710 and may communicate with the host monitoring device 710 as discussed above with respect to FIGS. 48 (*a*) through 48 (*c*).

Certain embodiments of the present invention allow power transfer to several monitoring devices at the same time. In addition, while the receiver monitoring devices 720 are in the charging area (i.e., in or near the coupling-mode region) they can exchange certain pre-specified information with the host monitoring device 710 or other receiver monitoring device 720.

Receiver information may include items such as; unique monitoring device identifiers, monitoring device types, contact information, and user-programmed information about the monitoring device. For example, the monitoring device may be a music player, from a specific manufacturer, that is tagged with a user's name. As another example, the monitoring device may be an electronic book, from a specific manufacturer, with a specific serial number that is tagged with a user's name.

The owners of each monitoring device may need to pre-configure their monitoring devices to allow such information sharing capability, but once enabled, the monitoring devices could communicate without direct human interaction.

In many situations it is common user behavior to charge certain groups of objects simultaneously. For example, people often charge both a cell-phone and an accompanying BLUETOOTH® headset at the same time. In addition, parents may wish to ensure that children have their cell-phone, net-book, E-reader, and the like charged each night so that they are ready for school the next day. Parents may teach children to charge all their monitoring devices at the same time on a certain host monitoring device 710. If the children are not charging their monitoring devices together, it could mean a monitoring device has been lost, or simply that the child has forgotten to charge all monitoring devices at the end of that specific day. In either case, it would be useful for the parent(s) to get a notification if a monitoring device is missing or is not being charged.

The receiver monitoring devices 720 and host monitoring device 710 may communicate on a separate communication channel 715, as a non-limiting example BLUETOOTH®, Zigbee, near field communication and the like). With a separate communication channel, the transmitter may determine when to switch between using the wireless power communication and the separate communication channel 715.

As a non-limiting example, for small amounts of information to be transferred between the host monitoring device 710 and receiver monitoring devices 720, the monitoring devices could possibly use near field communication (NFC) or the reflected impedance based on-off keying discussed above.

If the amount of data to be transferred would take longer than, for example only, 10 second with either NFC or reflected impedance techniques, then a be-directional personal area network (PAN) link may be created. Thus, PAN technologies such as BLUETOOTH®, or 60 GHz could be used to communicate between the host monitoring device 1510 and the receiver monitoring device 1520. This peer-to-peer connection could be negotiated on a lowest common denominator basis where the lowest common denominator would be the PAN technology that was supported by all the receiver monitoring devices 1520 in the coupling-mode region. In other words, selection of the appropriate technology could be based first on the amount of data to be transferred and second on the kind of radio technologies supported by the various monitoring devices.

The wireless power transmitting system 1500 may include a remote notifier 1560. Both the notifier 1060 on the host monitoring device 1510 and the remote notifier 1560 may have a wide range of notification elements. As non-limiting examples, the notifier (260 and 1560) may be a simple light indicating that a receiver monitoring device 1520 is present, multiple lights indicating how many receiver monitoring devices 1520 are present, an alpha-numeric display for presenting information about the receiver monitoring devices 1520, or a full-color display for presenting detailed information about receiver monitoring devices 1520. The notifier (260 and 1560) may include an auditory signaler for notifying a user regarding the presence or absence of a specific receiver monitoring device 1520 and other information about receiver monitoring devices 1520. In addition, the remote notifier 1560 may be a web-site for displaying information about the receiver monitoring devices 1520 on a remote computer. Thus, as a non-limiting example, a user that forgot her cell phone may check the web-site from work to determine whether she left the cell phone near the host monitoring device 1510.

The power transmitting system 1500 may include a designated region detector 1570. This designated region detector 1570 may be as simple as a switch on an exit door from a home or office. However, it may be more complicated, such as a presence detector as discussed above. Thus, the designated region detector 1570 may be used to detect when a host monitoring device 1510 is leaving a designated region and communicate a notification indicating such to the host monitoring device 1510.

The remote notifier 1560, designated region detector 1570, and host monitoring device 1510 may communicate on a communication channel 1565 such as radio frequency signaling, infrared signaling, BLUETOOTH®, Zigbee, the 802.11 communication protocols, and combinations thereof.

Figure 54:
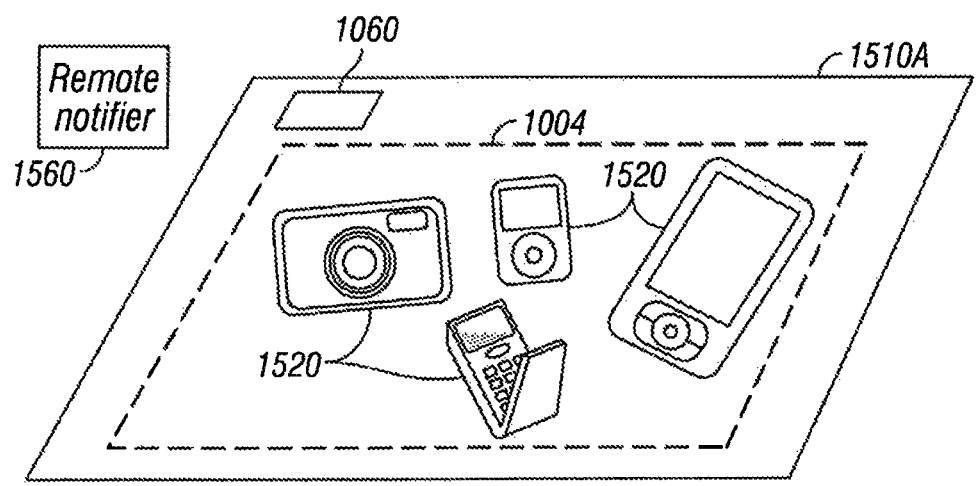
FIG. 54 illustrates a host device with a notifier and including receiver devices.
Figure 55:
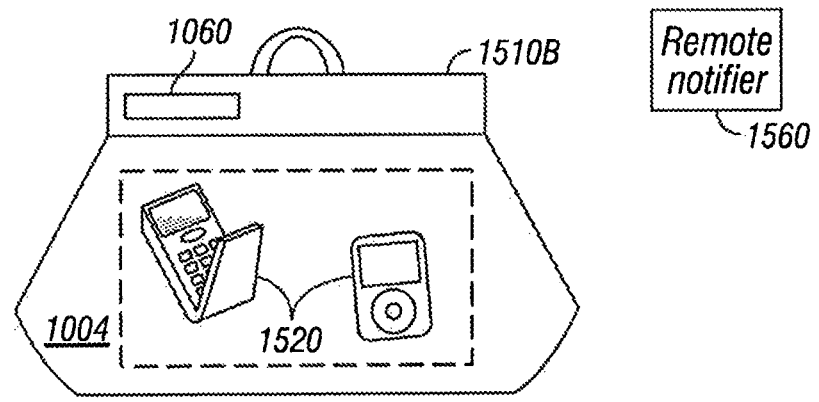
FIG. 55 illustrates another host device with a notifier and including receiver devices.

FIG. 54 illustrates a host monitoring device 1510A with a notifier 1560 and including receiver monitoring devices 1520 within the coupling-mode region of a transmit antenna 1004. A remote notifier 1560 may also be in communication with the host monitoring device 1510A. In FIG. 55, the host monitoring device 1510 is illustrated as a charging mat, but could be integrated into furniture or building elements such as walls, ceilings, and floors. It will be appreciated that the host monitoring device can be at the telemetry system described above.

FIG. 55 illustrates another host monitoring device 1510B with a notifier 1060 and including receiver monitoring devices 1520 within the coupling-mode region of a transmit antenna 1004. A remote notifier 1560 may also be in communication with the host monitoring device 1510B. The host monitoring device 1510B of FIG. 18 may be an item such as, for example, a handbag, backpack, or briefcase with a transmitter built in. Alternatively, the host monitoring device may be a portable transmitter specifically designed for a user to transport receiver monitoring devices 1520, such as a charging bag.

Figure 56:
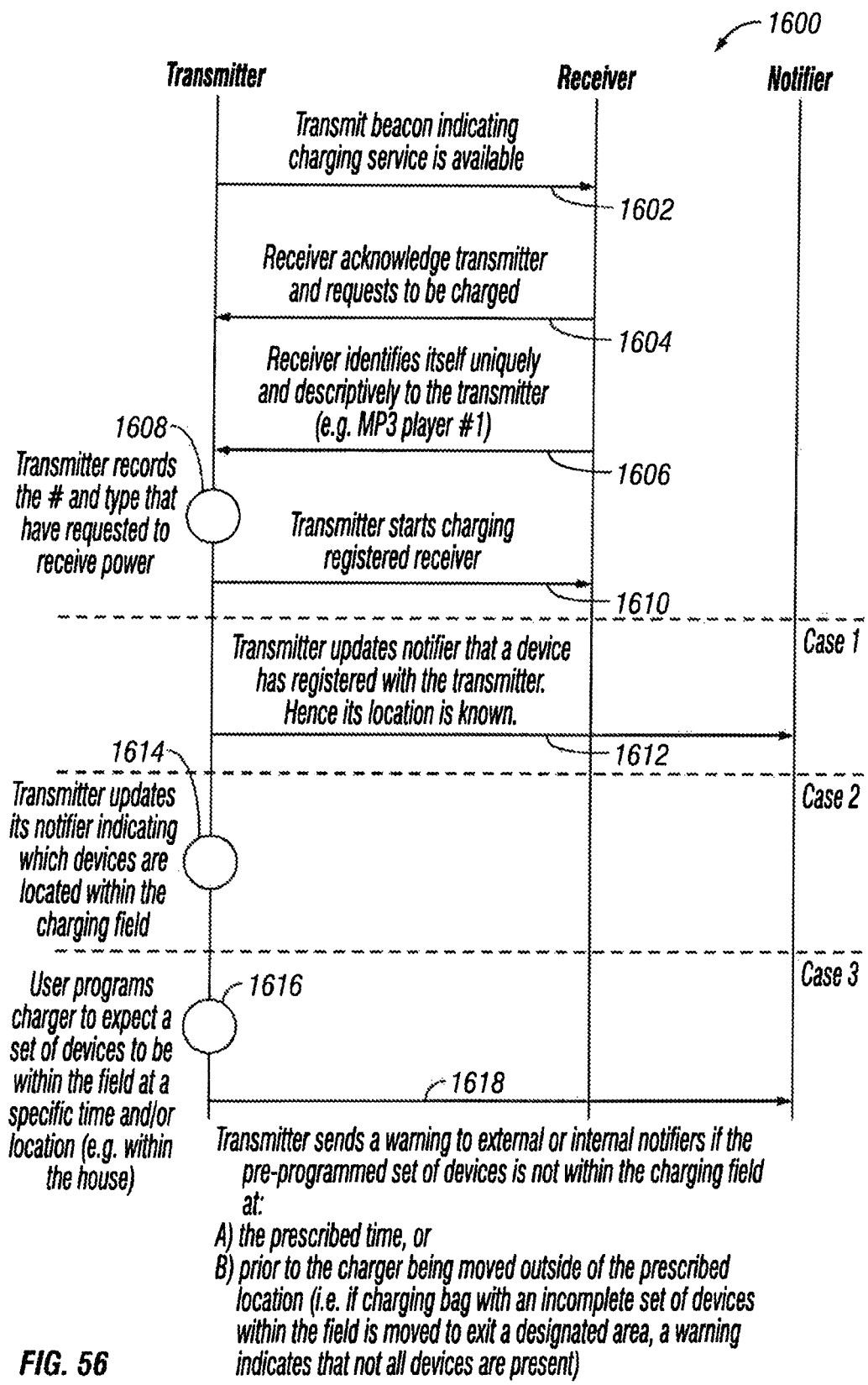
FIG. 56 is a simplified flow diagram illustrating acts that may be performed in tracking receiver devices.

FIG. 56 is a flow diagram illustrating acts that may be performed in communicating with and tracking receiver monitoring devices. It is noted that the exemplary embodiments may be described in terms of a process that is depicted as a flowchart, a flow diagram, a structure diagram, or a block diagram. Although a flowchart may describe operational acts as a sequential process, many of these acts can be performed in another sequence, in parallel, or substantially concurrently. In addition, the order of the acts may be re-arranged. A process is terminated when its acts are completed. A process may correspond to a method, a function, a procedure, a subroutine, a subprogram, etc. Furthermore, the methods disclosed herein may be implemented in hardware, software, or a combination thereof.

To keep track of receiver monitoring devices 1620 within the coupling-mode region of the host monitoring device 1510, exemplary embodiments may take advantage of the fact that the wireless charging protocol discussed above already allows for a receiver monitoring device to request power. Additional acts, additional information, or a combination thereof as part of the charging protocol or other communication channel 1515 would allow the host monitoring device 1510 to keep track of various receiver monitoring devices 1520 within its coupling-mode region.

In certain embodiments, the on-off keying communication protocol discussed above can be expanded to enable the receiver monitoring device 1520 requesting charge to identify itself with a unique identifier, such as, for example a serial number or a tag associating the receiver monitoring device with a specific user. The requesting receiver monitoring device 1520 may also communicate additional information such as class of monitoring device (e.g., camera, cell phone, media player, and personal digital assistant).

In certain embodiments, at operation 1602 a transmitter (i.e., a power transmitting monitoring device 1000 on a host monitoring device 1510) transmits its beacon or other generic communication indicating that it is available to transmit power to receiver monitoring devices 1520.

In operation 1604, one or more receivers acknowledge the transmitter and request to receive power, which may be used to charge the monitoring device, operate the monitoring device, or a combination thereof.

In operation 1606, the receiver identifies itself to the transmitter with a unique identifier, such as a tag associated with the monitoring device, a serial number, or other unique data. The receiver may also include additional information such as the type of monitoring device, information about the monitoring device's capabilities, and information about the monitoring device's owner.

In operation 1608, the transmitter records the unique identifier and other suitable information about the receivers that have communicated such information. The transmitter may also associate the information with other information on the transmitter.

For example, the transmitter may be programmed to correlate a specific monitoring device with a specific user such that more detailed information can be presented on the notifiers 1060 and 1560. In other words, the transmitter may be programmed to associate a specific serial number with the user "John" such that the notifier may be able to indicate information such as, "John's PDA is present in host monitoring device 1" or John's PDA is expected to be at host monitoring device 2, but is not present."

In operation 1610, the transmitter begins, or resumes, transmitting power to the receivers within its coupling-mode region.

Additional features may be included in some exemplary embodiments of the invention. As non-limiting examples, three cases of possible additional features are outlined below and illustrated in FIG. 56.

In case 1 illustrated by operation 1612, the transmitter may update the remote notifier 1560 that a receiver monitoring device 1520 has registered with the transmitter. Thus, the location of that receiver monitoring device 1520, as well as other information about that receiver monitoring device 1520, is known and may be presented on the remote notifier 1560.

In case 2 illustrated by operation 1614, the transmitter may update its own notifier 1060 that a receiver monitoring device 1520 has registered with the transmitter. Thus, the location of that receiver monitoring device 1520, as well as other information about that receiver monitoring device 1520, is known and may be presented on the notifier 1060.

Case 3 is illustrated by operation 816 and 818. In operation 816, the transmitter may be programmed to expect certain receiver monitoring devices 1520 to be in its coupling-mode region during certain time periods. In addition, portable host monitoring devices 1510B may be programmed to expect receiver monitoring devices 1520 to be at certain locations during certain times. For example, a portable host monitoring device 1510B may be programmed to indicate that a PDA should be in the office during working hours and at home during non-working hours. Thus, a user may pre-set a handbag (e.g., host monitoring device 1510B) capable of charging portable monitoring devices, to expect a certain set of receiver monitoring devices 1520 to be placed within the handbag prior to the bag leaving the house.

As non-limiting examples, this time and position information that may be programmed into host monitoring devices may be used to allow a host monitoring device to warn if certain receiver monitoring devices aren't on a charger pad 1510A at a certain time. In addition, a host monitoring device can warn if pre-specified monitoring devices are not in, say a charging bag 1510B, when the user is walking outside the house "region." This may be accomplished by the designated region detector 1570 notifying the charging bag 1510B when the charging bag 1510B is leaving the house. The charging bag 1510B can then check its programming and state information about receiver monitoring devices 1520 to determine which receiver monitoring devices 1520 are present in the charging bag 1510B and which receiver monitoring devices 1520 are expected to be in the charging bag 1510B. Based on this determination, the charging bag 1510B may send a message to its notifier 1060, the remote notifier 1560, or a combination thereof to indicate whether all the expected monitoring devices are present or some of the expected monitoring devices are missing from the charging bag 1510B.

The various illustrative logical blocks, modules, and circuits described in connection with the exemplary embodiments disclosed herein may be implemented or performed with a general purpose processor, a Digital Signal Processor (DSP), an Application Specific Integrated Circuit (ASIC), a Field Programmable Gate Array (FPGA) or other programmable logic monitoring device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing monitoring devices, e.g., a combination of a DSP and a microprocessor, a plurality of microprocessors, one or more microprocessors in conjunction with a DSP core, or any other such configuration.

The steps of a method or algorithm described in connection with the exemplary embodiments disclosed herein may be embodied directly in hardware, in a software module executed by a processor, or in a combination of the two. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage monitoring devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

The foregoing description of various embodiments of the claimed subject matter has been provided for the purposes of illustration and description. It is not intended to be exhaustive or to limit the claimed subject matter to the precise forms disclosed. Many modifications and variations will be apparent to the practitioner skilled in the art. Particularly, while the concept "component" is used in the embodiments of the systems and methods described above, it will be evident that such concept can be interchangeably used with equivalent concepts such as, class, method, type, interface, module, object model, and other suitable concepts. Embodiments were chosen and described in order to best describe the principles of the invention and its practical application, thereby enabling others skilled in the relevant art to understand the claimed subject matter, the various embodiments and with various modifications that are suited to the particular use contemplated.

What is claimed is:

1. A wireless power transmission system, comprising:
   a transmit antenna that in operation produces a wireless field;
   an amplifier coupled to the transmit antenna;
   a load sensing circuit coupled to the amplifier;
   a controller coupled to the load sensing circuit;
   a monitoring device with a microphone and sensors to determine air quality, sound level, light quality and ambient temperature near a person;
   an accelerometer configured to detect a person's movement information, the accelerometer and the monitoring device configured to assist to determine a person's sleep information and sleep behavior information, the microphone configured to record the person's movement sounds detected by the accelerometer, the recording of sensors that determine sound level, light quality and ambient temperature relative to the person's sleep information and sleep behavior information, the recording of the sensors beginning a stoppage of the monitoring in response to the accelerator detection of movement information; and
   a communication interface that in operation receives information about a unique user ID when the load sensing circuit indicates the monitoring device is within the wireless field, the indication created using at least a change in power consumption.

2. The system of claim 1, wherein the load sensing circuit in operation produces a response signal representative of the changes in power consumption.

3. The system of claim 1, wherein the controller is further configured to determine, at least one of a presence of another device within the wireless field or the information of the device previously indicated to be within the wireless field.

4. The system of claim 1, further comprising
   a wireless communicator coupled to the controller, the wireless communicator configured to communicate with the monitoring device over a communication channel different from a wireless communication channel used to generate the wireless field, wherein the controller is further configured to monitor the information from the communication channel.

5. The system of claim 4, further comprising:
   a second monitoring device with a receive antenna in the wireless field and wherein the communication channel is configured for a peer-to-peer communication between the device and the another device.

6. The system of claim 4, wherein the different communication channel is a wireless technology standard for exchanging data communication channel.

7. The system of claim 1, wherein the controller in operation monitors and processes additional information about another monitoring device with a receive antenna in the wireless field to generate additional notification information.

8. The system of claim 1, further comprising:
   a memory coupled to the processor, the memory configured to store at least one of the information about the monitoring device or the notification information.

* * * * *